United States Patent [19]

Moses

[11] Patent Number: 5,474,920
[45] Date of Patent: Dec. 12, 1995

[54] MODIFIED THERMO-RESISTANT DNA POLYMERASES

[75] Inventor: Robb E. Moses, Portland, Oreg.

[73] Assignee: State of Oregon, Acting by and Through the Oregon State Board of Higher Education on Behalf of the Oregon Health Sciences University, Portland, Oreg.

[21] Appl. No.: 156,020

[22] Filed: Nov. 23, 1993

[51] Int. Cl.$^6$ .................................................. C12N 9/12
[52] U.S. Cl. ................... 435/194; 435/252.3; 536/23.2; 935/10; 935/14
[58] Field of Search ................... 435/194, 252.3; 536/23.2; 935/10, 14

[56] References Cited

U.S. PATENT DOCUMENTS

| | | | |
|---|---|---|---|
| 4,399,216 | 8/1983 | Axel | 435/6 |
| 4,419,446 | 12/1983 | Howley et al. | 435/68 |
| 4,601,798 | 7/1986 | Jacubert et al. | 204/61 |
| 4,683,202 | 7/1987 | Mullis | 435/91 |
| 4,711,845 | 12/1987 | Gelfand et al. | 435/68 |
| 4,889,818 | 12/1989 | Gelfand et al. | 435/194 |

FOREIGN PATENT DOCUMENTS

WO92/06200 4/1992.
198864 8/1986 European Pat. Off.

OTHER PUBLICATIONS

Itakura et al., *Science*, vol. 198, 9 Dec. 1977, pp. 1056–1063.
Joyce et al., *J. Mol. Biol.*, (1985), 186:283–293.
Mullis et al., *Cold Spring Harbor Symp. Quant. Biol.* 51, 263 (1986).
Mullis and Faloona, *Methods Enzymol.* 155, 335 (1987).
Saiki et al., *Science* 239, 487 (1989).
Lawyer et al. *J. Biol. Chem.* 264, 6472–6437 (1989).
Longley et al., *Nuc. Acids Res.* 18, 7317–7322 (1990).
Blanco et al., *Gene* 100, 27–38 (1991).
Bernad et al., *Cell* 59, 219–228 (1989).
Holland et al., *Proc. Natl. Acad. Sci.* 88, 7276–7280 (1991).
Kelly and Joyce, *J. Mol. Biol.* 164, 529–560 (1983).
Barnes et al., *Gene* 112, 29–35 (1992).
Tindall and Kunkel, *Biochemistry* 27, 6008–6012 (1988).

Bolivar et al., *Gene* 2, 95–113 (1977).
Goeddel et al., *Nucleic Acids Res.* 8, 4057 (1980).
Shimatake et al., *Nature* 292, 129 (1981).
Broach, *Meth. Enz.* 101, 307 (1983).
Stinchcomb et al., *Nature* 282, 39 (1979).
Tschumper et al., *Gene* 10, 157–166 (1980).
Clarke et al., *Meth. Enz.* 101, 300 (1983).
Hess et al., *J. Adv. Enzyme Reg.* 7, 149 (1968).
Hitzemen et al., *J. Biol. Chem.* 255, 12073–12080 (1980).
Broach, *Gene* 8, 121–133 (1979).
Fiers et al., *Nature* 273, 113–120 (1978).
Depicker et al., *J. Mol. Appl. Gen.* 1, 561–573 (1982).
Miller et al., *Genetic Engineering* 8, 277–297 (Setlow et al., eds., Plenum Publishing 1986).
Cohen et al., *Proc. Natl. Acad. Sci.* (USA) 69, 2110–2114 (1972).
Holland et al., *J. Biol. Chem.* 256, 1385–1395 (1981).
Shaw et al., *Gene* 23, 315–330 (1983).
Graham and van der Eb, *Virology* 52, 456–467 (1973).
Van solingen et al., *J. Bact.* 130, 946–947 (1977).
Hsiao et al., *Proc. Natl. Acad. Sci.* (USA) 76, 3829–3833 (1979).
Maxam and Gilbert, *Methods in Enzymology* 65, 499–560 (1980).
Sanger et al., *Proc. Natl. Acad. Sci.* (USA) 74, 5463–5467 (1977).
Sanger, *Science* 214, 1205–1210 (1981).
Innis et al., *Proc. Natl. Acad. Sci.* 85, 9436–9440 (1988).
Tabor et al., *J. Biol. Chem.* 262, 16212–16223 (1987).
Wernette et al., *Biochem.* 27, 6046–6054 (1988).

*Primary Examiner*—Robert A. Wax
*Assistant Examiner*—Keith D. Hendricks
*Attorney, Agent, or Firm*—Banner & Allegretti, Ltd.

[57] ABSTRACT

Novel, modified Taq DNA polymerases and genes encoding for them are disclosed. The modified Taq DNA polymerases of the invention are the same size, have the same heat stability and synthesis rate as the native enzyme, but lack the 5'-3' exonuclease activity. As a result of this modification, the enzymes have improved processivity as compared to the native enzyme.

The enzymes of the present invention enable improved methods of conducting PCR, DNA sequencing, and DNA synthesis.

12 Claims, 8 Drawing Sheets

Restriction map of gene for Taq DNA polymerase

PCR Analysis of Processivity

MODIFIED THERMO-RESISTANT DNA POLYMERASES

This invention was made with the Government support under grant GM 24711 awarded by the National Institutes of Health. The Government has certain rights in the invention.

BACKGROUND OF THE INVENTION

1. Field of the Invention

This invention relates to the field molecular biology, specifically with reference to the subject of DNA polymerases for use in the polymerase chain reaction and DNA sequencing.

2. Description of the Prior Art

Polymerase Chain Reaction (PCR) was one of the most important inventions developed in area of biotechnology during the 1980's and has proven useful for a variety of tasks. *PCR Technology, Principles and Applications for DNA Amplification* (Erlich ed. 1989). The process provides a method for amplifying known specific nucleic acid sequences. Mullis, U.S. Pat. No. 4,683,202. The process comprises treating single- or double-stranded DNA containing the sequence of interest with an excess of two oligonucleotide primers sufficiently complementary of the strands so as to hybridize to the denatured strands. The hybridized primers are then extended by a DNA polymerase in the presence of the four dNTPs. The primer extension products are then separated and can serve as templates for another cycle of replication. The number of DNA templates approximately doubles on each cycle of amplification. Thus, 20 cycles of the process will result in approximately a $2^{20}$-fold amplification.

The original protocols for PCR used the Klenow fragment of *E. coli* DNA polymerase I to catalyze the extension of the oligonucleotide primers. Mullis et al., *Cold Spring Harbor Symp. Quant. Biol.* 51, 263 (1986); Mullis and Faloona, *Methods Enzymol.* 155, 335 (1987). The Klenow fragment proved somewhat cumbersome to use. Denaturation of the double stranded DNA at the start of each cycle requires temperatures ranging from 80° to 105° C. These temperatures inactivate the Klenow fragment. Consequently, fresh enzyme was required at the start of each new amplification cycle. While this process generally worked well for small segments of DNA (<200 bp), a host of problems arose when replication of larger fragments was attempted.

The difficulties associated with use of the Klenow fragment DNA polymerase were circumvented with the introduction of thermostable DNA polymerase obtained from the thermophilic bacterium *Thermus aquaticus* (Taq DNA polymerase). Saiki et al., *Science* 239, 487 (1989); Gelfand et al., U.S. Pat. No. 4,889,818. This enzyme has been cloned, overproduced, and the DNA sequence determined. Lawyer et al., *J. Biol. Chem.* 264, 6427–6437 (1989).

In addition to its DNA polymerase activity, Taq DNA polymerase also possesses 5'-3' polymerization-dependent exonuclease activity, but it lacks 3'-5' exonuclease activity. Longley et al., *Nuc. Acids Res.* 18, 7317–7322 (1990); Blanco et al., *Gene* 100, 27–38 (1991); Bernad et al., *Cell* 59, 219–228 (1989); Lawyer et al., supra; Holland et al., *Proc. Natl Acad. Sci.* 88, 7276–7280 (1991); and Kelly and Joyce, *J. Mol. Biol.* 164, 529–560 (1983). Studies have identified the 5'-3' exonuclease activity as being an intrinsic part of Taq DNA polymerase. Longely et al., supra; and Barnes et al., *Gene* 112, 29–35 (1992). This activity appears to facilitate a nick translation DNA reaction.

Native Taq DNA polymerase suffers from a high rate of misincorporation— about four times higher than that of the Klenow fragment of *E. coli* DNA polymerase I. It has been estimated that Taq DNA polymerase incorporates one incorrect nucleotide in 9000. Tindall and Kunkel, *Biochemistry* 27, 6008 (1988). After 20 amplification cycles, this would result in DNA molecules with random mutations averaging one in every 900 bases. Saiki et al., supra. If the PCR product is to be inserted into an expression vector, the chance that one cloned molecule will contain an unwanted sequence alteration may be significant. It would be desirable, therefore, to decrease the rate of misincorporation of the DNA polymerase used in PCR without sacrificing the heat stability and rate of synthesis of the native Taq DNA polymerase.

It has been shown that removal of the 5'-most 235 codons of the Taq DNA polymerase gene results in an expression product that has no 5'-3' exonuclease activity and a lower rate of mutagenesis. Tindall et al., supra; and Barnes, supra.

Other forms of Taq DNA polymerase are available. AmpliTaq™ is a commercially available genetically engineered version of Taq DNA polymerase and is substantially equivalent to the native form. Perkin Elmer Cetus; Saiki and Gelfand, *Amplifications* (Perkin Elmer Cetus), 1, 4 (1989). Also commercially available is a truncated gene product, the Stoffel fragment, that expresses an enzyme lacking the 5'-3' exonuclease activity and having much lower unit activity, probably due to decreased processivity and increased mutagenesis. Barnes, supra. Gelfand and Abramson (PCT International Publication No. WO 92/06200) disclosed a modified Taq polymerase having the same length as the native enzyme, but with highly attenuated 5'-3' exonuclease activity. The exonuclease activity is defeated by mutation in nucleotide 137 of the Taq polymerase gene, wherein the mutation is G to A, resulting in a change in amino acid 46 of the enzyme from Gly to Asp. This enzyme is reported as having the same polymerase activity, processivity and extension rate as the native enzyme.

SUMMARY OF THE INVENTION

An object of this invention is to enhance the synthesis activity of DNA polymerase as used in PCR and DNA sequencing.

The invention disclosed herein achieves this object by providing a modified Taq DNA polymerase and a correspondingly modified Taq DNA polymerase gene sequence. The modified Taq DNA polymerase is the same size, has the same heat stability and synthesis rate as the native enzyme, but the 5'-3' exonuclease activity is missing. As a result of this modification, the gene expression product has improved processivity.

The enzymes of the present invention enable improved methods of conducting PCR, DNA sequencing and DNA synthesis.

DETAILED DESCRIPTION OF THE INVENTION

As used herein, the term "replication product" refers to the oligonucleotides synthesized by DNA polymerase, whether it be as part of the polymerase chain reaction, DNA sequencing, or any other reaction where DNA polymerase is used to synthesize an oligonucleotide.

The term "oligonucleotide" as used herein is defined as a molecule composed of two or more deoxyribonucleotides or ribonucleotides.

The term "thermostable" refers to an enzyme that is stable to heat (>95° C.) and catalyzes combination of nucleotides to form an oligonucleotide. The term "thermo stability" as used herein refers to the characteristic stability of an enzyme to heat.

As used herein, the term "altered amino acid" means an amino acid that differs from that found in the native peptide or protein. Hence, if the native peptide has the amino acid Cys at position 43, and the modified peptide has the amino acid Gly at that position, Gly is the "altered amino acid." Similarly, the term "altered nucleotide" means a nucleotide that differs from that found in a native oligonucleotide, polynucleotide, gene, or other nucleotide fragment.

As used herein, the phrase "lacking 5'-3' exonuclease activity" means an enzyme having less than 1% of the 5'-3' exonuclease activity of the native Taq DNA polymerase.

Figure 2:
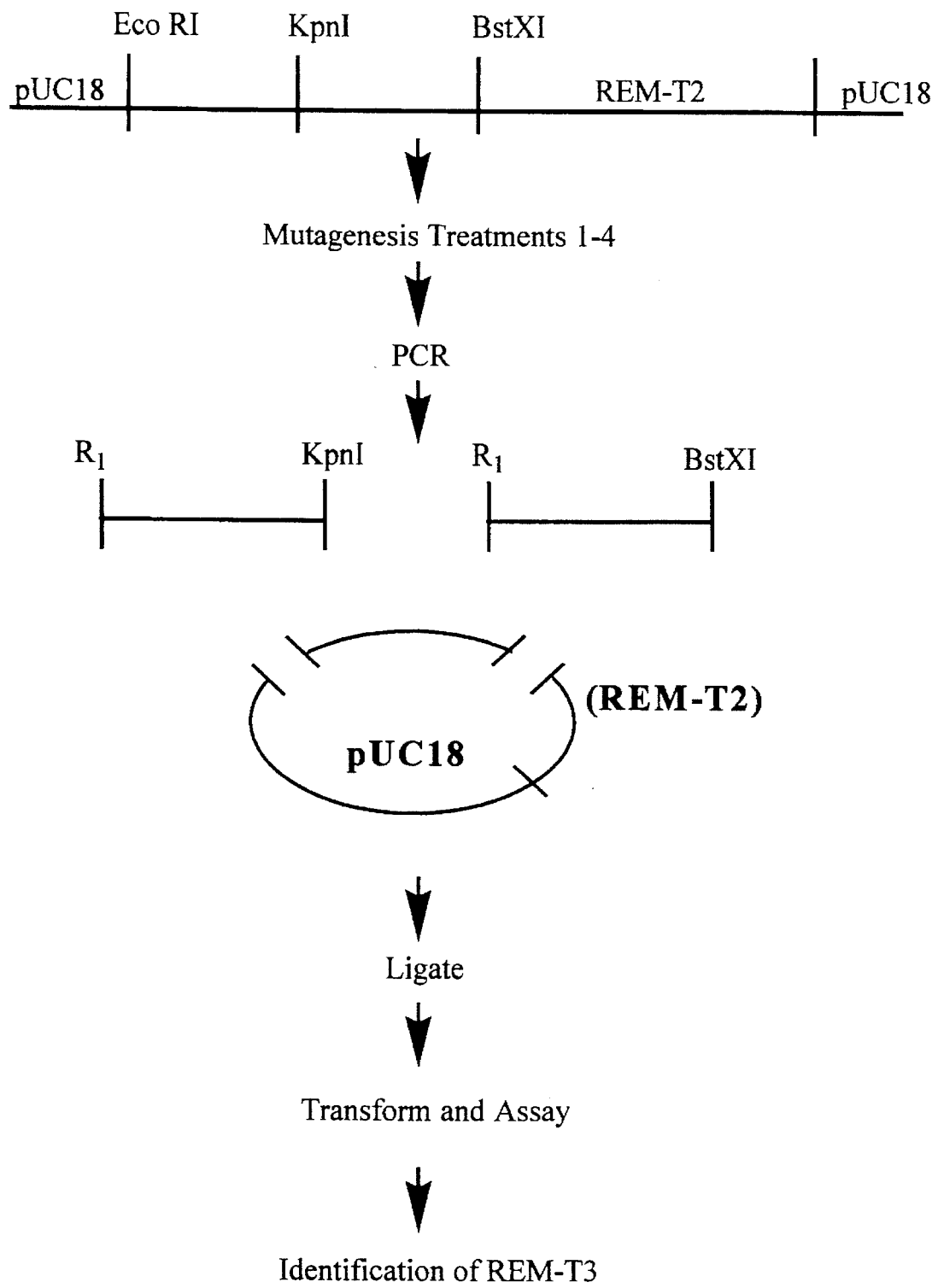
FIG. 2 is a graphical depiction of the method for producing the modified Taq DNA polymerase and the gene encoding it.

We undertook to inactivate the 5'-3' exonuclease activity of the Taq DNA polymerase by in vitro mutagenesis without removal of the portion of the gene encoding that activity. The procedure followed was to develop a method of "zone mutagenesis" for that region of the Taq DNA polymerase gene encoding for the 5'-3' exonuclease activity. See FIG. 2. Although the particular nucleotides encoding the amino acid residues required for 5'-3' exonuclease activity have not been clearly identified, earlier work suggested a region analogous to the the region involved in DNA polymerases from other bacteria. Kelly and Joyce, supra.

Figure 1:
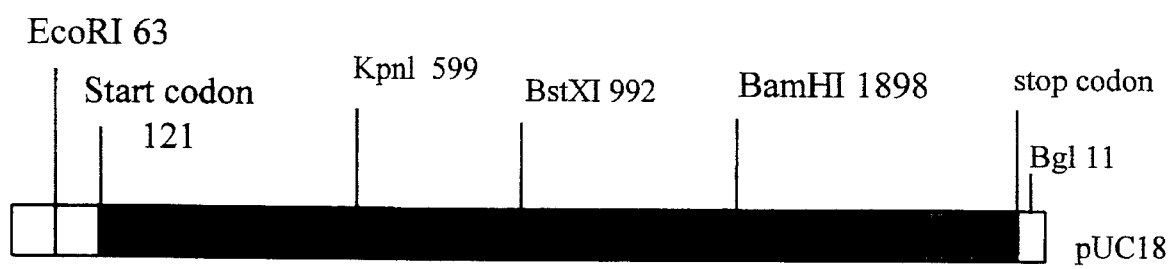
FIG. 1 is a graphical depiction of the restriction map of the Taq DNA polymerase gene.

To briefly summarize, using PCR technology we generated a Taq gene, which we cloned into the plasmid vector pUC18. See FIG. 1. The pUC18 plasmid containing the Taq gene is designated pLSM5 (SEQ ID NO: 3). Four base changes in the Taq gene were produced by PCR and cloned in pLSM5 (SEQ ID NO: 3) compared to the published Taq DNA polymerase gene sequence (available under the accession code "TTHTAQPIA" in GenBank) (SEQ ID NO: 1): 1) C to G at position 89 in the untranslated 5' end, 2) T to A at position 934 (Phe to Ile), 3) T to C at position 962 (Leu to Pro), and 4) G to A (resulting in no amino acid change) at position 2535. The protein expression product of this gene has an altered amino acid at positions 272 (Ile) and 281 (Pro). We then subjected the pLSM5 (SEQ ID NO: 3) plasmid to conditions that would cause the random mutations in the 5' exonuclease domain.

The vector encoding the Taq gene (pLSM5 (SEQ ID NO: 3) producing the enzyme REM-T2 (SEQ ID NO: 4)) begins at nucleotide 70 and ends at 2619. The reading frame for translation begins at nucleotide 121 and ends at 2619 by the convention of Lawyer et al., *J. Biol. Chem.* 264, 6427–6437 (1989).

The following sequence appears at the 5' junction between the pUC18 plasmid and the Taq gene:

. . . AATTTCACACAGGAAACAGCTATGAC-CATGATTACG<u>AA</u>TTCTAAA . . . (SEQ ID NO: 14)

This sequence begins with the pUC18 antisense nucleotide sequence 490 to 455. The underlined nucleotides (<u>AA</u>) were added to create a restriction site. The Taq gene sequence (bold face) begins at nucleotide 70).

The following sequence appears at the 3' junction between the pUC18 plasmid and the Taq gene:

. . . CAAGGAGTGA GATTCTCTAGAGTCGACCTGCAGGCATGCAAGC TTGGCACT GGCCGTCGTTTT . . . (SEQ ID NO: 15)

This sequence begins with Taq polymerase gene nucleotide 2610 to 2619. The underlined nucleotides (<u>GA</u>) were added to create a restriction site. The remaining sequence is the pUC18 antisense nucleotide, 413 to 381. Both junction sequences have been verified by sequence analysis.

The enzyme expression product of the pLSM5 plasmid, REM-T2 (SEQ ID NO: 4), has substantially the same processivity, 5'-3' exonuclease activity, and performance in normal PCR, to the extent tested so far, as the commercially available Taq DNA polymerase AmpliTaq™.

A variety of methods of mutagenesis are known to those of skill in the art and may be used in preparing a modified Taq DNA polymerase gene according to the present invention. See, e.g., Sambrook et al., *Molecular Cloning: A Laboratory Manual* (Cold Spring Harbor Laboratory Press, 2d Ed. 1989). These include, for example, site-directed mutagenesis using single-stranded cloned isolates of the nucleotide sequence to be mutated by annealing and extension of a homologous primer containing the desired mutation, followed by re-introduction and selection in bacteria. Also within the skill of one of ordinary skill in this art is the use of numerous PCR-based protocols, for introducing mutations either in a site-specific or random fashion. In the instant invention, genes mutated using such techniques were thereafter treated with restriction endonucleases that cut in the region believed to be responsible for 5'-3' exonuclease activity, thereby producing mutated inserts coding for that portion of the gene. A vector containing the native Taq DNA polymerase gene was treated with the same endonucleases and the previously-isolated mutant inserts ligated into the vector. Cells were transformed with the vector containing the inserts and colonies grown. We assayed polymerases expressed by the various colonies for polymerase activity as well as 5'-3' exonuclease activity. The cells transfected with the gene encoding the modified Taq DNA polymerase meeting the objective of the present invention were thereby identified.

Appropriate host cells for the present invention may be chosen from the prokaryote group, which most frequently are represented by various strains of *E. coli*. Other microbial strains such as bacilli may be used, however. *Bacillus subtilis* and various species of Pseudomonas may be used, for example. In such prokaryotic systems, plasmid vectors that contain replication sites and control sequences derived from a species compatible with the host are used. For example, *E. coli* is typically transformed using derivatives of pBR322, a plasmid derived from an *E. coli* species by Bolivar, et al., *Gene* 2, 95 (1977). pBR322 contains genes for ampicillin and tetracycline resistance, and thus provides addition markers that can be either retained or destroyed in constructing the desired vector. Commonly used prokaryotic control sequences, which are defined herein to include promoters for transcription initiation, optionally with an operator, along with ribosome binding site sequence, include such commonly used promoters as the g-lactamase (penicillinase) and lactose (lac) promoter systems (Chang, et al., *Nature* 198, 1056 (1977)), the tryptophan (trp) promoter system (Goeddel, et al., *Nucleic Acids Res.* 8, 4057 (1980)), the lambda-derived PL promoter (Shimatake et al., *Nature* 292, 129 (1981)), and the N-gene ribosome binding site, which has been made useful as a portable control cassette (U.S. Pat. No. 4,711,845). The N-gene ribosome binding site comprises a first DNA sequence that is the PL promoter operably linked to a second DNA sequence corresponding to NRBS upstream of a third DNA sequence having at least one restriction site that permits cleavage within six bp 3' of the NRBS sequence. Also useful is the phosphatase A (phoA) system described by Chang et al. in European Patent Publication No. 196,864 published Oct. 8, 1986. Any available promoter system compatible with prokaryotes can be used, however.

In addition to bacteria, eucaryotic microbes, such as yeast, may also be used as hosts. Laboratory strains of *Saccharomyces cerevisiae*, Baker's yeast, are most used, although a number of other strains are commonly available. While vectors employing the 2 micron origin of replication are illustrated (Brach, *Meth. Enz.* 101, 307 (1983)), other plasmid vectors suitable for yeast expression are known (see, e.g., Stinchcomb et al., *Nature* 282, 39 (1979), Tschempe et al., *Gene* 10, 157 (1980), and Clarke et al., *Meth. Enz.* 101, 300 (1983). Control sequences for yeast vectors include promoters for the synthesis of glycolytic enzymes. Hess et al., *J. Adv. Enzyme Reg.* 7, 149 (1968) and Holland et al., *Biotechnology* 17, 4900 (1978).

Additional promoters known in the art include the promoter for 3-phosphoglycerate kinase (Hitzeman et al., *J. Biol. Chem.* 255, 2073 (1980)) and those for other glycolytic enzymes, such as glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters that have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization. Holland, supra.

It is also believed that terminator sequences are desirable at the 3' end of the coding sequences. Such terminators are found in the 3' untranslated region following the coding sequences in yeast-derived genes. Many of the vectors illustrated contain control sequences derived from the enolase gene containing plasmid peno46 (Holland et al., *J. Biol. Chem.* 256, 1385 (1981) or the LEU2 gene obtained from YEp13 (Broach et al., *Gene* 8, 121 (1978). Any vector containing a yeast-compatible promoter, origin of replication, and other control sequence is suitable, however.

It is also possible to express genes encoding polypeptides in eucaryotic host cell cultures derived from multicellular organisms. See, e.g., *Tissue Culture* (Cruz and Patterson eds., Academic Press 1973). Useful host cell lines include murine myelomas N51, VERO and HeLa cells, and Chinese Hamster Ovary (CHO) cells. Expression vectors for such cells ordinarily include promoters and control sequences compatible with mammalian cells such as the commonly used early and late promoters from Simian Virus 40 (SV 40) (Fiefs et al., *Nature* 273, 113 (1978)) or other viral promoters such as those derived from polyoma, Adenovirus 2, bovine papilloma virus, or avian sarcoma viruses, or immunoglobulin promoters and heat shock promoters. A system for expressing DNA in mammalian systems using the BPV as a vector is disclosed in U.S. Pat. No. 4,419,446. A modification of this system is described in U.S. Pat. No. 4,601,978. General aspects of mammalian cell host system transformations have been described by Axel, U.S. Pat. No. 4,399,216. It now appears that "enhancer" regions are important in optimizing expression. These generally are sequences found upstream of the promoter region. Origins of replication may be obtained from viral sources. Integration into the chromosome, however, is a common mechanism for DNA replication in eucaryotes.

Plant cells are also now available as hosts. Control sequences compatible with plant cells such as the nopaline synthase promoter and polyadenylation signal sequence are available. Depicker et al., *J. Mol. Appl. Gen.* 1, 561 (1982).

In addition, expression systems employing insect cells utilizing the control systems provided by baculovirus vectors have been described. Miller et al, *Genetic Engineering* 8, 277–297 (Setlow et al. eds. Plenum Publishing 1986). These systems are also successful in producing Taq DNA polymerase.

Cells transformed with the modified Taq DNA polymerase gene may be grown using any suitable technique. The appropriate technique will depend on the cell type and will be known to those skilled in the art.

Depending on the host cell used, transformation is done using standard techniques appropriate to such cells. The treatment employing calcium chloride is used for prokaryotes or other cells that contain substantial cell wall barriers. Cohen, *Proc. Natl. Acad. Sci.* (USA)69, 2110 (1972). Infection with *Agrobacterium tumefaciens* is used for certain plant cells. Shaw et al. *Gene* 23, 315 (1983). For mammalian cells without such cell walls, the calcium phosphate precipitation method of Graham and van der Eb is preferred. *Virology* 52, 546 (1978). Transformations into yeast are carried out according to the method of Van solingen et al., *J. Bact.* 130, 946 (1977) and Hsiao et al., *Proc. Natl. Acad. Sci.* (USA) 76, 3829 (1979).

Construction of suitable vectors containing the desired coding and control sequences employs standard ligation and restriction techniques that are well understood in the art. Isolated plasmids, DNA sequences, or synthesized oligonucleotides are cleaved, tailored, and relegated in the form desired.

Site-specific DNA cleavage is performed by treating with the suitable restriction enzyme (or enzymes) under conditions that are generally understood in the art, and the particulars of which are specified by the manufacturer of these commercially available restriction enzymes. See, e.g., *New England Biolabs, Product Catalog*. In general, about 1 μg of plasmid or DNA sequence is cleaved by one unit of enzyme in about 20 μl of buffer solution. Often excess of restriction enzyme is used to ensure complete digestion of the DNA substrate. Incubation times of about one hour to two hours at about 37° C. are workable, although variations are tolerable. After each incubation, protein is removed by extraction with phenol/chloroform, and may be followed by ether extraction. The nucleic acid may be recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* 65, 499–560 (1980).

Cells producing Taq polymerase enyme of the desired type can be identified by standard techniques for assaying DNA polymerase and 5'-3' exonuclease activity. Id. Using some of these methods, we were able to isolate a Taq DNA polymerase having the same size, heat stability, and synthetic activity of native Taq DNA polymerase, but having increased processivity and resulting in decreased mutagenesis of PCR DNA products. See examples infra.

The modified Taq DNA polymerase of the present invention was chosen from a colony producing the enzyme with a relatively high polymerase activity and low 5'-3' exonuclease activity. We designated this product REM-T3 (SEQ ID NO: 6). An equivalent independently isolated product with a different mutation but equivalent properties is designated REM-T5 (SEQ ID NO: 8).

In addition to the modifications of native Taq DNA polymerase present in the modified Taq DNA polymerase of the present invention, individual amino acid residues in the peptide chain comprising the Taq DNA polymerase may be modified or deleted without eliminating any of the requisite properties described herein. Such alterations that do not destroy activity do not remove the DNA sequence or the modified Taq DNA polymerase from the contemplated scope of the present invention.

In order to assay the modified Taq DNA polymerase, REM-T3 (SEQ ID NO: 6), it was necessary to isolate it. We used the following novel, short isolation technique producing high purity enzyme quickly. Bacteria were grown overnight or to an OD at 600 nm of about 2.0 to 2.5 and then centrifuged at 5000 rpm for 10 minutes. The supernatant was discarded and the pellet washed with a solution of 50 mM Tris(8.0), 50 M dextrose, and 1 mM EDTA (15×cell wt). The pellet was re suspended and lysed with a solution of 50 mM Tris, 50 mM dextrose, 1 mM EDTA, and 1 mg/ml lysozyme(5×cell wt). An equal volume of a solution of 10 mM Tris and 50 mM KCl, and 1 mM EDTA was added and the resulting mixture incubated at 75° C. for 60 min before centrifuging at 8000 rpm for 15 min. The pellet was discarded and an equal volume of DEAE and 0.4 M $KPO_4$ (6.8) was added to the supernatant. The mixture was then incubated at 0° C. for 30 min and then centrifuged at 10,000 rpm for 20 min. The pellet was discarded and the supernatant put on a phosphocellulose column with 0.02 M $KPO_4$ (7.5)(4× cell wt). The column was eluted with a gradient of 0.02 to 0.4 M $KPO_4$ (7.5). The peak was collected and applied to a Bio Rex-70 column with a solution of 0.02 M $KPO_4$ (7.6), 80 mM KCl 5%, glycerol, 0.5% Tween, and 0.5% Nonidet P-40. This column was then eluted with a step gradient of 0.3 M KCl and the peak collected.

The thermostability of the modified Taq DNA polymerase of the present invention must be substantially equivalent to that of native Taq DNA polymerase, i.e., it must not become irreversibly denatured (inactivated) when subjected to the elevated temperatures for the time necessary to effect denaturation of double-stranded nucleic acids. The heating conditions (e.g., temperature and time) necessary for denaturation will depend on a variety of factors, including the buffer salt concentration and the length and composition of the nucleotide chain. Typically, the temperature range for which the enzyme must be stable is about 90 to about 105° C. for about 0.5 to four minutes. These values may vary depending on the conditions.

The modified Taq DNA polymerase of the present invention preferably functions optimally at temperatures above 40° C. The enzymes of the present invention is active in the temperature range 55°–95° C., and preferably in the range 70°–95° C.

U.S. Pat. No. 4,889,818 discloses and claims a native form of Taq DNA polymerase. Because the modified Taq DNA polymerase of the present invention retains all the characteristics of the native form that are useful in PCR technology, its use in PCR is preferable to the native form. Consequently, applications using Taq DNA polymerase as described in U.S. Pat. No. 4,889,818, col. 14, 1.33 to col. 27, 1. 27 may also use the modified Taq DNA polymerase of the present invention. Accordingly, the disclosure of U.S. Pat. No. 4,889,818 is hereby incorporated by reference.

Besides use in the polymerase chain reaction, the modified Taq DNA polymerase of the present invention can be used in DNA sequencing by, for example, the Sanger dideoxy-mediated chain-termination method. Sanger et al., *Proc. Natl. Acad. Sci.* 74, 5463 (1977). Other similar uses will be known to those of skill in the art.

The following examples further elucidate the present invention, but are not intended to limit it.

EXAMPLE 1

Zone Mutagenesis of the Taq DNA Polymerase Gene—Treatment 1

The Taq polymerase gene was amplified from genomic DNA (*Thermus aquaticus*) using primers adding an EcoRI site in the 5' UTR (nucleotide 70) and BglII site at the 3' end (nucleotide 2619). The PCR product was cloned into pUC18 after digesting the vector with EcoRI and BamHI. See FIG. 1. We designated this Taq gene REM-T2. We then incubated the plasmid containing the Taq gene at pH 4.8 (10 mM sodium acetate) and room temperature for 20 minutes followed by neutralization to pH 8.0 with 50 mM Tris HCl. Inserts for the putative amine terminal region of the gene were generated by PCR using the "reverse primer" for pUC18 (CAG GAA ACA GCT ATG ACC (SEQ ID NO: 11) and the "sequencing primer" 628A (CCC AAA GCC AGG CCG (SEQ ID NO: 12)) followed by digestion with Eco RI and KpnI.

The pLSM5 (SEQ ID NO: 3) vector was digested with EcoRI and KpnI and purified. The inserts previously generated were then inserted into this vector. Ligation for insertion of the modified Taq gene was followed by transformation of DH5a cells followed by growth of individual colonies with assay for the DNA polymerase activity and the 5'-3' exonuclease activity.

EXAMPLE 2

Zone Mutagenesis of the Taq DNA Polymerase Gene—Treatment 2

Using PCR, we generated a Taq gene (REM-T2), which we cloned into the plasmid vector pUC18. See FIG. 1. We incubated the plasmid DNA containing the Taq gene at pH 4.8 and 60° C. for 5 minutes followed by neutralization to pH 8.0 with 50 mM Tris HCl. Inserts for the putative amine terminal region of the gene were generated by PCR using the "reverse primer" for pUC18 (CAG GAA ACA GCT ATG ACC (SEQ ID NO: 11)) and the "sequencing primer" 628A (CCC AAA GCC AGG CCG (SEQ ID NO: 12)) followed by digestion with Eco RI and KpnI.

A vector encoding the Taq gene (pLSM5 (SEQ ID NO: 3) producing the enzyme REM-T2 (SEQ ID NO: 4)) was digested with Eco RI and KpnI and purified. The inserts previously generated were then inserted into this vector. Ligation for insertion of the modified Taq gene was followed by transformation of DH5a cells followed by growth of individual colonies with assay for the DNA polymerase activity and the 5'-3' exonuclease activity.

EXAMPLE 3

Zone Mutagenesis of the Taq DNA Polymerase Gene—Treatment 3

Using PCR, we generated a Taq gene (REM-T2), which we cloned into the plasmid vector pUC18. See FIG. 1. We amplified the N-terminal region of the Taq DNA polymerase gene for three consecutive PCR programs of 30 cycles each using the "reverse primer" for pUC18 (CAG GAA ACA GCT ATG ACC) and the "sequencing primer" 628A (CCC AAA GCC AGG CCG (SEQ ID NO: 12)). Inserts for the putative amino terminal region of the gene were generated by digestion of the PCR products with Eco RI and KpnI.

A vector encoding the Taq gene (pLSM5 (SEQ ID NO: 3) producing the enzyme REM-T2 (SEQ ID NO: 4)) was digested with Eco RI and KpnI and purified. The inserts previously generated were then inserted into this vector. Ligation for insertion of the modified Taq gene was followed by transformation of DH5a cells followed by growth of individual colonies with assay for the DNA polymerase activity and the 5'-3' exonuclease activity.

EXAMPLE 4

Zone Mutagenesis of the Taq DNA Polymerase Gene—Treatment 4

Using PCR, we generated a Taq gene (REM-T2), which we cloned into the plasmid vector pUC18. See FIG. 1. We incubated the plasmid DNA containing the Taq gene a pH 4.8 and 70° C. for 15 minutes followed by neutralization to pH 8 with 50 mM Tris HCl. Inserts for the putative amino terminal region of the gene were generated by PCR using the "reverse primer" for pUC18 (CAG GAA ACA GCT ATG ACC (SEQ ID NO: 11)) and the "sequencing primer" 1155A (CAG GTC CCT GAG GGC (SEQ ID NO: 13)) and 5× concentration of dNTPs (0.75 mM) followed by digestion with Eco RI and BstXI.

A vector encoding the Taq gene (pLSM5 (SEQ ID NO: 3) producing the enzyme REM-T2 (SEQ ID NO: 4)) was digested with Eco RI and BstXI and purified. The inserts previously generated were then inserted into this vector. Ligation for insertion of the modified Taq gene was followed by transformation of DH5a cells followed by growth of individual colonies with assay for the DNA polymerase activity and the 5'-3' exonuclease activity.

EXAMPLE 5

DNA Polymerase Activity Assay

Assay mixture:
reaction volume: 0.3 ml
25 mM Tris-HCl (pH=8.8)
4 mM MgCl$_2$
22 µg activated ssDNA (salmon sperm)
0.033 mM dNTP (each)
2 µCi [methyl-$^3$H] thymidine 5' triphosphate
enzyme
Assay procedure:
The mixture was incubated at 75° C. for 10 minutes. The reaction was stopped with 2 ml ice cold 10% TCA—0.1 M sodium pyrophosphate. The tubes were then placed on ice for 10 minutes and the reaction volume filtered. The tube and filter were washed three times with 2 ml of 10% TCA—0.1 M sodium pyrophosphate. The filter was then washed with 10 ml 0.01 N HCl. Next the filters were dried at 120° C. for 15 minutes. The dried filters were counted in 1 ml of Scintiverse.

The results are displayed in Table 1, infra.

EXAMPLE 6

5'-3' Exonuclease Activity Assay

Preparation of double stranded substrate with blunt ends and removal of 5' phosphate A Blue-Script plasmid was cut with HincII to produce one double stranded piece with blunt ends and treated with CIP (calf intestine phosphatase) to remove the 5' phosphate.

End-labeling of the 5' ends using [γ-$^{32}$P]ATP

8 µl plasmid and 4 µl buffer were mixed with spermidine and 28 µl distilled H$_2$O. The mixture was then heated to 70° C. for 5 minutes and then chilled on ice for 2 minutes. 10 µl kinase buffer with 1 µl[γ-$^{32}$P]ATP (about 10 µµCi) and 2 µl ( 20 units) of T4 polynucleotide kinase were added. Then the mixture was incubated for 30 minutes at 37° C. The reaction was stopped by adding 2 gl 0.5 M EDTA. The enzyme was inactivated by incubating for 10 minutes at 70° C. The radioactive ATP was removed by washing 4 times (2 ml each) in Centricon 100. The final volume was about 50 µl (38,000 cpm/µl).

5'-3' exonuclease assay

Assay conditions:
reaction volume 50
25 mM Tris HCl (8.8)
4 mM Mg Cl$_2$
0.5–1 µl labeled substrate
0.3 units of DNA polymerase
Samples were incubated at 50°–55° C. for 15, 30 or 60 minutes. The reaction was stopped with 0.3 ml 10% TCA. The sample was microfuged for 15 minutes at 4° C. 0.1 ml was sampled on filter paper. The filter paper was dried at 120° C. for 15 minutes. Dried filters were counted in 1 ml of Scintiverse.

The assay results are presented in Table 1, infra.

EXAMPLE 7

Sequencing Mutant Genes

Figure 3:
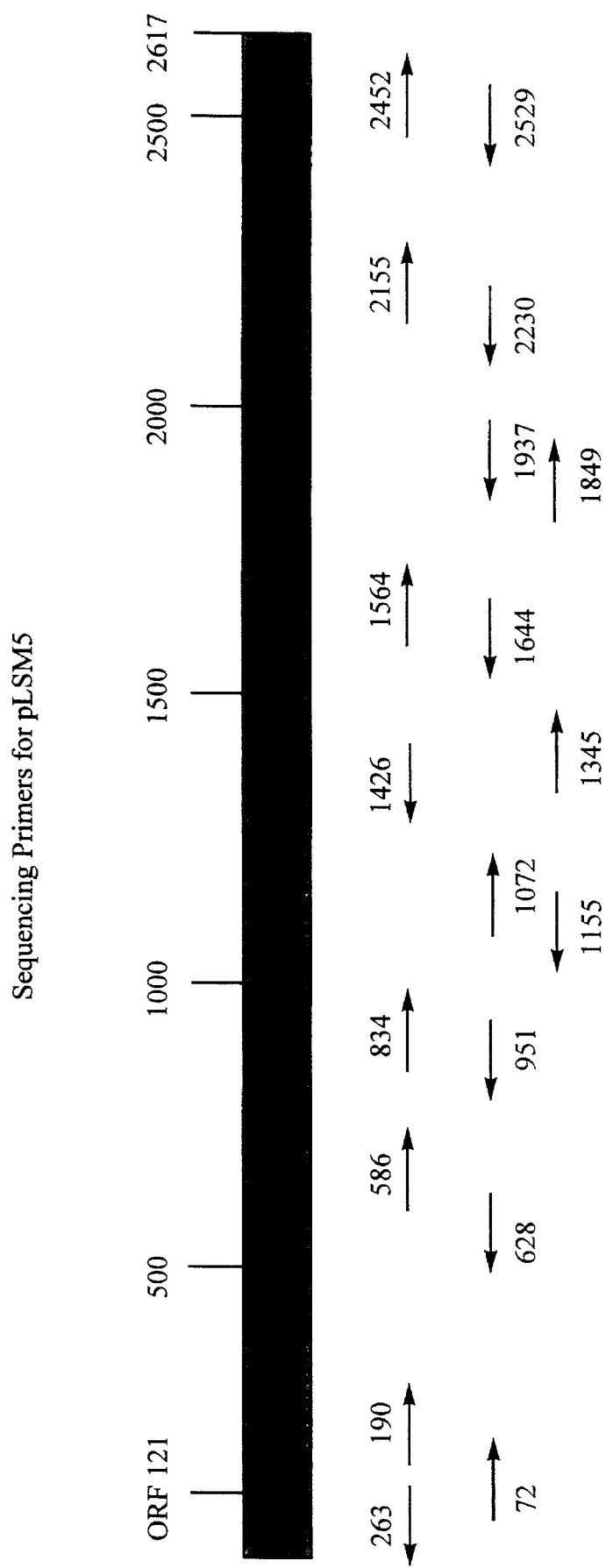
FIG. 3 shows the sequencing primers for the pLSM5 (SEQ ID NO: 3) plasmid.

Three mutants were chosen from those listed in Table 1 for low exonuclease activity. These were colony 18' (the plasmid of which we designate pTarf2 (SEQ ID NO: 9)) and colony 20' (the plasmid of which we designate pTarf3 (SEQ ID NO: 5)). A third mutant, pTarf5 (SEQ ID NO: 7), was obtained in a similar manner as in Example 4. pTarf3 (SEQ ID NO: 5) produces REM-T3 (SEQ ID NO: 6) and pTarf5 (SEQ ID NO: 7) produces REM-T5 (SEQ ID NO: 8). Bi-directional sequencing of the nucleic acid sequence of these mutants was conducted in the following manner: DNA sequence analysis was performed on alkaline-denatured double stranded plasmids. We used synthesized oligonucleotide primers (FIG. 3), [α-$^{35}$S]-dATP, and Sequenase® T7 DNA polymerase kit (United States Biochemical Corp.) according to the manufacturer's conditions. This method is based on the dideoxy chain termination reaction (Sanger, *Science* 214, 1205 (1981)).

The alterations found in the mutants are presented in Table 2. These alterations are of the pLSM5 (SEQ ID NO: 3) sequence, i.e., the pTarf2 (SEQ ID NO: 9), pTarf3 (SEQ ID NO: 5), and pTarf5 (SEQ ID NO: 7) sequences are the same as the pLSM5 (SEQ ID NO: 3) sequence except for the alterations listed in Table 2.

TABLE 1

Enzyme Activity Of New Taq Clones

| treatment | colony | polymerase act units/µl | 5'-3' exonuclease activity % of REM-T2 (SEQ ID NO: 4) |
|---|---|---|---|
| 1 | 1 | 0.132 | 87 |
|   | 2 | 0.503 | 97 |
|   | 3 | 0.053 | 14 |
|   | 4 | 0.27 | 88 |
|   | 5 | 0.098 | 82 |
|   | 6 | 0.41 | 94 |
|   | 7 | 0.255 | 95 |
| 2 | 8 | 0.106 | 74 |
| 1 | 1' | 1.54 | 104 |
|   | 2' | 1.60 | 94 |
|   | 3' | 1.06 | 105 |
|   | 4' | 1.49 | 100 |
|   | 5' | 1.06 | 104 |
|   | 6' | 2.20 | 114 |
|   | 7' | 0.35 | 107 |
|   | 8' | 0.68 | 117 |
|   | 9' | 0.74 | 94 |
|   | 10' | 0.87 | 109 |
| 2 | 11' | 1.81 | 98 |
|   | 12' | 1.22 | 95 |
|   | 13' | 1.68 | 110 |
|   | 14' | 1.04 | 102 |
|   | 15' | 0.84 | 101 |
|   | 16' | 1.4 | 98 |
|   | 17' | 0.15 | 104 |
|   | 18' | 1.77 | 24 |
|   | 19' | 1.11 | 107 |
| 3 | 20' | 1.73 | 0 |
|   | 21' | 0.018 | 6 |
|   | 22' | 0.48 | 0 |
|   | 23' | 1.8 | 105 |
|   | 24' | 0.83 | 94 |
|   | 25' | 0.78 | 93 |

1 unit of polymerase activity=10 nmoles of total nucleotides incorporated into acid insoluble form in 30 minutes at 75° C. Primed and unprimed colonies were obtained from cells transformed on different days.

TABLE 2

Alterations Relative to pLSM5 (SEQ ID NO: 3)

| plasmid | nucleotide position | amino acid position | codon change | amino acid change |
|---|---|---|---|---|
| pTarf2 (SEQ ID NO: 9) | 337 | 73 | TTC—CTC | Phe—Leu |
| pTarf3 (SEQ ID NO: 5) | 193 | 25 | CGC—TGC | Arg—Cys |
|  | 504 | 128 | AAG—AAA | Lys—Lys |
| pTarf5 (SEQ ID NO: 7) | 341 | 74 | CGC—CAC | Arg—His |

EXAMPLE 8

Improved Processivity of the Modified Taq Polymerase

Processivity of DNA synthesis by the modified Taq DNA polymerase (REM-T3) was assessed by several trials, with comparison to commercial enzymes and REM-T2. The method using the PCR protocol is novel.

Trial 1: Gel analysis of processivity by thermal stable DNA polymerases.

M13mp18 template (0.25 pmol/10 µl) and 5'$^{32}$P-labeled 17-mer (M13/pUC-40, BioLabs) (0.50 pmol/10 µl) (calculated $t_m$=52° C.) were annealed in 40 µl of 10 mM Tris-HCl (pH 8.0), and 5 mM MgCl$_2$. The mixture was incubated for 3 minutes at 90° C., 20 minutes at 42° C., and 15 minutes at room temperature. The reaction mixture was adjusted to 200 µM each of dNTP, 0.05% Tween 20 and Nonidet P-40, 10 mM Tris-HCl (pH 8.0), 50 mM KCl and 2.5 mM MgCl$_2$, in a total volume of 80 µl, then incubated at 55° C. for 2 minutes without enzyme. Next, 0.94 units of enzyme (AmpliTaq™ (Cetus), Stoffel Fragment(Cetus), REM-T2 or REM-T3)/10 µl were added to start the reaction. Five µl aliquots were removed from the reaction mixture at 0, 15, 30, 45 seconds, and 1, 2, and 5 minutes and added to 5 µl of stop solution (1 mg/ml each of xylene cyanol and bromphenol blue, 10 mM EDTA in formamide). For gel analysis, 5 µl were loaded onto a 6% wedge acrylamide/urea gel.

Figure 4:
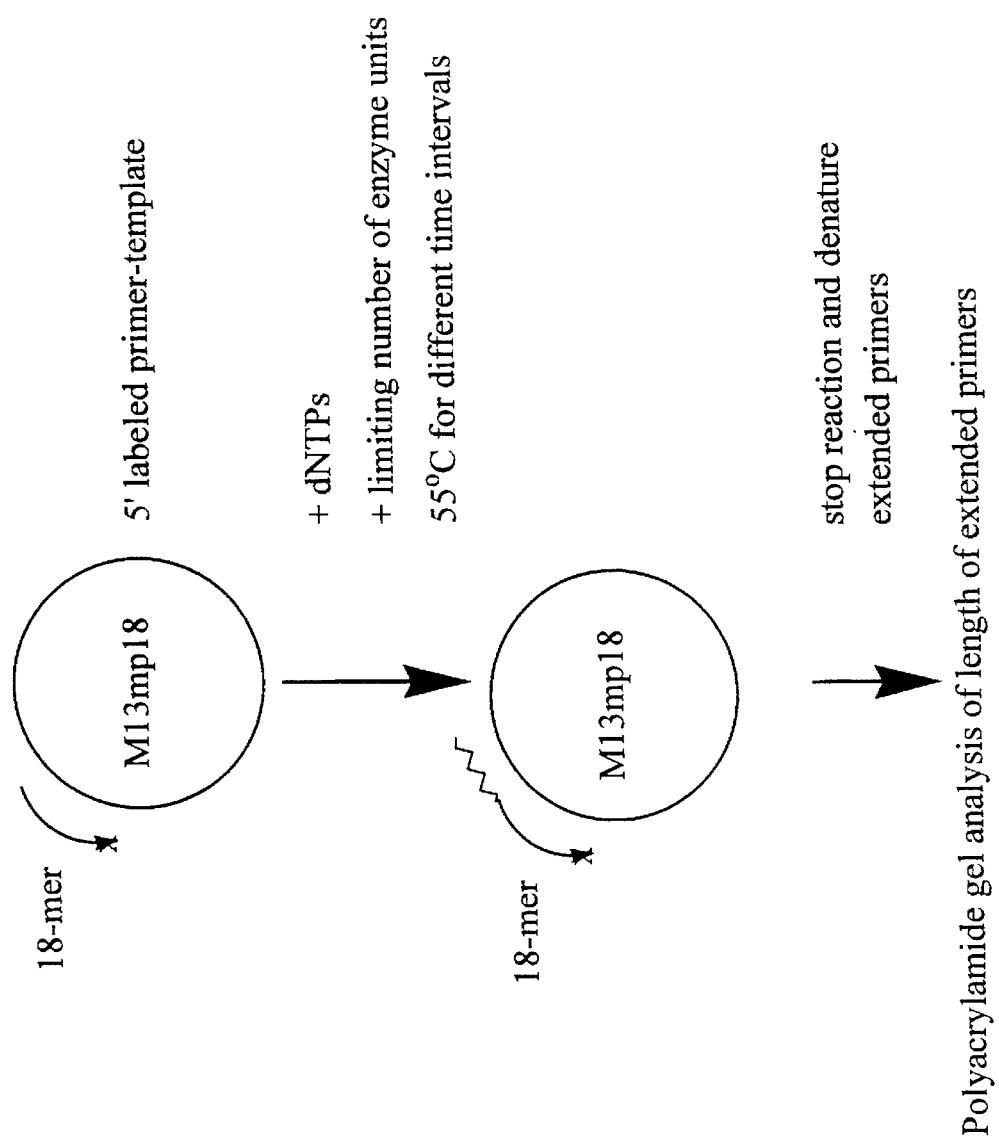
FIG. 4 is a schematic depiction of the method for testing processivity used in trials 1 and 2.
Figure 5:
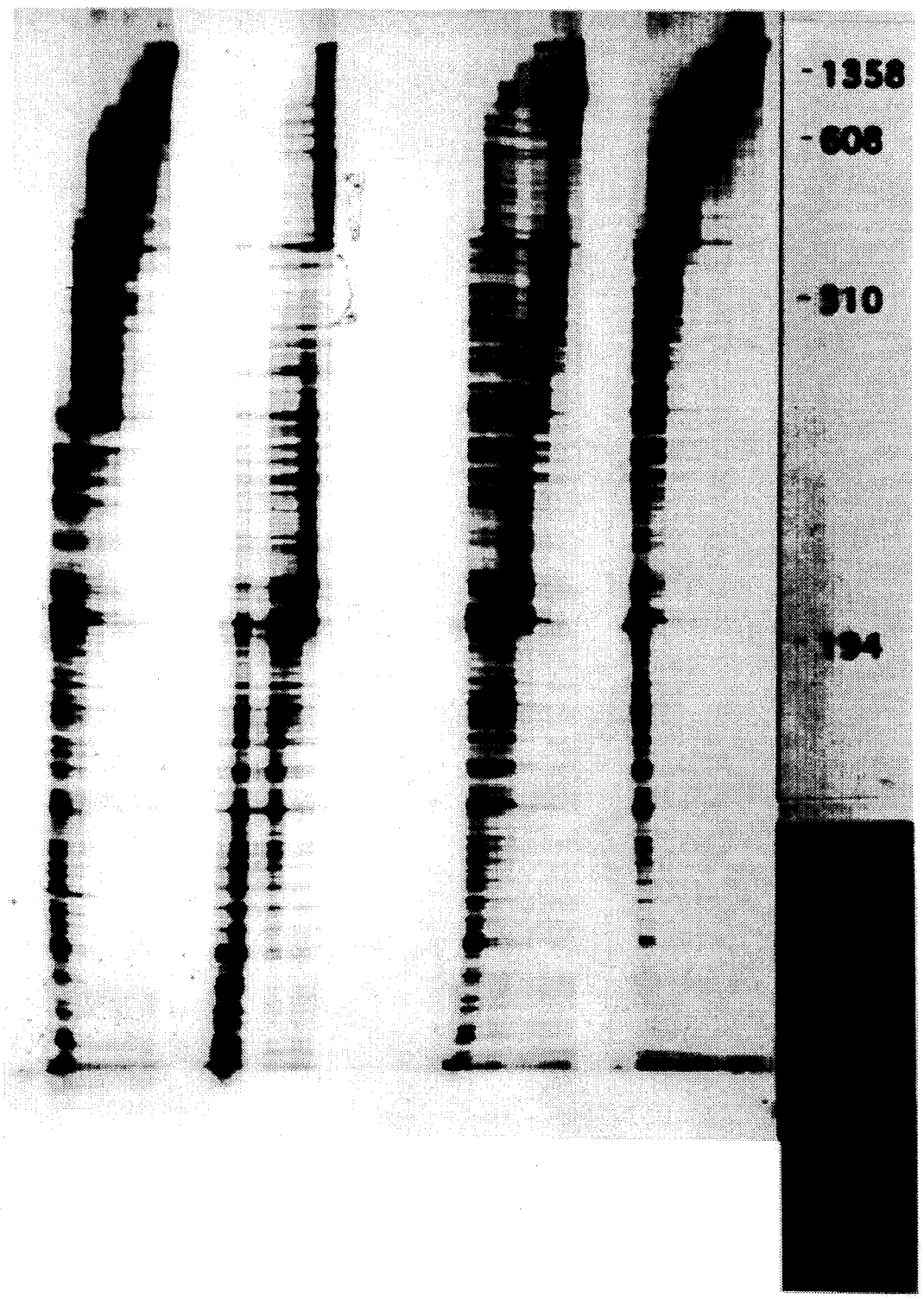
FIG. 5 is the autoradiograph showing the results of processivity testing used in trial 1.

FIG. 4 is a schematic depiction of the process and FIG. 5 is an autoradiograph showing the results of trial 1.

Trial 2: Gel analysis of processivity by thermal stable DNA polymerases.

The same method was used as in Trial 1, except 0.22 units of polymerase/10 µl of reaction mixture were added. In addition, smaller volumes were used for annealing (25 µl) and reaction mixture (50 µl).

For trials 1 and 2, the assayed polymerase activity of the AmpliTaq™ was lower than usual. It appears from the gels that the number of actual units of AmpliTaq™ used in the reaction may have been higher that estimated and, therefore, may not be comparable to the other reactions.

Figure 6:
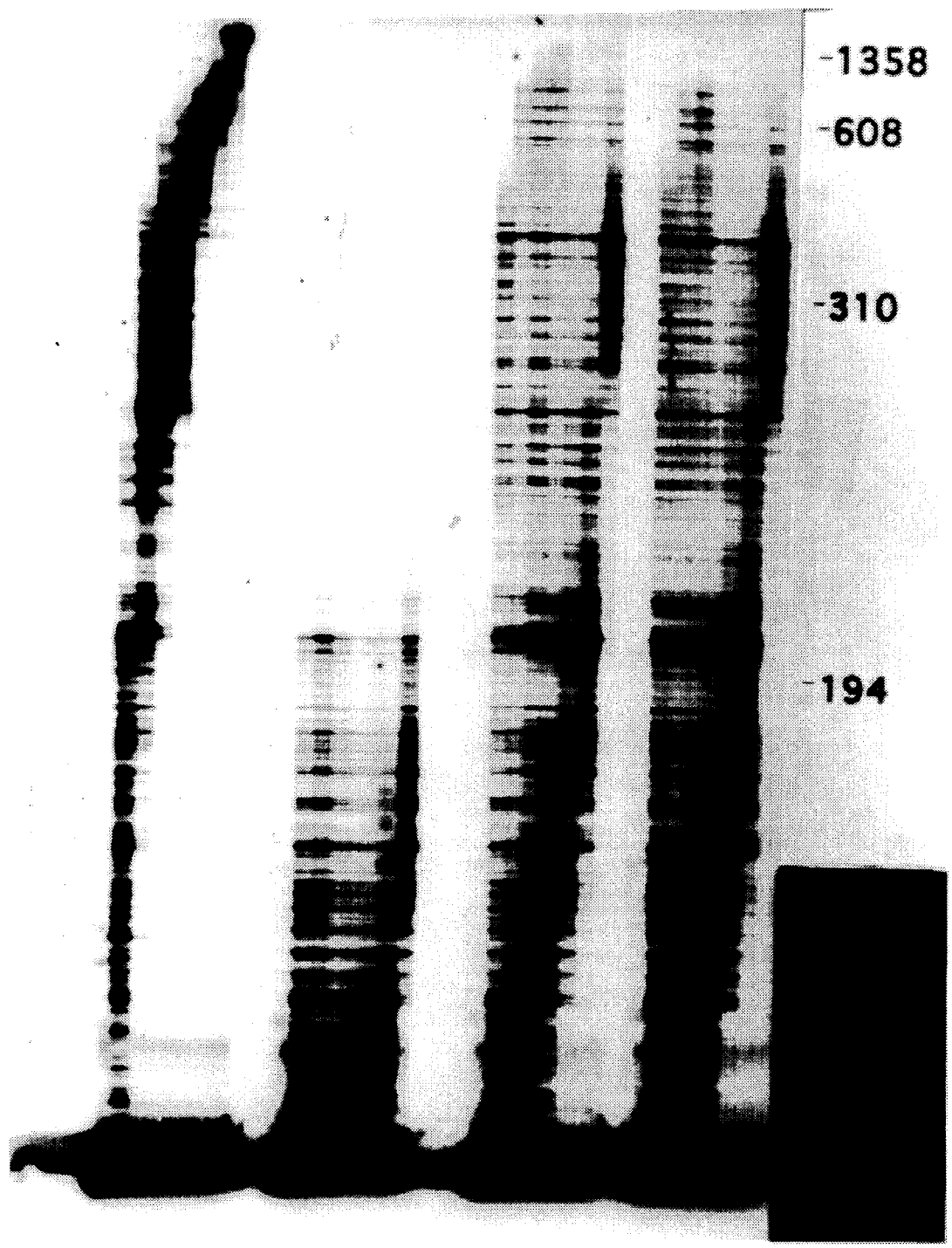
FIG. 6 is the autoradiograph showing the results of processivity testing used in trial 2.

FIG. 6 shows the results of trial 2. Note that when the amount of polymerase is limiting, REM-T2 (SEQ ID NO: 4) and REM-T3 (SEQ ID NO: 6) have processivities greater than that of the Stoffel fragment.

Trial 3: PCR analysis of processitivity by thermal stable DNA polymerases

The final volume of PCR reaction was 50 µl. The buffer contained 67 mM Tris-HCl (pH 8.8), 16 mM (NH$_4$)$_2$SO$_4$, 10 mM beta mercaptoethanol, 2 mM MgCl$_2$, 6.7 µM EDTA, and 150 µM each dNTP. There was an excess of template (0.02 pmol/10 µl) and primers (each 10 pmol/10 µl) over enzyme (0.04 units of polymerase/10 1) for each PCR reaction. The template was pLSM5 (SEQ ID NO: 3), a 5.1 kb plasmid containing Taq DNA polymerase gene and used for sequencing. For the 834–951 primer set, at least 102 nucleotides must be added to the primers to form the 117 base pair product, and for the 1564–1937 primer set, at least 358 nucleotides must be added to the primer to form the 373 base pair product. The PCR program was 20 sec denaturation at 94° C., 30 sec annealing at 48° C., and 2 min extension at 72° C. for 12 cycles.

Figure 7:
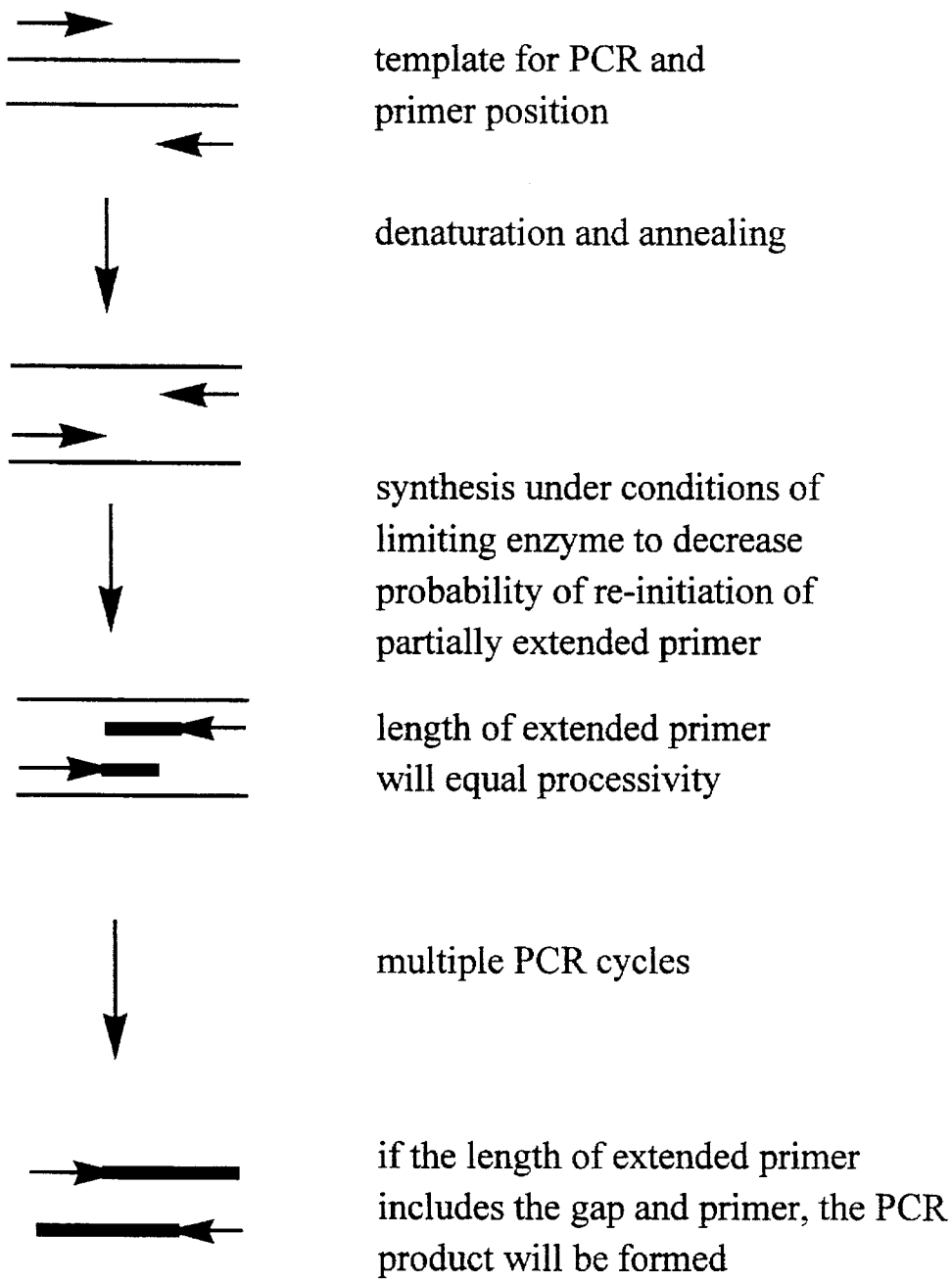
FIG. 7 is a schematic depiction of the method for testing processivity using PCR.
Figure 8:
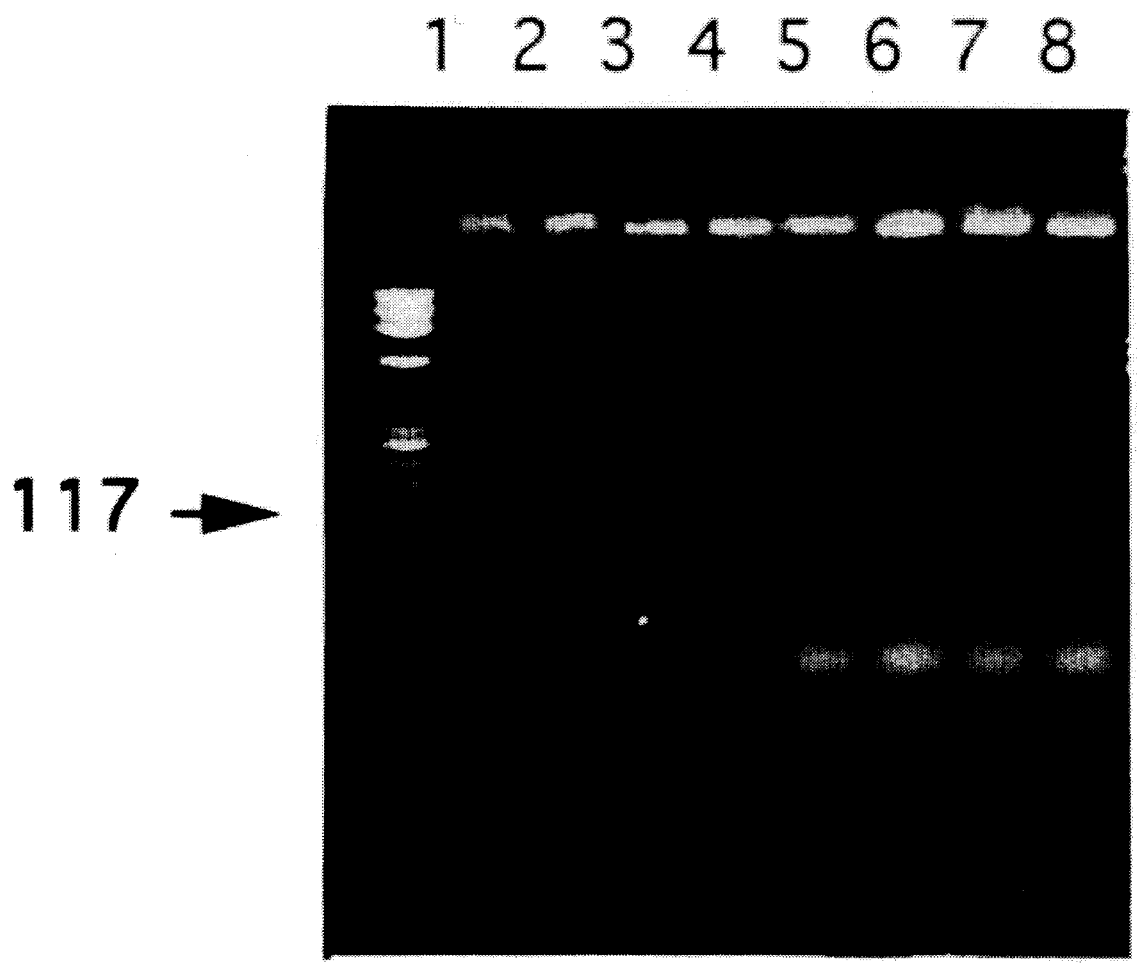
FIG. 8 is the autoradiograph showing the results of processivity testing by the PCR method.

FIG. 7 is a schematic depiction of this process and FIG. 8 shows is an autoradiograph showing the results.

Interpretation of Processivity Testing

Trials 1 and 2 are based on methodology similar to Innis et al., *Proc. Natl. Acad. Sci.* 85, 9436 (1988); Tabor et al., *J. Biol. Chem.* 262, 16212 (1987); and Wernette et al., *Biochem.* 27, 6046 (1988). The use of a fixed primer for synthesis under conditions of limiting enzyme activity and excess template/primer allows analysis of the length of extension of the primer with minimal chance for re-initiation. Thus, analysis of product size by polyacrylamide/urea gel measures primer extension as a unit event, or processivity of the polymerase (trials 1 and 2).

Trial 3 is based on a new approach. We reasoned that it would be possible to measure processivity under conditions of PCR. With limiting enzyme concentration and excess primer/template concentration, the probability of re-initiation on a partially extended primer in PCR cycles is very low. Therefore, the length of the observed product (resulting from the complete extension of a primer through the opposing primer) is a measure of processivity. We found that 12 cycles results in sufficient yield to detect products with ethidium bromide on agarose gel. By varying the distance between primers we can determine a processivity range. AmpliTaq™, REM-T2, and REM-T3 have a processivity of at least 105 nucleotides, but less that 358 nucleotides. Stoffel Fragment, on the other hand has a processivity of less than 105 nucleotides.

FIG. 8 compares the ability of four polymerases to extend a primer 105 nucleotides (Lanes 1–4) or 358 nucleotides (Lanes 5–8) under PCR conditions of excess DNA template (0.02 pmol/10 µl of reaction) and primer (10 pmol/10 µl of reaction) and limited polymerase units (0.04 units of polymerase/10 µl reaction). PCR products are shown on a 3% NuSieve gel. AmpliTaq™ is in lanes 1 and 5, Stoffel Fragment is in lanes 2 and 6, REM-T2 in lanes 3 and 7, and REM-T3 in lanes 4 and 8. Marker lane has φx174/Hae III.

It is evident from an examination of FIGS. 6, 7, and 8 that REM-T3 (SEQ ID NO: 6) has a processivity equal to or better than AmpliTaq™, and much better than the Stoffel fragment. This result demonstrates that the full length polypeptide of the modified Taq enzyme confers superior processivity compared to the truncated peptide of the Stoffel enzyme.

EXAMPLE 9

Misincorporation Rate for Modified Taq DNA Polymerases

Information already published by Barnes, *Gene* 112, 29–35 (1992) indicates that Taq DNA polymerase which has had the N-terminal region containing the 5' exonuclease domain removed has a diminished misincorporation rate. The information available indicates that such a modified Taq DNA polymerase has a two-fold lower misincorporation rate than native Taq DNA polymerase. Since the evidence presented by Barnes leads to the conclusion that the misincorporation by the Taq DNA polymerase is lowered in the absence of the exonuclease activity, we are motivated to measure the misincorporation rate of the modified Taq DNA polymerases described herein.

The assessment of misincorporation is done by several methodologies:

1. The methodology of Barnes uses a specially constructed plasmed with a flanking selectable marker, based on identification of lacZ as an indicator gene. Scoring for misincorporation in the lac gene is by the familiar blue/white test on an indicator dye (XGal). Testing for misincorporation is performed by inserting the plasmids into an indicator bacterial strain following PCR reactions in vitro.
2. The methodology of Tindall and Kunkel, *Biochemistry* 21, 6008–6013 (1988) monitors the fidelity of in vitro DNA synthesis using the lacZ gene for $\alpha$ complementation in a plasmid derived from M13 bacteriophage. Measurement of misincorporation is based on the blue/white test for lacZ function using an indicator dye in the plate. The plasmid derivative contains an open single-stranded gap region of 390 nucleotides. This construction allows measurement of the forward mutation rate, or the substantially lower reversion mutation rate for any specific misincorporation constructed. The results found by Kunkel and co-workers, indicate that the native Taq DNA polymerase has a base substitution error rate of approximately 1/9000 nucleotides polymerized.

The processivity of our modified Taq DNA polymerase is much higher than the processivity of the truncated proteolytic fragment, and since the DNA polymerase literature indicates that misincorporation correlates with re-initiation, our misincorporation rate is considerably improved relative to native Taq DNA polymerase.

What is claimed is:

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 2626 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: Thermus aquaticus ( i x ) FEATURE:

5,474,920

-continued

```
            ( A ) NAME/KEY: CDS
            ( B ) LOCATION: 121..2619

( i x ) FEATURE:
            ( A ) NAME/KEY: mat_peptide
            ( B ) LOCATION: 121..2616

( i x ) FEATURE:
            ( A ) NAME/KEY: -
            ( B ) LOCATION: 1..2625
            ( D ) OTHER INFORMATION: /note="Native Taq DNA Polymerase
                    nucleotide sequence."

( x i ) SEQUENCE DESCRIPTION: SEQ ID NO:1:
```

| | | | | | | |
|---|---|---|---|---|---|---|
| AAGCTCAGAT | CTACCTGCCT | GAGGGCGTCC | GGTTCCAGCT | GGCCCTTCCC | GAGGGGGAGA | 60 |
| GGGAGGCGTT | TCTAAAAGCC | CTTCAGGACG | CTACCCGGGG | GCGGGTGGTG | GAAGGGTAAC | 120 |

| ATG | AGG | GGG | ATG | CTG | CCC | CTC | TTT | GAG | CCC | AAG | GGC | CGG | GTC | CTC | CTG | 168 |
|---|---|---|---|---|---|---|---|---|---|---|---|---|---|---|---|---|
| Met | Arg | Gly | Met | Leu | Pro | Leu | Phe | Glu | Pro | Lys | Gly | Arg | Val | Leu | Leu | |
| 1 | | | | 5 | | | | | 10 | | | | | 15 | | |

| GTG | GAC | GGC | CAC | CAC | CTG | GCC | TAC | CGC | ACC | TTC | CAC | GCC | CTG | AAG | GGC | 216 |
|---|---|---|---|---|---|---|---|---|---|---|---|---|---|---|---|---|
| Val | Asp | Gly | His | His | Leu | Ala | Tyr | Arg | Thr | Phe | His | Ala | Leu | Lys | Gly | |
| | | | 20 | | | | | 25 | | | | | 30 | | | |

| CTC | ACC | ACC | AGC | CGG | GGG | GAG | CCG | GTG | CAG | GCG | GTC | TAC | GGC | TTC | GCC | 264 |
|---|---|---|---|---|---|---|---|---|---|---|---|---|---|---|---|---|
| Leu | Thr | Thr | Ser | Arg | Gly | Glu | Pro | Val | Gln | Ala | Val | Tyr | Gly | Phe | Ala | |
| | | | 35 | | | | | 40 | | | | | 45 | | | |

| AAG | AGC | CTC | CTC | AAG | GCC | CTC | AAG | GAG | GAC | GGG | GAC | GCG | GTG | ATC | GTG | 312 |
|---|---|---|---|---|---|---|---|---|---|---|---|---|---|---|---|---|
| Lys | Ser | Leu | Leu | Lys | Ala | Leu | Lys | Glu | Asp | Gly | Asp | Ala | Val | Ile | Val | |
| | 50 | | | | | 55 | | | | | 60 | | | | | |

| GTC | TTT | GAC | GCC | AAG | GCC | CCC | TCC | TTC | CGC | CAC | GAG | GCC | TAC | GGG | GGG | 360 |
|---|---|---|---|---|---|---|---|---|---|---|---|---|---|---|---|---|
| Val | Phe | Asp | Ala | Lys | Ala | Pro | Ser | Phe | Arg | His | Glu | Ala | Tyr | Gly | Gly | |
| 65 | | | | | 70 | | | | | 75 | | | | | 80 | |

| TAC | AAG | GCG | GGC | CGG | GCC | CCC | ACG | CCG | GAG | GAC | TTT | CCC | CGG | CAA | CTC | 408 |
|---|---|---|---|---|---|---|---|---|---|---|---|---|---|---|---|---|
| Tyr | Lys | Ala | Gly | Arg | Ala | Pro | Thr | Pro | Glu | Asp | Phe | Pro | Arg | Gln | Leu | |
| | | | | 85 | | | | | 90 | | | | | 95 | | |

| GCC | CTC | ATC | AAG | GAG | CTG | GTG | GAC | CTC | CTG | GGG | CTG | GCG | CGC | CTC | GAG | 456 |
|---|---|---|---|---|---|---|---|---|---|---|---|---|---|---|---|---|
| Ala | Leu | Ile | Lys | Glu | Leu | Val | Asp | Leu | Leu | Gly | Leu | Ala | Arg | Leu | Glu | |
| | | | 100 | | | | | 105 | | | | | 110 | | | |

| GTC | CCG | GGC | TAC | GAG | GCG | GAC | GAC | GTC | CTG | GCC | AGC | CTG | GCC | AAG | AAG | 504 |
|---|---|---|---|---|---|---|---|---|---|---|---|---|---|---|---|---|
| Val | Pro | Gly | Tyr | Glu | Ala | Asp | Asp | Val | Leu | Ala | Ser | Leu | Ala | Lys | Lys | |
| | | 115 | | | | | 120 | | | | | 125 | | | | |

| GCG | GAA | AAG | GAG | GGC | TAC | GAG | GTC | CGC | ATC | CTC | ACC | GCC | GAC | AAA | GAC | 552 |
|---|---|---|---|---|---|---|---|---|---|---|---|---|---|---|---|---|
| Ala | Glu | Lys | Glu | Gly | Tyr | Glu | Val | Arg | Ile | Leu | Thr | Ala | Asp | Lys | Asp | |
| | 130 | | | | | 135 | | | | | 140 | | | | | |

| CTT | TAC | CAG | CTC | CTT | TCC | GAC | CGC | ATC | CAC | GTC | CTC | CAC | CCC | GAG | GGG | 600 |
|---|---|---|---|---|---|---|---|---|---|---|---|---|---|---|---|---|
| Leu | Tyr | Gln | Leu | Leu | Ser | Asp | Arg | Ile | His | Val | Leu | His | Pro | Glu | Gly | |
| 145 | | | | | 150 | | | | | 155 | | | | | 160 | |

| TAC | CTC | ATC | ACC | CCG | GCC | TGG | CTT | TGG | GAA | AAG | TAC | GGC | CTG | AGG | CCC | 648 |
|---|---|---|---|---|---|---|---|---|---|---|---|---|---|---|---|---|
| Tyr | Leu | Ile | Thr | Pro | Ala | Trp | Leu | Trp | Glu | Lys | Tyr | Gly | Leu | Arg | Pro | |
| | | | | 165 | | | | | 170 | | | | | 175 | | |

| GAC | CAG | TGG | GCC | GAC | TAC | CGG | GCC | CTG | ACC | GGG | GAC | GAG | TCC | GAC | AAC | 696 |
|---|---|---|---|---|---|---|---|---|---|---|---|---|---|---|---|---|
| Asp | Gln | Trp | Ala | Asp | Tyr | Arg | Ala | Leu | Thr | Gly | Asp | Glu | Ser | Asp | Asn | |
| | | | 180 | | | | | 185 | | | | | 190 | | | |

| CTT | CCC | GGG | GTC | AAG | GGC | ATC | GGG | GAG | AAG | ACG | GCG | AGG | AAG | CTT | CTG | 744 |
|---|---|---|---|---|---|---|---|---|---|---|---|---|---|---|---|---|
| Leu | Pro | Gly | Val | Lys | Gly | Ile | Gly | Glu | Lys | Thr | Ala | Arg | Lys | Leu | Leu | |
| | | 195 | | | | | 200 | | | | | 205 | | | | |

| GAG | GAG | TGG | GGG | AGC | CTG | GAA | GCC | CTC | CTC | AAG | AAC | CTG | GAC | CGG | CTG | 792 |
|---|---|---|---|---|---|---|---|---|---|---|---|---|---|---|---|---|
| Glu | Glu | Trp | Gly | Ser | Leu | Glu | Ala | Leu | Leu | Lys | Asn | Leu | Asp | Arg | Leu | |
| | 210 | | | | | 215 | | | | | 220 | | | | | |

| AAG | CCC | GCC | ATC | CGG | GAG | AAG | ATC | CTG | GCC | CAC | ATG | GAC | GAT | CTG | AAG | 840 |
|---|---|---|---|---|---|---|---|---|---|---|---|---|---|---|---|---|
| Lys | Pro | Ala | Ile | Arg | Glu | Lys | Ile | Leu | Ala | His | Met | Asp | Asp | Leu | Lys | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| CTC | TCC | TGG | GAC | CTG | GCC | AAG | GTG | CGC | ACC | GAC | CTG | CCC | CTG | GAG | GTG | 888 |
| Leu | Ser | Trp | Asp | Leu<br>245 | Ala | Lys | Val | Arg | Thr<br>250 | Asp | Leu | Pro | Leu<br>255 | Glu | Val | |
| GAC | TTC | GCC | AAA | AGG | CGG | GAG | CCC | GAC | CGG | GAG | AGG | CTT | AGG | GCC | TTT | 936 |
| Asp | Phe | Ala | Lys<br>260 | Arg | Arg | Glu | Pro | Asp<br>265 | Arg | Glu | Arg | Leu | Arg<br>270 | Ala | Phe | |
| CTG | GAG | AGG | CTT | GAG | TTT | GGC | AGC | CTC | CTC | CAC | GAG | TTC | GGC | CTT | CTG | 984 |
| Leu | Glu | Arg<br>275 | Leu | Glu | Phe | Gly | Ser<br>280 | Leu | Leu | His | Glu | Phe<br>285 | Gly | Leu | Leu | |
| GAA | AGC | CCC | AAG | GCC | CTG | GAG | GAG | GCC | CCC | TGG | CCC | CCG | CCG | GAA | GGG | 1032 |
| Glu | Ser<br>290 | Pro | Lys | Ala | Leu | Glu<br>295 | Glu | Ala | Pro | Trp | Pro<br>300 | Pro | Pro | Glu | Gly | |
| GCC | TTC | GTG | GGC | TTT | GTG | CTT | TCC | CGC | AAG | GAG | CCC | ATG | TGG | GCC | GAT | 1080 |
| Ala<br>305 | Phe | Val | Gly | Phe | Val<br>310 | Leu | Ser | Arg | Lys | Glu<br>315 | Pro | Met | Trp | Ala | Asp<br>320 | |
| CTT | CTG | GCC | CTG | GCC | GCC | GCC | AGG | GGG | GGC | CGG | GTC | CAC | CGG | GCC | CCC | 1128 |
| Leu | Leu | Ala | Leu | Ala<br>325 | Ala | Ala | Arg | Gly | Gly<br>330 | Arg | Val | His | Arg | Ala<br>335 | Pro | |
| GAG | CCT | TAT | AAA | GCC | CTC | AGG | GAC | CTG | AAG | GAG | GCG | CGG | GGG | CTT | CTC | 1176 |
| Glu | Pro | Tyr | Lys<br>340 | Ala | Leu | Arg | Asp | Leu<br>345 | Lys | Glu | Ala | Arg | Gly<br>350 | Leu | Leu | |
| GCC | AAA | GAC | CTG | AGC | GTT | CTG | GCC | CTG | AGG | GAA | GGC | CTT | GGC | CTC | CCG | 1224 |
| Ala | Lys | Asp<br>355 | Leu | Ser | Val | Leu | Ala<br>360 | Leu | Arg | Glu | Gly | Leu<br>365 | Gly | Leu | Pro | |
| CCC | GGC | GAC | GAC | CCC | ATG | CTC | CTC | GCC | TAC | CTC | CTG | GAC | CCT | TCC | AAC | 1272 |
| Pro | Gly | Asp<br>370 | Asp | Pro | Met | Leu | Leu<br>375 | Ala | Tyr | Leu | Leu | Asp<br>380 | Pro | Ser | Asn | |
| ACC | ACC | CCC | GAG | GGG | GTG | GCC | CGG | CGC | TAC | GGC | GGG | GAG | TGG | ACG | GAG | 1320 |
| Thr<br>385 | Thr | Pro | Glu | Gly | Val<br>390 | Ala | Arg | Arg | Tyr | Gly<br>395 | Gly | Glu | Trp | Thr | Glu<br>400 | |
| GAG | GCG | GGG | GAG | CGG | GCC | GCC | CTT | TCC | GAG | AGG | CTC | TTC | GCC | AAC | CTG | 1368 |
| Glu | Ala | Gly | Glu | Arg<br>405 | Ala | Ala | Leu | Ser | Glu<br>410 | Arg | Leu | Phe | Ala | Asn<br>415 | Leu | |
| TGG | GGG | AGG | CTT | GAG | GGG | GAG | GAG | AGG | CTC | CTT | TGG | CTT | TAC | CGG | GAG | 1416 |
| Trp | Gly | Arg | Leu<br>420 | Glu | Gly | Glu | Glu | Arg<br>425 | Leu | Leu | Trp | Leu | Tyr<br>430 | Arg | Glu | |
| GTG | GAG | AGG | CCC | CTT | TCC | GCT | GTC | CTG | GCC | CAC | ATG | GAG | GCC | ACG | GGG | 1464 |
| Val | Glu | Arg<br>435 | Pro | Leu | Ser | Ala | Val<br>440 | Leu | Ala | His | Met | Glu<br>445 | Ala | Thr | Gly | |
| GTG | CGC | CTG | GAC | GTG | GCC | TAT | CTC | AGG | GCC | TTG | TCC | CTG | GAG | GTG | GCC | 1512 |
| Val | Arg | Leu<br>450 | Asp | Val | Ala | Tyr | Leu<br>455 | Arg | Ala | Leu | Ser | Leu<br>460 | Glu | Val | Ala | |
| GAG | GAG | ATC | GCC | CGC | CTC | GAG | GCC | GAG | GTC | TTC | CGC | CTG | GCC | GGC | CAC | 1560 |
| Glu<br>465 | Glu | Ile | Ala | Arg | Leu<br>470 | Glu | Ala | Glu | Val | Phe<br>475 | Arg | Leu | Ala | Gly | His<br>480 | |
| CCC | TTC | AAC | CTC | AAC | TCC | CGG | GAC | CAG | CTG | GAA | AGG | GTC | CTC | TTT | GAC | 1608 |
| Pro | Phe | Asn | Leu | Asn<br>485 | Ser | Arg | Asp | Gln | Leu<br>490 | Glu | Arg | Val | Leu | Phe<br>495 | Asp | |
| GAG | CTA | GGG | CTT | CCC | GCC | ATC | GGC | AAG | ACG | GAG | AAG | ACC | GGC | AAG | CGC | 1656 |
| Glu | Leu | Gly | Leu<br>500 | Pro | Ala | Ile | Gly | Lys<br>505 | Thr | Glu | Lys | Thr | Gly<br>510 | Lys | Arg | |
| TCC | ACC | AGC | GCC | GCC | GTC | CTG | GAG | GCC | CTC | CGC | GAG | GCC | CAC | CCC | ATC | 1704 |
| Ser | Thr | Ser<br>515 | Ala | Ala | Val | Leu | Glu<br>520 | Ala | Leu | Arg | Glu | Ala<br>525 | His | Pro | Ile | |
| GTG | GAG | AAG | ATC | CTG | CAG | TAC | CGG | GAG | CTC | ACC | AAG | CTG | AAG | AGC | ACC | 1752 |
| Val | Glu | Lys<br>530 | Ile | Leu | Gln | Tyr | Arg<br>535 | Glu | Leu | Thr | Lys | Leu<br>540 | Lys | Ser | Thr | |
| TAC | ATT | GAC | CCC | TTG | CCG | GAC | CTC | ATC | CAC | CCC | AGG | ACG | GGC | CGC | CTC | 1800 |
| Tyr<br>545 | Ile | Asp | Pro | Leu<br>550 | Pro | Asp | Leu | Ile | His<br>555 | Pro | Arg | Thr | Gly<br>560 | Arg | Leu | |

| | | | | | | | | | | | | | | | | |
|---|---|---|---|---|---|---|---|---|---|---|---|---|---|---|---|---|
| CAC | ACC | CGC | TTC | AAC | CAG | ACG | GCC | ACG | GCC | ACG | GGC | AGG | CTA | AGT | AGC | 1848 |
| His | Thr | Arg | Phe | Asn 565 | Gln | Thr | Ala | Thr 570 | Ala | Thr | Gly | Arg | Leu | Ser 575 | Ser | |
| TCC | GAT | CCC | AAC | CTC | CAG | AAC | ATC | CCC | GTC | CGC | ACC | CCG | CTT | GGG | CAG | 1896 |
| Ser | Asp | Pro | Asn 580 | Leu | Gln | Asn | Ile | Pro 585 | Val | Arg | Thr | Pro | Leu | Gly 590 | Gln | |
| AGG | ATC | CGC | CGG | GCC | TTC | ATC | GCC | GAG | GAG | GGG | TGG | CTA | TTG | GTG | GCC | 1944 |
| Arg | Ile | Arg 595 | Arg | Ala | Phe | Ile | Ala 600 | Glu | Glu | Gly | Trp | Leu | Leu 605 | Val | Ala | |
| CTG | GAC | TAT | AGC | CAG | ATA | GAG | CTC | AGG | GTG | CTG | GCC | CAC | CTC | TCC | GGC | 1992 |
| Leu | Asp 610 | Tyr | Ser | Gln | Ile | Glu 615 | Leu | Arg | Val | Leu | Ala | His 620 | Leu | Ser | Gly | |
| GAC | GAG | AAC | CTG | ATC | CGG | GTC | TTC | CAG | GAG | GGG | CGG | GAC | ATC | CAC | ACG | 2040 |
| Asp 625 | Glu | Asn | Leu | Ile | Arg 630 | Val | Phe | Gln | Glu | Gly 635 | Arg | Asp | Ile | His | Thr 640 | |
| GAG | ACC | GCC | AGC | TGG | ATG | TTC | GGC | GTC | CCC | CGG | GAG | GCC | GTG | GAC | CCC | 2088 |
| Glu | Thr | Ala | Ser | Trp 645 | Met | Phe | Gly | Val | Pro 650 | Arg | Glu | Ala | Val | Asp 655 | Pro | |
| CTG | ATG | CGC | CGG | GCG | GCC | AAG | ACC | ATC | AAC | TTC | GGG | GTC | CTC | TAC | GGC | 2136 |
| Leu | Met | Arg | Arg 660 | Ala | Ala | Lys | Thr | Ile 665 | Asn | Phe | Gly | Val | Leu 670 | Tyr | Gly | |
| ATG | TCG | GCC | CAC | CGC | CTC | TCC | CAG | GAG | CTA | GCC | ATC | CCT | TAC | GAG | GAG | 2184 |
| Met | Ser | Ala | His 675 | Arg | Leu | Ser | Gln | Glu 680 | Leu | Ala | Ile | Pro | Tyr 685 | Glu | Glu | |
| GCC | CAG | GCC | TTC | ATT | GAG | CGC | TAC | TTT | CAG | AGC | TTC | CCC | AAG | GTG | CGG | 2232 |
| Ala | Gln | Ala 690 | Phe | Ile | Glu | Arg | Tyr 695 | Phe | Gln | Ser | Phe | Pro 700 | Lys | Val | Arg | |
| GCC | TGG | ATT | GAG | AAG | ACC | CTG | GAG | GAG | GGC | AGG | AGG | CGG | GGG | TAC | GTG | 2280 |
| Ala 705 | Trp | Ile | Glu | Lys | Thr 710 | Leu | Glu | Glu | Gly | Arg 715 | Arg | Arg | Gly | Tyr | Val 720 | |
| GAG | ACC | CTC | TTC | GGC | CGC | CGC | CGC | TAC | GTG | CCA | GAC | CTA | GAG | GCC | CGG | 2328 |
| Glu | Thr | Leu | Phe | Gly 725 | Arg | Arg | Arg | Tyr | Val 730 | Pro | Asp | Leu | Glu | Ala 735 | Arg | |
| GTG | AAG | AGC | GTG | CGG | GAG | GCG | GCC | GAG | CGC | ATG | GCC | TTC | AAC | ATG | CCC | 2376 |
| Val | Lys | Ser | Val 740 | Arg | Glu | Ala | Ala | Glu 745 | Arg | Met | Ala | Phe | Asn 750 | Met | Pro | |
| GTC | CAG | GGC | ACC | GCC | GCC | GAC | CTC | ATG | AAG | CTG | GCT | ATG | GTG | AAG | CTC | 2424 |
| Val | Gln | Gly 755 | Thr | Ala | Ala | Asp | Leu 760 | Met | Lys | Leu | Ala | Met 765 | Val | Lys | Leu | |
| TTC | CCC | AGG | CTG | GAG | GAA | ATG | GGG | GCC | AGG | ATG | CTC | CTT | CAG | GTC | CAC | 2472 |
| Phe | Pro 770 | Arg | Leu | Glu | Glu | Met 775 | Gly | Ala | Arg | Met | Leu 780 | Leu | Gln | Val | His | |
| GAC | GAG | CTG | GTC | CTC | GAG | GCC | CCA | AAA | GAG | AGG | GCG | GAG | GCC | GTG | GCC | 2520 |
| Asp | Glu | Leu | Val | Leu 790 | Glu | Ala | Pro | Lys | Glu 795 | Arg | Ala | Glu | Ala | Val 800 | Ala | |
| CGG | CTG | GCC | AAG | GAG | GTC | ATG | GAG | GGG | GTG | TAT | CCC | CTG | GCC | GTG | CCC | 2568 |
| Arg | Leu | Ala | Lys | Glu 805 | Val | Met | Glu | Gly | Val 810 | Tyr | Pro | Leu | Ala | Val 815 | Pro | |
| CTG | GAG | GTG | GAG | GTG | GGG | ATA | GGG | GAG | GAC | TGG | CTC | TCC | GCC | AAG | GAG | 2616 |
| Leu | Glu | Val | Glu 820 | Val | Gly | Ile | Gly | Glu 825 | Asp | Trp | Leu | Ser | Ala 830 | Lys | Glu | |

TGATACCACC 2626

( 2 ) INFORMATION FOR SEQ ID NO:2:

( i ) SEQUENCE CHARACTERISTICS:
        ( A ) LENGTH: 832 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Arg Gly Met Leu Pro Leu Phe Glu Pro Lys Gly Arg Val Leu Leu
 1               5                  10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
        50                  55                  60

Val Phe Asp Ala Lys Ala Pro Ser Phe Arg His Glu Ala Tyr Gly Gly
 65                 70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
            115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400
```

| | | | | | | | | | | | | | | |
|---|---|---|---|---|---|---|---|---|---|---|---|---|---|---|
| Glu | Ala | Gly | Glu | Arg<br>405 | Ala | Ala | Leu | Ser | Glu<br>410 | Arg | Leu | Phe | Ala | Asn<br>415 | Leu |
| Trp | Gly | Arg | Leu<br>420 | Glu | Gly | Glu | Glu | Arg<br>425 | Leu | Leu | Trp | Leu<br>430 | Tyr | Arg | Glu |
| Val | Glu | Arg<br>435 | Pro | Leu | Ser | Ala | Val<br>440 | Leu | Ala | His | Met<br>445 | Glu | Ala | Thr | Gly |
| Val | Arg<br>450 | Leu | Asp | Val | Ala | Tyr<br>455 | Leu | Arg | Ala | Leu | Ser<br>460 | Leu | Glu | Val | Ala |
| Glu<br>465 | Glu | Ile | Ala | Arg<br>470 | Leu | Ala | Glu | Val | Phe<br>475 | Arg | Leu | Ala | Gly | His<br>480 |
| Pro | Phe | Asn | Leu | Asn<br>485 | Ser | Arg | Asp | Gln | Leu<br>490 | Glu | Arg | Val | Leu | Phe<br>495 | Asp |
| Glu | Leu | Gly | Leu<br>500 | Pro | Ala | Ile | Gly | Lys<br>505 | Thr | Glu | Lys | Thr | Gly<br>510 | Lys | Arg |
| Ser | Thr | Ser<br>515 | Ala | Ala | Val | Leu | Glu<br>520 | Ala | Leu | Arg | Glu | Ala<br>525 | His | Pro | Ile |
| Val | Glu<br>530 | Lys | Ile | Leu | Gln | Tyr<br>535 | Arg | Glu | Leu | Thr | Lys<br>540 | Leu | Lys | Ser | Thr |
| Tyr<br>545 | Ile | Asp | Pro | Leu | Pro<br>550 | Asp | Leu | Ile | His | Pro<br>555 | Arg | Thr | Gly | Arg | Leu<br>560 |
| His | Thr | Arg | Phe | Asn<br>565 | Gln | Thr | Ala | Thr | Ala<br>570 | Thr | Gly | Arg | Leu | Ser<br>575 | Ser |
| Ser | Asp | Pro | Asn<br>580 | Leu | Gln | Asn | Ile | Pro<br>585 | Val | Arg | Thr | Pro | Leu<br>590 | Gly | Gln |
| Arg | Ile | Arg<br>595 | Arg | Ala | Phe | Ile | Ala<br>600 | Glu | Glu | Gly | Trp | Leu<br>605 | Leu | Val | Ala |
| Leu | Asp<br>610 | Tyr | Ser | Gln | Ile | Glu<br>615 | Leu | Arg | Val | Leu | Ala<br>620 | His | Leu | Ser | Gly |
| Asp<br>625 | Glu | Asn | Leu | Ile | Arg<br>630 | Val | Phe | Gln | Glu | Gly<br>635 | Arg | Asp | Ile | His | Thr<br>640 |
| Glu | Thr | Ala | Ser | Trp<br>645 | Met | Phe | Gly | Val | Pro<br>650 | Arg | Glu | Ala | Val | Asp<br>655 | Pro |
| Leu | Met | Arg | Arg<br>660 | Ala | Ala | Lys | Thr | Ile<br>665 | Asn | Phe | Gly | Val | Leu<br>670 | Tyr | Gly |
| Met | Ser | Ala<br>675 | His | Arg | Leu | Ser | Gln<br>680 | Glu | Leu | Ala | Ile | Pro<br>685 | Tyr | Glu | Glu |
| Ala | Gln<br>690 | Ala | Phe | Ile | Glu | Arg<br>695 | Tyr | Phe | Gln | Ser | Phe<br>700 | Pro | Lys | Val | Arg |
| Ala<br>705 | Trp | Ile | Glu | Lys | Thr<br>710 | Leu | Glu | Glu | Gly | Arg<br>715 | Arg | Arg | Gly | Tyr | Val<br>720 |
| Glu | Thr | Leu | Phe | Gly<br>725 | Arg | Arg | Arg | Tyr | Val<br>730 | Pro | Asp | Leu | Glu | Ala<br>735 | Arg |
| Val | Lys | Ser | Val<br>740 | Arg | Glu | Ala | Ala | Glu<br>745 | Arg | Met | Ala | Phe | Asn<br>750 | Met | Pro |
| Val | Gln | Gly<br>755 | Thr | Ala | Ala | Asp | Leu<br>760 | Met | Lys | Leu | Ala | Met<br>765 | Val | Lys | Leu |
| Phe | Pro<br>770 | Arg | Leu | Glu | Glu | Met<br>775 | Gly | Ala | Arg | Met | Leu<br>780 | Leu | Gln | Val | His |
| Asp<br>785 | Glu | Leu | Val | Leu | Glu<br>790 | Ala | Pro | Lys | Glu | Arg<br>795 | Ala | Glu | Ala | Val | Ala<br>800 |
| Arg | Leu | Ala | Lys | Glu<br>805 | Val | Met | Glu | Gly | Val<br>810 | Tyr | Pro | Leu | Ala | Val<br>815 | Pro |
| Leu | Glu | Val | Glu | Val | Gly | Ile | Gly | Glu | Asp | Trp | Leu | Ser | Ala | Lys | Glu |

5,474,920

25 26

-continued 820           825           830

(2) INFORMATION FOR SEQ ID NO:3:

(i) SEQUENCE CHARACTERISTICS:
        (A) LENGTH: 2626 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Thermus aquaticus (ix) FEATURE:
        (A) NAME/KEY: mutation
        (B) LOCATION: replace(89, "g")
        (D) OTHER INFORMATION: /note="This mutation results in a
            nucleotide alteration at postion 89 of the native Taq DNA
            polymerase nucleotide sequence of C to G."

(ix) FEATURE:
        (A) NAME/KEY: mutation
        (B) LOCATION: replace(934, "a")
        (D) OTHER INFORMATION: /note="This mutation results in a
            nucleotide alteration at position 934 of the native Taq
            DNA polymerase nucleotide sequence of T to A. This
            results in an amino acid change of Phe to Ile."

(ix) FEATURE:
        (A) NAME/KEY: mutation
        (B) LOCATION: replace(962, "c")
        (D) OTHER INFORMATION: /note="This mutation results in a
            nucleotide alteration at position 962 of the native Taq
            DNA polymerase nucleotide sequence of T to C. This
            results in an amino acid change of Leu to Pro."

(ix) FEATURE:
        (A) NAME/KEY: mutation
        (B) LOCATION: replace(2535, "a")
        (D) OTHER INFORMATION: /note="This mutation results in a
            nucleotide alteration at position 2535 of the native Taq
            DNA polymerase nucleotide sequence of G to A. This
            mutation is conservative."

(ix) FEATURE:
        (A) NAME/KEY: CDS
        (B) LOCATION: 121..2619

(ix) FEATURE:
        (A) NAME/KEY: mat_peptide
        (B) LOCATION: 121..2616

(ix) FEATURE:
        (A) NAME/KEY: -
        (B) LOCATION: 1..2619
        (D) OTHER INFORMATION: /note="pLSM5"

(xi) SEQUENCE DESCRIPTION: SEQ ID NO:3:

```
AAGCTCAGAT CTACCTGCCT GAGGGCGTCC GGTTCCAGCT GGCCCTTCCC GAGGGGAGA      60

GGGAGGCGTT TCTAAAAGCC CTTCAGGAGG CTACCCGGGG GCGGGTGGTG GAAGGGTAAC    120

ATG AGG GGG ATG CTG CCC CTC TTT GAG CCC AAG GGC CGG GTC CTC CTG      168
Met Arg Gly Met Leu Pro Leu Phe Glu Pro Lys Gly Arg Val Leu Leu
 1               5                  10                  15

GTG GAC GGC CAC CAC CTG GCC TAC CGC ACC TTC CAC GCC CTG AAG GGC      216
Val Asp Gly His His Leu Ala Tyr Arg Thr Phe His Ala Leu Lys Gly
            20                  25                  30

CTC ACC ACC AGC CGG GGG GAG CCG GTG CAG GCG GTC TAC GGC TTC GCC      264
```

```
Leu Thr Thr Ser Arg Gly Glu Pro Val Gln Ala Val Tyr Gly Phe Ala
        35                  40                  45

AAG AGC CTC CTC AAG GCC CTC AAG GAG GAC GGG GAC GCG GTG ATC GTG         312
Lys Ser Leu Leu Lys Ala Leu Lys Glu Asp Gly Asp Ala Val Ile Val
    50                  55                  60

GTC TTT GAC GCC AAG GCC CCC TCC TTC CGC CAC GAG GCC TAC GGG GGG         360
Val Phe Asp Ala Lys Ala Pro Ser Phe Arg His Glu Ala Tyr Gly Gly
65                      70                  75                  80

TAC AAG GCG GGC CGG GCC CCC ACG CCG GAG GAC TTT CCC CGG CAA CTC         408
Tyr Lys Ala Gly Arg Ala Pro Thr Pro Glu Asp Phe Pro Arg Gln Leu
            85                  90                  95

GCC CTC ATC AAG GAG CTG GTG GAC CTC CTG GGG CTG GCG CGC CTC GAG         456
Ala Leu Ile Lys Glu Leu Val Asp Leu Leu Gly Leu Ala Arg Leu Glu
                100                 105                 110

GTC CCG GGC TAC GAG GCG GAC GAC GTC CTG GCC AGC CTG GCC AAG AAG         504
Val Pro Gly Tyr Glu Ala Asp Asp Val Leu Ala Ser Leu Ala Lys Lys
        115                 120                 125

GCG GAA AAG GAG GGC TAC GAG GTC CGC ATC CTC ACC GCC GAC AAA GAC         552
Ala Glu Lys Glu Gly Tyr Glu Val Arg Ile Leu Thr Ala Asp Lys Asp
    130                 135                 140

CTT TAC CAG CTC CTT TCC GAC CGC ATC CAC GTC CTC CAC CCC GAG GGG         600
Leu Tyr Gln Leu Leu Ser Asp Arg Ile His Val Leu His Pro Glu Gly
145                 150                 155                 160

TAC CTC ATC ACC CCG GCC TGG CTT TGG GAA AAG TAC GGC CTG AGG CCC         648
Tyr Leu Ile Thr Pro Ala Trp Leu Trp Glu Lys Tyr Gly Leu Arg Pro
                165                 170                 175

GAC CAG TGG GCC GAC TAC CGG GCC CTG ACC GGG GAC GAG TCC GAC AAC         696
Asp Gln Trp Ala Asp Tyr Arg Ala Leu Thr Gly Asp Glu Ser Asp Asn
            180                 185                 190

CTT CCC GGG GTC AAG GGC ATC GGG GAG AAG ACG GCG AGG AAG CTT CTG         744
Leu Pro Gly Val Lys Gly Ile Gly Glu Lys Thr Ala Arg Lys Leu Leu
        195                 200                 205

GAG GAG TGG GGG AGC CTG GAA GCC CTC CTC AAG AAC CTG GAC CGG CTG         792
Glu Glu Trp Gly Ser Leu Glu Ala Leu Leu Lys Asn Leu Asp Arg Leu
    210                 215                 220

AAG CCC GCC ATC CGG GAG AAG ATC CTG GCC CAC ATG GAC GAT CTG AAG         840
Lys Pro Ala Ile Arg Glu Lys Ile Leu Ala His Met Asp Asp Leu Lys
225                 230                 235                 240

CTC TCC TGG GAC CTG GCC AAG GTG CGC ACC GAC CTG CCC CTG GAG GTG         888
Leu Ser Trp Asp Leu Ala Lys Val Arg Thr Asp Leu Pro Leu Glu Val
                245                 250                 255

GAC TTC GCC AAA AGG CGG GAG CCC GAC CGG GAG AGG CTT AGG GCC ATT         936
Asp Phe Ala Lys Arg Arg Glu Pro Asp Arg Glu Arg Leu Arg Ala Ile
            260                 265                 270

CTG GAG AGG CTT GAG TTT GGC AGC CCC CTC CAC GAG TTC GGC CTT CTG         984
Leu Glu Arg Leu Glu Phe Gly Ser Pro Leu His Glu Phe Gly Leu Leu
        275                 280                 285

GAA AGC CCC AAG GCC CTG GAG GAG GCC CCC TGG CCC CCG CCG GAA GGG        1032
Glu Ser Pro Lys Ala Leu Glu Glu Ala Pro Trp Pro Pro Pro Glu Gly
    290                 295                 300

GCC TTC GTG GGC TTT GTG CTT TCC CGC AAG GAG CCC ATG TGG GCC GAT        1080
Ala Phe Val Gly Phe Val Leu Ser Arg Lys Glu Pro Met Trp Ala Asp
305                 310                 315                 320

CTT CTG GCC CTG GCC GCC GCC AGG GGG GGC CGG GTC CAC CGG GCC CCC        1128
Leu Leu Ala Leu Ala Ala Ala Arg Gly Gly Arg Val His Arg Ala Pro
                325                 330                 335

GAG CCT TAT AAA GCC CTC AGG GAC CTG AAG GAG GCG CGG GGG CTT CTC        1176
Glu Pro Tyr Lys Ala Leu Arg Asp Leu Lys Glu Ala Arg Gly Leu Leu
            340                 345                 350
```

```
GCC AAA GAC CTG AGC GTT CTG GCC CTG AGG GAA GGC CTT GGC CTC CCG     1224
Ala Lys Asp Leu Ser Val Leu Ala Leu Arg Glu Gly Leu Gly Leu Pro
    355             360                 365

CCC GGC GAC GAC CCC ATG CTC CTC GCC TAC CTC CTG GAC CCT TCC AAC     1272
Pro Gly Asp Asp Pro Met Leu Leu Ala Tyr Leu Leu Asp Pro Ser Asn
    370             375                 380

ACC ACC CCC GAG GGG GTG GCC CGG CGC TAC GGC GGG GAG TGG ACG GAG     1320
Thr Thr Pro Glu Gly Val Ala Arg Arg Tyr Gly Gly Glu Trp Thr Glu
385             390                 395                 400

GAG GCG GGG GAG CGG GCC GCC CTT TCC GAG AGG CTC TTC GCC AAC CTG     1368
Glu Ala Gly Glu Arg Ala Ala Leu Ser Glu Arg Leu Phe Ala Asn Leu
                405                 410                 415

TGG GGG AGG CTT GAG GGG GAG GAG AGG CTC CTT TGG CTT TAC CGG GAG     1416
Trp Gly Arg Leu Glu Gly Glu Glu Arg Leu Leu Trp Leu Tyr Arg Glu
            420                 425                 430

GTG GAG AGG CCC CTT TCC GCT GTC CTG GCC CAC ATG GAG GCC ACG GGG     1464
Val Glu Arg Pro Leu Ser Ala Val Leu Ala His Met Glu Ala Thr Gly
            435                 440                 445

GTG CGC CTG GAC GTG GCC TAT CTC AGG GCC TTG TCC CTG GAG GTG GCC     1512
Val Arg Leu Asp Val Ala Tyr Leu Arg Ala Leu Ser Leu Glu Val Ala
    450                 455                 460

GAG GAG ATC GCC CGC CTC GAG GCC GAG GTC TTC CGC CTG GCC GGC CAC     1560
Glu Glu Ile Ala Arg Leu Glu Ala Glu Val Phe Arg Leu Ala Gly His
465                 470                 475                 480

CCC TTC AAC CTC AAC TCC CGG GAC CAG CTG GAA AGG GTC CTC TTT GAC     1608
Pro Phe Asn Leu Asn Ser Arg Asp Gln Leu Glu Arg Val Leu Phe Asp
                485                 490                 495

GAG CTA GGG CTT CCC GCC ATC GGC AAG ACG GAG AAG ACC GGC AAG CGC     1656
Glu Leu Gly Leu Pro Ala Ile Gly Lys Thr Glu Lys Thr Gly Lys Arg
            500                 505                 510

TCC ACC AGC GCC GCC GTC CTG GAG GCC CTC CGC GAG GCC CAC CCC ATC     1704
Ser Thr Ser Ala Ala Val Leu Glu Ala Leu Arg Glu Ala His Pro Ile
        515                 520                 525

GTG GAG AAG ATC CTG CAG TAC CGG GAG CTC ACC AAG CTG AAG AGC ACC     1752
Val Glu Lys Ile Leu Gln Tyr Arg Glu Leu Thr Lys Leu Lys Ser Thr
    530                 535                 540

TAC ATT GAC CCC TTG CCG GAC CTC ATC CAC CCC AGG ACG GGC CGC CTC     1800
Tyr Ile Asp Pro Leu Pro Asp Leu Ile His Pro Arg Thr Gly Arg Leu
545                 550                 555                 560

CAC ACC CGC TTC AAC CAG ACG GCC ACG GCC ACG GGC AGG CTA AGT AGC     1848
His Thr Arg Phe Asn Gln Thr Ala Thr Ala Thr Gly Arg Leu Ser Ser
                565                 570                 575

TCC GAT CCC AAC CTC CAG AAC ATC CCC GTC CGC ACC CCG CTT GGG CAG     1896
Ser Asp Pro Asn Leu Gln Asn Ile Pro Val Arg Thr Pro Leu Gly Gln
            580                 585                 590

AGG ATC CGC CGG GCC TTC ATC GCC GAG GAG GGG TGG CTA TTG GTG GCC     1944
Arg Ile Arg Arg Ala Phe Ile Ala Glu Glu Gly Trp Leu Leu Val Ala
        595                 600                 605

CTG GAC TAT AGC CAG ATA GAG CTC AGG GTG CTG GCC CAC CTC TCC GGC     1992
Leu Asp Tyr Ser Gln Ile Glu Leu Arg Val Leu Ala His Leu Ser Gly
    610                 615                 620

GAC GAG AAC CTG ATC CGG GTC TTC CAG GAG GGG CGG GAC ATC CAC ACG     2040
Asp Glu Asn Leu Ile Arg Val Phe Gln Glu Gly Arg Asp Ile His Thr
625                 630                 635                 640

GAG ACC GCC AGC TGG ATG TTC GGC GTC CCC CGG GAG GCC GTG GAC CCC     2088
Glu Thr Ala Ser Trp Met Phe Gly Val Pro Arg Glu Ala Val Asp Pro
                645                 650                 655

CTG ATG CGC CGG GCG GCC AAG ACC ATC AAC TTC GGG GTC CTC TAC GGC     2136
Leu Met Arg Arg Ala Ala Lys Thr Ile Asn Phe Gly Val Leu Tyr Gly
            660                 665                 670
```

| | | | | | | | | | | | | | | | | |
|---|---|---|---|---|---|---|---|---|---|---|---|---|---|---|---|---|
| ATG | TCG | GCC | CAC | CGC | CTC | TCC | CAG | GAG | CTA | GCC | ATC | CCT | TAC | GAG | GAG | 2184 |
| Met | Ser | Ala | His | Arg | Leu | Ser | Gln | Glu | Leu | Ala | Ile | Pro | Tyr | Glu | Glu | |
| | | 675 | | | | | 680 | | | | | 685 | | | | |
| GCC | CAG | GCC | TTC | ATT | GAG | CGC | TAC | TTT | CAG | AGC | TTC | CCC | AAG | GTG | CGG | 2232 |
| Ala | Gln | Ala | Phe | Ile | Glu | Arg | Tyr | Phe | Gln | Ser | Phe | Pro | Lys | Val | Arg | |
| | 690 | | | | | 695 | | | | | 700 | | | | | |
| GCC | TGG | ATT | GAG | AAG | ACC | CTG | GAG | GAG | GGC | AGG | AGG | CGG | GGG | TAC | GTG | 2280 |
| Ala | Trp | Ile | Glu | Lys | Thr | Leu | Glu | Glu | Gly | Arg | Arg | Arg | Gly | Tyr | Val | |
| 705 | | | | | 710 | | | | | 715 | | | | | 720 | |
| GAG | ACC | CTC | TTC | GGC | CGC | CGC | CGC | TAC | GTG | CCA | GAC | CTA | GAG | GCC | CGG | 2328 |
| Glu | Thr | Leu | Phe | Gly | Arg | Arg | Arg | Tyr | Val | Pro | Asp | Leu | Glu | Ala | Arg | |
| | | | | 725 | | | | | 730 | | | | | 735 | | |
| GTG | AAG | AGC | GTG | CGG | GAG | GCG | GCC | GAG | CGC | ATG | GCC | TTC | AAC | ATG | CCC | 2376 |
| Val | Lys | Ser | Val | Arg | Glu | Ala | Ala | Glu | Arg | Met | Ala | Phe | Asn | Met | Pro | |
| | | | 740 | | | | | 745 | | | | | 750 | | | |
| GTC | CAG | GGC | ACC | GCC | GCC | GAC | CTC | ATG | AAG | CTG | GCT | ATG | GTG | AAG | CTC | 2424 |
| Val | Gln | Gly | Thr | Ala | Ala | Asp | Leu | Met | Lys | Leu | Ala | Met | Val | Lys | Leu | |
| | | 755 | | | | | 760 | | | | | 765 | | | | |
| TTC | CCC | AGG | CTG | GAG | GAA | ATG | GGG | GCC | AGG | ATG | CTC | CTT | CAG | GTC | CAC | 2472 |
| Phe | Pro | Arg | Leu | Glu | Glu | Met | Gly | Ala | Arg | Met | Leu | Leu | Gln | Val | His | |
| | 770 | | | | | 775 | | | | | 780 | | | | | |
| GAC | GAG | CTG | GTC | CTC | GAG | GCC | CCA | AAA | GAG | AGG | GCG | GAG | GCC | GTG | GCC | 2520 |
| Asp | Glu | Leu | Val | Leu | Glu | Ala | Pro | Lys | Glu | Arg | Ala | Glu | Ala | Val | Ala | |
| 785 | | | | | 790 | | | | | 795 | | | | | 800 | |
| CGG | CTG | GCC | AAG | GAA | GTC | ATG | GAG | GGG | GTG | TAT | CCC | CTG | GCC | GTG | CCC | 2568 |
| Arg | Leu | Ala | Lys | Glu | Val | Met | Glu | Gly | Val | Tyr | Pro | Leu | Ala | Val | Pro | |
| | | | | 805 | | | | | 810 | | | | | 815 | | |
| CTG | GAG | GTG | GAG | GTG | GGG | ATA | GGG | GAG | GAC | TGG | CTC | TCC | GCC | AAG | GAG | 2616 |
| Leu | Glu | Val | Glu | Val | Gly | Ile | Gly | Glu | Asp | Trp | Leu | Ser | Ala | Lys | Glu | |
| | | | 820 | | | | | 825 | | | | | 830 | | | |

TGATACCACC 2626

(2) INFORMATION FOR SEQ ID NO:4:

(i) SEQUENCE CHARACTERISTICS:
        (A) LENGTH: 832 amino acids
        (B) TYPE: amino acid
        (D) TOPOLOGY: linear (ii) MOLECULE TYPE: protein (xi) SEQUENCE DESCRIPTION: SEQ ID NO:4:

| | | | | | | | | | | | | | | |
|---|---|---|---|---|---|---|---|---|---|---|---|---|---|---|
| Met | Arg | Gly | Met | Leu | Pro | Leu | Phe | Glu | Pro | Lys | Gly | Arg | Val | Leu | Leu |
| 1 | | | | 5 | | | | | 10 | | | | | 15 | |
| Val | Asp | Gly | His | His | Leu | Ala | Tyr | Arg | Thr | Phe | His | Ala | Leu | Lys | Gly |
| | | | 20 | | | | | 25 | | | | | 30 | | |
| Leu | Thr | Thr | Ser | Arg | Gly | Glu | Pro | Val | Gln | Ala | Val | Tyr | Gly | Phe | Ala |
| | | 35 | | | | | 40 | | | | | 45 | | | |
| Lys | Ser | Leu | Leu | Lys | Ala | Leu | Lys | Glu | Asp | Gly | Asp | Ala | Val | Ile | Val |
| | 50 | | | | 55 | | | | | 60 | | | | | |
| Val | Phe | Asp | Ala | Lys | Ala | Pro | Ser | Phe | Arg | His | Glu | Ala | Tyr | Gly | Gly |
| 65 | | | | 70 | | | | | 75 | | | | | 80 | |
| Tyr | Lys | Ala | Gly | Arg | Ala | Pro | Thr | Pro | Glu | Asp | Phe | Pro | Arg | Gln | Leu |
| | | | | 85 | | | | | 90 | | | | | 95 | |
| Ala | Leu | Ile | Lys | Glu | Leu | Val | Asp | Leu | Leu | Gly | Leu | Ala | Arg | Leu | Glu |
| | | | 100 | | | | | 105 | | | | | 110 | | |
| Val | Pro | Gly | Tyr | Glu | Ala | Asp | Asp | Val | Leu | Ala | Ser | Leu | Ala | Lys | Lys |
| | | 115 | | | | | 120 | | | | | 125 | | | |

-continued

| | | | | | | | | | | | | | | |
|---|---|---|---|---|---|---|---|---|---|---|---|---|---|---|
| Ala | Glu | Lys | Glu | Gly | Tyr | Glu | Val | Arg | Ile | Leu | Thr | Ala | Asp | Lys | Asp |
| | 130 | | | | 135 | | | | | 140 | | | | | |
| Leu | Tyr | Gln | Leu | Leu | Ser | Asp | Arg | Ile | His | Val | Leu | His | Pro | Glu | Gly |
| 145 | | | | | 150 | | | | | 155 | | | | | 160 |
| Tyr | Leu | Ile | Thr | Pro | Ala | Trp | Leu | Trp | Glu | Lys | Tyr | Gly | Leu | Arg | Pro |
| | | | | 165 | | | | | 170 | | | | | 175 | |
| Asp | Gln | Trp | Ala | Asp | Tyr | Arg | Ala | Leu | Thr | Gly | Asp | Glu | Ser | Asp | Asn |
| | | | 180 | | | | | 185 | | | | | 190 | | |
| Leu | Pro | Gly | Val | Lys | Gly | Ile | Gly | Glu | Lys | Thr | Ala | Arg | Lys | Leu | Leu |
| | | 195 | | | | | 200 | | | | | 205 | | | |
| Glu | Glu | Trp | Gly | Ser | Leu | Glu | Ala | Leu | Leu | Lys | Asn | Leu | Asp | Arg | Leu |
| | 210 | | | | | 215 | | | | | 220 | | | | |
| Lys | Pro | Ala | Ile | Arg | Glu | Lys | Ile | Leu | Ala | His | Met | Asp | Asp | Leu | Lys |
| 225 | | | | | 230 | | | | | 235 | | | | | 240 |
| Leu | Ser | Trp | Asp | Leu | Ala | Lys | Val | Arg | Thr | Asp | Leu | Pro | Leu | Glu | Val |
| | | | | 245 | | | | | 250 | | | | | 255 | |
| Asp | Phe | Ala | Lys | Arg | Arg | Glu | Pro | Asp | Arg | Glu | Arg | Leu | Arg | Ala | Ile |
| | | | 260 | | | | | 265 | | | | | 270 | | |
| Leu | Glu | Arg | Leu | Glu | Phe | Gly | Ser | Pro | Leu | His | Glu | Phe | Gly | Leu | Leu |
| | | 275 | | | | | 280 | | | | | 285 | | | |
| Glu | Ser | Pro | Lys | Ala | Leu | Glu | Glu | Ala | Pro | Trp | Pro | Pro | Pro | Glu | Gly |
| | 290 | | | | | 295 | | | | | 300 | | | | |
| Ala | Phe | Val | Gly | Phe | Val | Leu | Ser | Arg | Lys | Glu | Pro | Met | Trp | Ala | Asp |
| 305 | | | | | 310 | | | | | 315 | | | | | 320 |
| Leu | Leu | Ala | Leu | Ala | Ala | Arg | Gly | Gly | Arg | Val | His | Arg | Ala | Pro | |
| | | | | 325 | | | | | 330 | | | | | 335 | |
| Glu | Pro | Tyr | Lys | Ala | Leu | Arg | Asp | Leu | Lys | Glu | Ala | Arg | Gly | Leu | Leu |
| | | | 340 | | | | | 345 | | | | | 350 | | |
| Ala | Lys | Asp | Leu | Ser | Val | Leu | Ala | Leu | Arg | Glu | Gly | Leu | Gly | Leu | Pro |
| | | | 355 | | | | | 360 | | | | | 365 | | |
| Pro | Gly | Asp | Asp | Pro | Met | Leu | Leu | Ala | Tyr | Leu | Leu | Asp | Pro | Ser | Asn |
| | | 370 | | | | | 375 | | | | | 380 | | | |
| Thr | Thr | Pro | Glu | Gly | Val | Ala | Arg | Arg | Tyr | Gly | Gly | Glu | Trp | Thr | Glu |
| 385 | | | | | 390 | | | | | 395 | | | | | 400 |
| Glu | Ala | Gly | Glu | Arg | Ala | Ala | Leu | Ser | Glu | Arg | Leu | Phe | Ala | Asn | Leu |
| | | | | 405 | | | | | 410 | | | | | 415 | |
| Trp | Gly | Arg | Leu | Glu | Gly | Glu | Glu | Arg | Leu | Leu | Trp | Leu | Tyr | Arg | Glu |
| | | | 420 | | | | | 425 | | | | | 430 | | |
| Val | Glu | Arg | Pro | Leu | Ser | Ala | Val | Leu | Ala | His | Met | Glu | Ala | Thr | Gly |
| | | 435 | | | | | 440 | | | | | 445 | | | |
| Val | Arg | Leu | Asp | Val | Ala | Tyr | Leu | Arg | Ala | Leu | Ser | Leu | Glu | Val | Ala |
| | 450 | | | | | 455 | | | | | 460 | | | | |
| Glu | Glu | Ile | Ala | Arg | Leu | Glu | Ala | Glu | Val | Phe | Arg | Leu | Ala | Gly | His |
| 465 | | | | | 470 | | | | | 475 | | | | | 480 |
| Pro | Phe | Asn | Leu | Asn | Ser | Arg | Asp | Gln | Leu | Glu | Arg | Val | Leu | Phe | Asp |
| | | | | 485 | | | | | 490 | | | | | 495 | |
| Glu | Leu | Gly | Leu | Pro | Ala | Ile | Gly | Lys | Thr | Glu | Lys | Thr | Gly | Lys | Arg |
| | | | 500 | | | | | 505 | | | | | 510 | | |
| Ser | Thr | Ser | Ala | Ala | Val | Leu | Glu | Ala | Leu | Arg | Glu | Ala | His | Pro | Ile |
| | | | 515 | | | | | 520 | | | | | 525 | | |
| Val | Glu | Lys | Ile | Leu | Gln | Tyr | Arg | Glu | Leu | Thr | Lys | Leu | Lys | Ser | Thr |
| | 530 | | | | | 535 | | | | | 540 | | | | |
| Tyr | Ile | Asp | Pro | Leu | Pro | Asp | Leu | Ile | His | Pro | Arg | Thr | Gly | Arg | Leu |

-continued

| 545 | | | | | 550 | | | | | 555 | | | | | 560 |
|---|---|---|---|---|---|---|---|---|---|---|---|---|---|---|---|
| His | Thr | Arg | Phe | Asn<br>565 | Gln | Thr | Ala | Thr<br>570 | Ala | Thr | Gly | Arg | Leu | Ser<br>575 | Ser |
| Ser | Asp | Pro | Asn<br>580 | Leu | Gln | Asn | Ile | Pro<br>585 | Val | Arg | Thr | Pro | Leu<br>590 | Gly | Gln |
| Arg | Ile | Arg<br>595 | Arg | Ala | Phe | Ile | Ala<br>600 | Glu | Glu | Gly | Trp | Leu<br>605 | Leu | Val | Ala |
| Leu | Asp<br>610 | Tyr | Ser | Gln | Ile | Glu<br>615 | Leu | Arg | Val | Leu | Ala<br>620 | His | Leu | Ser | Gly |
| Asp<br>625 | Glu | Asn | Leu | Ile | Arg<br>630 | Val | Phe | Gln | Glu | Gly<br>635 | Arg | Asp | Ile | His | Thr<br>640 |
| Glu | Thr | Ala | Ser | Trp<br>645 | Met | Phe | Gly | Val | Pro<br>650 | Arg | Glu | Ala | Val | Asp<br>655 | Pro |
| Leu | Met | Arg | Arg<br>660 | Ala | Ala | Lys | Thr | Ile<br>665 | Asn | Phe | Gly | Val | Leu<br>670 | Tyr | Gly |
| Met | Ser | Ala<br>675 | His | Arg | Leu | Ser | Gln<br>680 | Glu | Leu | Ala | Ile | Pro<br>685 | Tyr | Glu | Glu |
| Ala | Gln<br>690 | Ala | Phe | Ile | Glu | Arg<br>695 | Tyr | Phe | Gln | Ser | Phe<br>700 | Pro | Lys | Val | Arg |
| Ala<br>705 | Trp | Ile | Glu | Lys | Thr<br>710 | Leu | Glu | Glu | Gly | Arg<br>715 | Arg | Arg | Gly | Tyr | Val<br>720 |
| Glu | Thr | Leu | Phe | Gly<br>725 | Arg | Arg | Arg | Tyr | Val<br>730 | Pro | Asp | Leu | Glu | Ala<br>735 | Arg |
| Val | Lys | Ser | Val<br>740 | Arg | Glu | Ala | Ala | Glu<br>745 | Arg | Met | Ala | Phe | Asn<br>750 | Met | Pro |
| Val | Gln | Gly<br>755 | Thr | Ala | Ala | Asp | Leu<br>760 | Met | Lys | Leu | Ala | Met<br>765 | Val | Lys | Leu |
| Phe | Pro<br>770 | Arg | Leu | Glu | Glu | Met<br>775 | Gly | Ala | Arg | Met | Leu<br>780 | Leu | Gln | Val | His |
| Asp<br>785 | Glu | Leu | Val | Leu | Glu<br>790 | Ala | Pro | Lys | Glu | Arg<br>795 | Ala | Glu | Ala | Val | Ala<br>800 |
| Arg | Leu | Ala | Lys | Glu<br>805 | Val | Met | Glu | Gly | Val<br>810 | Tyr | Pro | Leu | Ala | Val<br>815 | Pro |
| Leu | Glu | Val | Glu<br>820 | Val | Gly | Ile | Gly | Glu<br>825 | Asp | Trp | Leu | Ser | Ala<br>830 | Lys | Glu |

( 2 ) INFORMATION FOR SEQ ID NO:5:

( i ) SEQUENCE CHARACTERISTICS:
        ( A ) LENGTH: 2626 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Thermus aquaticus ( i x ) FEATURE:
        ( A ) NAME/KEY: mutation
        ( B ) LOCATION: replace(89, "g")
        ( D ) OTHER INFORMATION: /note="This mutation results in a
            nucleotide alteration at position 89 of the native Taq
            DNA polymerase nucleotide sequence of C to G."

( i x ) FEATURE:

(A) NAME/KEY: mutation
(B) LOCATION: replace(934, "a")
(D) OTHER INFORMATION: /note="This mutation results in a nucleotide alteration at position 934 of the native Taq DNA polymerase nucleotide sequence of T to A. This results in an amino acid change of Phe to Ile."

(ix) FEATURE:
(A) NAME/KEY: mutation
(B) LOCATION: replace(962, "c")
(D) OTHER INFORMATION: /note="This mutation results in a nucleotide alteration at position 962 of the native Taq DNA polymerase nucleotide sequence of T to C. This results in an amino acid change of Leu to Pro."

(ix) FEATURE:
(A) NAME/KEY: mutation
(B) LOCATION: replace(2535, "a")
(D) OTHER INFORMATION: /note="This mutation results in a nucleotide alteration at position 2535 of the native Taq DNA polymerase nucleotide sequence of G to A. This mutation is conservative."

(ix) FEATURE:
(A) NAME/KEY: mutation
(B) LOCATION: replace(193, "t")
(D) OTHER INFORMATION: /note="This mutation changes the nucleotide at position 193 of the native Taq DNA polymerase from C to T, resulting in an amino acid change of Arg to Cys."

(ix) FEATURE:
(A) NAME/KEY: mutation
(B) LOCATION: replace(504, "a")
(D) OTHER INFORMATION: /note="This mutation changes the nucleotide at position 504 of the native Taq DNA polymerase from G to A, which is conservative in nature."

(ix) FEATURE:
(A) NAME/KEY: CDS
(B) LOCATION: 121..2619

(ix) FEATURE:
(A) NAME/KEY: mat_peptide
(B) LOCATION: 121..2616

(ix) FEATURE:
(A) NAME/KEY: -
(B) LOCATION: 1..2619
(D) OTHER INFORMATION: /note="pTarf3"

(xi) SEQUENCE DESCRIPTION: SEQ ID NO:5:

```
AAGCTCAGAT CTACCTGCCT GAGGGCGTCC GGTTCCAGCT GGCCCTTCCC GAGGGGAGA          60

GGGAGGCGTT TCTAAAAGCC CTTCAGGAGG CTACCCGGGG GCGGGTGGTG GAAGGGTAAC        120

ATG AGG GGG ATG CTG CCC CTC TTT GAG CCC AAG GGC CGG GTC CTC CTG         168
Met Arg Gly Met Leu Pro Leu Phe Glu Pro Lys Gly Arg Val Leu Leu
  1               5                  10                  15

GTG GAC GGC CAC CAC CTG GCC TAC TGC ACC TTC CAC GCC CTG AAG GGC         216
Val Asp Gly His His Leu Ala Tyr Cys Thr Phe His Ala Leu Lys Gly
             20                  25                  30

CTC ACC ACC AGC CGG GGG GAG CCG GTG CAG GCG GTC TAC GGC TTC GCC         264
Leu Thr Thr Ser Arg Gly Glu Pro Val Gln Ala Val Tyr Gly Phe Ala
         35                  40                  45

AAG AGC CTC CTC AAG GCC CTC AAG GAG GAC GGG GAC GCG GTG ATC GTG         312
Lys Ser Leu Leu Lys Ala Leu Lys Glu Asp Gly Asp Ala Val Ile Val
     50                  55                  60

GTC TTT GAC GCC AAG GCC CCC TCC TTC CGC CAC GAG GCC TAC GGG GGG         360
Val Phe Asp Ala Lys Ala Pro Ser Phe Arg His Glu Ala Tyr Gly Gly
 65                  70                  75                  80

TAC AAG GCG GGC CGG GCC CCC ACG CCG GAG GAC TTT CCC CGG CAA CTC         408
Tyr Lys Ala Gly Arg Ala Pro Thr Pro Glu Asp Phe Pro Arg Gln Leu
```

|  | 85 | 90 | 95 |  |
|---|---|---|---|---|
| GCC CTC ATC AAG GAG CTG GTG GAC CTC CTG GGG CTG GCG CGC CTC GAG | | | | 456 |
| Ala Leu Ile Lys Glu Leu Val Asp Leu Leu Gly Leu Ala Arg Leu Glu | | | | |
|  | 100 | 105 | 110 | |
| GTC CCG GGC TAC GAG GCG GAC GAC GTC CTG GCC AGC CTG GCC AAG AAA | | | | 504 |
| Val Pro Gly Tyr Glu Ala Asp Asp Val Leu Ala Ser Leu Ala Lys Lys | | | | |
|  | 115 | 120 | 125 | |
| GCG GAA AAG GAG GGC TAC GAG GTC CGC ATC CTC ACC GCC GAC AAA GAC | | | | 552 |
| Ala Glu Lys Glu Gly Tyr Glu Val Arg Ile Leu Thr Ala Asp Lys Asp | | | | |
| 130 | | 135 | 140 | |
| CTT TAC CAG CTC CTT TCC GAC CGC ATC CAC GTC CTC CAC CCC GAG GGG | | | | 600 |
| Leu Tyr Gln Leu Leu Ser Asp Arg Ile His Val Leu His Pro Glu Gly | | | | |
| 145 | 150 | 155 | 160 | |
| TAC CTC ATC ACC CCG GCC TGG CTT TGG GAA AAG TAC GGC CTG AGG CCC | | | | 648 |
| Tyr Leu Ile Thr Pro Ala Trp Leu Trp Glu Lys Tyr Gly Leu Arg Pro | | | | |
|  | 165 | 170 | 175 | |
| GAC CAG TGG GCC GAC TAC CGG GCC CTG ACC GGG GAC GAG TCC GAC AAC | | | | 696 |
| Asp Gln Trp Ala Asp Tyr Arg Ala Leu Thr Gly Asp Glu Ser Asp Asn | | | | |
|  | 180 | 185 | 190 | |
| CTT CCC GGG GTC AAG GGC ATC GGG GAG AAG ACG GCG AGG AAG CTT CTG | | | | 744 |
| Leu Pro Gly Val Lys Gly Ile Gly Glu Lys Thr Ala Arg Lys Leu Leu | | | | |
|  | 195 | 200 | 205 | |
| GAG GAG TGG GGG AGC CTG GAA GCC CTC CTC AAG AAC CTG GAC CGG CTG | | | | 792 |
| Glu Glu Trp Gly Ser Leu Glu Ala Leu Leu Lys Asn Leu Asp Arg Leu | | | | |
| 210 | | 215 | 220 | |
| AAG CCC GCC ATC CGG GAG AAG ATC CTG GCC CAC ATG GAC GAT CTG AAG | | | | 840 |
| Lys Pro Ala Ile Arg Glu Lys Ile Leu Ala His Met Asp Asp Leu Lys | | | | |
| 225 | | 230 | 235 | 240 | |
| CTC TCC TGG GAC CTG GCC AAG GTG CGC ACC GAC CTG CCC CTG GAG GTG | | | | 888 |
| Leu Ser Trp Asp Leu Ala Lys Val Arg Thr Asp Leu Pro Leu Glu Val | | | | |
|  | 245 | 250 | 255 | |
| GAC TTC GCC AAA AGG CGG GAG CCC GAC CGG GAG AGG CTT AGG GCC ATT | | | | 936 |
| Asp Phe Ala Lys Arg Arg Glu Pro Asp Arg Glu Arg Leu Arg Ala Ile | | | | |
|  | 260 | 265 | 270 | |
| CTG GAG AGG CTT GAG TTT GGC AGC CCC CTC CAC GAG TTC GGC CTT CTG | | | | 984 |
| Leu Glu Arg Leu Glu Phe Gly Ser Pro Leu His Glu Phe Gly Leu Leu | | | | |
|  | 275 | 280 | 285 | |
| GAA AGC CCC AAG GCC CTG GAG GAG GCC CCC TGG CCC CCG CCG GAA GGG | | | | 1032 |
| Glu Ser Pro Lys Ala Leu Glu Glu Ala Pro Trp Pro Pro Pro Glu Gly | | | | |
| 290 | | 295 | 300 | |
| GCC TTC GTG GGC TTT GTG CTT TCC CGC AAG GAG CCC ATG TGG GCC GAT | | | | 1080 |
| Ala Phe Val Gly Phe Val Leu Ser Arg Lys Glu Pro Met Trp Ala Asp | | | | |
| 305 | | 310 | 315 | 320 | |
| CTT CTG GCC CTG GCC GCC GCC AGG GGG GGC CGG GTC CAC CGG GCC CCC | | | | 1128 |
| Leu Leu Ala Leu Ala Ala Ala Arg Gly Gly Arg Val His Arg Ala Pro | | | | |
|  | 325 | 330 | 335 | |
| GAG CCT TAT AAA GCC CTC AGG GAC CTG AAG GAG GCG CGG GGG CTT CTC | | | | 1176 |
| Glu Pro Tyr Lys Ala Leu Arg Asp Leu Lys Glu Ala Arg Gly Leu Leu | | | | |
|  | 340 | 345 | 350 | |
| GCC AAA GAC CTG AGC GTT CTG GCC CTG AGG GAA GGC CTT GGC CTC CCG | | | | 1224 |
| Ala Lys Asp Leu Ser Val Leu Ala Leu Arg Glu Gly Leu Gly Leu Pro | | | | |
|  | 355 | 360 | 365 | |
| CCC GGC GAC GAC CCC ATG CTC CTC GCC TAC CTC CTG GAC CCT TCC AAC | | | | 1272 |
| Pro Gly Asp Asp Pro Met Leu Leu Ala Tyr Leu Leu Asp Pro Ser Asn | | | | |
|  | 370 | 375 | 380 | |
| ACC ACC CCC GAG GGG GTG GCC CGG CGC TAC GGC GGG GAG TGG ACG GAG | | | | 1320 |
| Thr Thr Pro Glu Gly Val Ala Arg Arg Tyr Gly Gly Glu Trp Thr Glu | | | | |
| 385 | | 390 | 395 | 400 | |
| GAG GCG GGG GAG CGG GCC GCC CTT TCC GAG AGG CTC TTC GCC AAC CTG | | | | 1368 |

|  |  |  |  |  |  |  |  |  |  |  |  |  |  |  |  |
|---|---|---|---|---|---|---|---|---|---|---|---|---|---|---|---|
| Glu | Ala | Gly | Glu | Arg<br>405 | Ala | Ala | Leu | Ser | Glu<br>410 | Arg | Leu | Phe | Ala | Asn<br>415 | Leu |

| TGG | GGG | AGG | CTT | GAG | GGG | GAG | GAG | AGG | CTC | CTT | TGG | CTT | TAC | CGG | GAG | 1416 |
|---|---|---|---|---|---|---|---|---|---|---|---|---|---|---|---|---|
| Trp | Gly | Arg | Leu<br>420 | Glu | Gly | Glu | Glu | Arg<br>425 | Leu | Leu | Trp | Leu | Tyr<br>430 | Arg | Glu | |

| GTG | GAG | AGG | CCC | CTT | TCC | GCT | GTC | CTG | GCC | CAC | ATG | GAG | GCC | ACG | GGG | 1464 |
|---|---|---|---|---|---|---|---|---|---|---|---|---|---|---|---|---|
| Val | Glu | Arg<br>435 | Pro | Leu | Ser | Ala | Val<br>440 | Leu | Ala | His | Met | Glu<br>445 | Ala | Thr | Gly | |

| GTG | CGC | CTG | GAC | GTG | GCC | TAT | CTC | AGG | GCC | TTG | TCC | CTG | GAG | GTG | GCC | 1512 |
|---|---|---|---|---|---|---|---|---|---|---|---|---|---|---|---|---|
| Val | Arg<br>450 | Leu | Asp | Val | Ala | Tyr<br>455 | Leu | Arg | Ala | Leu | Ser<br>460 | Leu | Glu | Val | Ala | |

| GAG | GAG | ATC | GCC | CGC | CTC | GAG | GCC | GAG | GTC | TTC | CGC | CTG | GCC | GGC | CAC | 1560 |
|---|---|---|---|---|---|---|---|---|---|---|---|---|---|---|---|---|
| Glu<br>465 | Glu | Ile | Ala | Arg | Leu<br>470 | Glu | Ala | Glu | Val | Phe<br>475 | Arg | Leu | Ala | Gly | His<br>480 | |

| CCC | TTC | AAC | CTC | AAC | TCC | CGG | GAC | CAG | CTG | GAA | AGG | GTC | CTC | TTT | GAC | 1608 |
|---|---|---|---|---|---|---|---|---|---|---|---|---|---|---|---|---|
| Pro | Phe | Asn | Leu | Asn<br>485 | Ser | Arg | Asp | Gln | Leu<br>490 | Glu | Arg | Val | Leu | Phe<br>495 | Asp | |

| GAG | CTA | GGG | CTT | CCC | GCC | ATC | GGC | AAG | ACG | GAG | AAG | ACC | GGC | AAG | CGC | 1656 |
|---|---|---|---|---|---|---|---|---|---|---|---|---|---|---|---|---|
| Glu | Leu | Gly | Leu<br>500 | Pro | Ala | Ile | Gly | Lys<br>505 | Thr | Glu | Lys | Thr | Gly<br>510 | Lys | Arg | |

| TCC | ACC | AGC | GCC | GCC | GTC | CTG | GAG | GCC | CTC | CGC | GAG | GCC | CAC | CCC | ATC | 1704 |
|---|---|---|---|---|---|---|---|---|---|---|---|---|---|---|---|---|
| Ser | Thr | Ser<br>515 | Ala | Ala | Val | Leu | Glu<br>520 | Ala | Leu | Arg | Glu | Ala<br>525 | His | Pro | Ile | |

| GTG | GAG | AAG | ATC | CTG | CAG | TAC | CGG | GAG | CTC | ACC | AAG | CTG | AAG | AGC | ACC | 1752 |
|---|---|---|---|---|---|---|---|---|---|---|---|---|---|---|---|---|
| Val | Glu<br>530 | Lys | Ile | Leu | Gln | Tyr<br>535 | Arg | Glu | Leu | Thr | Lys<br>540 | Leu | Lys | Ser | Thr | |

| TAC | ATT | GAC | CCC | TTG | CCG | GAC | CTC | ATC | CAC | CCC | AGG | ACG | GGC | CGC | CTC | 1800 |
|---|---|---|---|---|---|---|---|---|---|---|---|---|---|---|---|---|
| Tyr<br>545 | Ile | Asp | Pro | Leu | Pro<br>550 | Asp | Leu | Ile | His | Pro<br>555 | Arg | Thr | Gly | Arg | Leu<br>560 | |

| CAC | ACC | CGC | TTC | AAC | CAG | ACG | GCC | ACG | GCC | ACG | GGC | AGG | CTA | AGT | AGC | 1848 |
|---|---|---|---|---|---|---|---|---|---|---|---|---|---|---|---|---|
| His | Thr | Arg | Phe | Asn<br>565 | Gln | Thr | Ala | Thr | Ala<br>570 | Thr | Gly | Arg | Leu | Ser<br>575 | Ser | |

| TCC | GAT | CCC | AAC | CTC | CAG | AAC | ATC | CCC | GTC | CGC | ACC | CCG | CTT | GGG | CAG | 1896 |
|---|---|---|---|---|---|---|---|---|---|---|---|---|---|---|---|---|
| Ser | Asp | Pro | Asn<br>580 | Leu | Gln | Asn | Ile | Pro<br>585 | Val | Arg | Thr | Pro | Leu<br>590 | Gly | Gln | |

| AGG | ATC | CGC | CGG | GCC | TTC | ATC | GCC | GAG | GAG | GGG | TGG | CTA | TTG | GTG | GCC | 1944 |
|---|---|---|---|---|---|---|---|---|---|---|---|---|---|---|---|---|
| Arg | Ile | Arg<br>595 | Arg | Ala | Phe | Ile | Ala<br>600 | Glu | Glu | Gly | Trp | Leu<br>605 | Leu | Val | Ala | |

| CTG | GAC | TAT | AGC | CAG | ATA | GAG | CTC | AGG | GTG | CTG | GCC | CAC | CTC | TCC | GGC | 1992 |
|---|---|---|---|---|---|---|---|---|---|---|---|---|---|---|---|---|
| Leu | Asp<br>610 | Tyr | Ser | Gln | Ile | Glu<br>615 | Leu | Arg | Val | Leu | Ala<br>620 | His | Leu | Ser | Gly | |

| GAC | GAG | AAC | CTG | ATC | CGG | GTC | TTC | CAG | GAG | GGG | CGG | GAC | ATC | CAC | ACG | 2040 |
|---|---|---|---|---|---|---|---|---|---|---|---|---|---|---|---|---|
| Asp<br>625 | Glu | Asn | Leu | Ile | Arg<br>630 | Val | Phe | Gln | Glu | Gly<br>635 | Arg | Asp | Ile | His | Thr<br>640 | |

| GAG | ACC | GCC | AGC | TGG | ATG | TTC | GGC | GTC | CCC | CGG | GAG | GCC | GTG | GAC | CCC | 2088 |
|---|---|---|---|---|---|---|---|---|---|---|---|---|---|---|---|---|
| Glu | Thr | Ala | Ser | Trp<br>645 | Met | Phe | Gly | Val | Pro<br>650 | Arg | Glu | Ala | Val | Asp<br>655 | Pro | |

| CTG | ATG | CGC | CGG | GCG | GCC | AAG | ACC | ATC | AAC | TTC | GGG | GTC | CTC | TAC | GGC | 2136 |
|---|---|---|---|---|---|---|---|---|---|---|---|---|---|---|---|---|
| Leu | Met | Arg | Arg<br>660 | Ala | Ala | Lys | Thr | Ile<br>665 | Asn | Phe | Gly | Val | Leu<br>670 | Tyr | Gly | |

| ATG | TCG | GCC | CAC | CGC | CTC | TCC | CAG | GAG | CTA | GCC | ATC | CCT | TAC | GAG | GAG | 2184 |
|---|---|---|---|---|---|---|---|---|---|---|---|---|---|---|---|---|
| Met | Ser | Ala | His<br>675 | Arg | Leu | Ser | Gln | Glu<br>680 | Leu | Ala | Ile | Pro | Tyr<br>685 | Glu | Glu | |

| GCC | CAG | GCC | TTC | ATT | GAG | CGC | TAC | TTT | CAG | AGC | TTC | CCC | AAG | GTG | CGG | 2232 |
|---|---|---|---|---|---|---|---|---|---|---|---|---|---|---|---|---|
| Ala | Gln | Ala<br>690 | Phe | Ile | Glu | Arg | Tyr<br>695 | Phe | Gln | Ser | Phe | Pro<br>700 | Lys | Val | Arg | |

| GCC | TGG | ATT | GAG | AAG | ACC | CTG | GAG | GAG | GGC | AGG | AGG | CGG | GGG | TAC | GTG | 2280 |
|---|---|---|---|---|---|---|---|---|---|---|---|---|---|---|---|---|
| Ala<br>705 | Trp | Ile | Glu | Lys | Thr<br>710 | Leu | Glu | Glu | Gly | Arg<br>715 | Arg | Arg | Gly | Tyr<br>720 | Val | |

| | | | | | | | | | | | | | | | | |
|---|---|---|---|---|---|---|---|---|---|---|---|---|---|---|---|---|
| GAG | ACC | CTC | TTC | GGC | CGC | CGC | CGC | TAC | GTG | CCA | GAC | CTA | GAG | GCC | CGG | 2328 |
| Glu | Thr | Leu | Phe | Gly 725 | Arg | Arg | Arg | Tyr | Val 730 | Pro | Asp | Leu | Glu | Ala 735 | Arg | |
| GTG | AAG | AGC | GTG | CGG | GAG | GCG | GCC | GAG | CGC | ATG | GCC | TTC | AAC | ATG | CCC | 2376 |
| Val | Lys | Ser | Val 740 | Arg | Glu | Ala | Ala | Glu 745 | Arg | Met | Ala | Phe | Asn 750 | Met | Pro | |
| GTC | CAG | GGC | ACC | GCC | GCC | GAC | CTC | ATG | AAG | CTG | GCT | ATG | GTG | AAG | CTC | 2424 |
| Val | Gln | Gly 755 | Thr | Ala | Ala | Asp | Leu | Met 760 | Lys | Leu | Ala | Met 765 | Val | Lys | Leu | |
| TTC | CCC | AGG | CTG | GAG | GAA | ATG | GGG | GCC | AGG | ATG | CTC | CTT | CAG | GTC | CAC | 2472 |
| Phe | Pro 770 | Arg | Leu | Glu | Glu | Met 775 | Gly | Ala | Arg | Met | Leu 780 | Leu | Gln | Val | His | |
| GAC | GAG | CTG | GTC | CTC | GAG | GCC | CCA | AAA | GAG | AGG | GCG | GAG | GCC | GTG | GCC | 2520 |
| Asp 785 | Glu | Leu | Val | Leu | Glu 790 | Ala | Pro | Lys | Glu | Arg 795 | Ala | Glu | Ala | Val | Ala 800 | |
| CGG | CTG | GCC | AAG | GAA | GTC | ATG | GAG | GGG | GTG | TAT | CCC | CTG | GCC | GTG | CCC | 2568 |
| Arg | Leu | Ala | Lys | Glu 805 | Val | Met | Glu | Gly | Val 810 | Tyr | Pro | Leu | Ala | Val 815 | Pro | |
| CTG | GAG | GTG | GAG | GTG | GGG | ATA | GGG | GAG | GAC | TGG | CTC | TCC | GCC | AAG | GAG | 2616 |
| Leu | Glu | Val | Glu 820 | Val | Gly | Ile | Gly | Glu 825 | Asp | Trp | Leu | Ser | Ala 830 | Lys | Glu | |
| TGATACCACC | | | | | | | | | | | | | | | | 2626 |

( 2 ) INFORMATION FOR SEQ ID NO:6:

( i ) SEQUENCE CHARACTERISTICS:
        ( A ) LENGTH: 832 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
| Met 1 | Arg | Gly | Met | Leu 5 | Pro | Leu | Phe | Glu | Pro 10 | Lys | Gly | Arg | Val | Leu 15 | Leu |
| Val | Asp | Gly | His 20 | His | Leu | Ala | Tyr | Cys 25 | Thr | Phe | His | Ala | Leu 30 | Lys | Gly |
| Leu | Thr | Thr 35 | Ser | Arg | Gly | Glu | Pro 40 | Val | Gln | Ala | Val | Tyr 45 | Gly | Phe | Ala |
| Lys | Ser 50 | Leu | Leu | Lys | Ala | Leu 55 | Lys | Glu | Asp | Gly | Asp 60 | Ala | Val | Ile | Val |
| Val 65 | Phe | Asp | Ala | Lys | Ala 70 | Pro | Ser | Phe | Arg | His 75 | Glu | Ala | Tyr | Gly | Gly 80 |
| Tyr | Lys | Ala | Gly | Arg 85 | Ala | Pro | Thr | Pro | Glu 90 | Asp | Phe | Pro | Arg | Gln 95 | Leu |
| Ala | Leu | Ile | Lys 100 | Glu | Leu | Val | Asp | Leu 105 | Leu | Gly | Leu | Ala | Arg 110 | Leu | Glu |
| Val | Pro | Gly 115 | Tyr | Glu | Ala | Asp | Asp 120 | Val | Leu | Ala | Ser | Leu 125 | Ala | Lys | Lys |
| Ala | Glu 130 | Lys | Glu | Gly | Tyr | Glu 135 | Val | Arg | Ile | Leu | Thr 140 | Ala | Asp | Lys | Asp |
| Leu 145 | Tyr | Gln | Leu | Leu | Ser 150 | Asp | Arg | Ile | His | Val 155 | Leu | His | Pro | Glu | Gly 160 |
| Tyr | Leu | Ile | Thr | Pro 165 | Ala | Trp | Leu | Trp | Glu 170 | Lys | Tyr | Gly | Leu | Arg 175 | Pro |
| Asp | Gln | Trp | Ala 180 | Asp | Tyr | Arg | Ala | Leu 185 | Thr | Gly | Asp | Glu | Ser 190 | Asp | Asn |
| Leu | Pro | Gly | Val | Lys | Gly | Ile | Gly | Glu | Lys | Thr | Ala | Arg | Lys | Leu | Leu |

```
                195                    200                    205
Glu Glu Trp Gly Ser Leu Glu Ala Leu Leu Lys Asn Leu Asp Arg Leu
    210                    215                    220

Lys Pro Ala Ile Arg Glu Lys Ile Leu Ala His Met Asp Asp Leu Lys
225                    230                    235                    240

Leu Ser Trp Asp Leu Ala Lys Val Arg Thr Asp Leu Pro Leu Glu Val
                245                    250                    255

Asp Phe Ala Lys Arg Arg Glu Pro Asp Arg Glu Arg Leu Arg Ala Ile
            260                    265                    270

Leu Glu Arg Leu Glu Phe Gly Ser Pro Leu His Glu Phe Gly Leu Leu
        275                    280                    285

Glu Ser Pro Lys Ala Leu Glu Ala Pro Trp Pro Pro Pro Glu Gly
    290                    295                    300

Ala Phe Val Gly Phe Val Leu Ser Arg Lys Glu Pro Met Trp Ala Asp
305                    310                    315                    320

Leu Leu Ala Leu Ala Ala Ala Arg Gly Gly Arg Val His Arg Ala Pro
                325                    330                    335

Glu Pro Tyr Lys Ala Leu Arg Asp Leu Lys Glu Ala Arg Gly Leu Leu
            340                    345                    350

Ala Lys Asp Leu Ser Val Leu Ala Leu Arg Glu Gly Leu Gly Leu Pro
        355                    360                    365

Pro Gly Asp Asp Pro Met Leu Leu Ala Tyr Leu Leu Asp Pro Ser Asn
    370                    375                    380

Thr Thr Pro Glu Gly Val Ala Arg Arg Tyr Gly Gly Glu Trp Thr Glu
385                    390                    395                    400

Glu Ala Gly Glu Arg Ala Ala Leu Ser Glu Arg Leu Phe Ala Asn Leu
                405                    410                    415

Trp Gly Arg Leu Glu Gly Glu Glu Arg Leu Leu Trp Leu Tyr Arg Glu
            420                    425                    430

Val Glu Arg Pro Leu Ser Ala Val Leu Ala His Met Glu Ala Thr Gly
        435                    440                    445

Val Arg Leu Asp Val Ala Tyr Leu Arg Ala Leu Ser Leu Glu Val Ala
    450                    455                    460

Glu Glu Ile Ala Arg Leu Glu Ala Glu Val Phe Arg Leu Ala Gly His
465                    470                    475                    480

Pro Phe Asn Leu Asn Ser Arg Asp Gln Leu Glu Arg Val Leu Phe Asp
                485                    490                    495

Glu Leu Gly Leu Pro Ala Ile Gly Lys Thr Glu Lys Thr Gly Lys Arg
            500                    505                    510

Ser Thr Ser Ala Ala Val Leu Glu Ala Leu Arg Glu Ala His Pro Ile
        515                    520                    525

Val Glu Lys Ile Leu Gln Tyr Arg Glu Leu Thr Lys Leu Lys Ser Thr
    530                    535                    540

Tyr Ile Asp Pro Leu Pro Asp Leu Ile His Pro Arg Thr Gly Arg Leu
545                    550                    555                    560

His Thr Arg Phe Asn Gln Thr Ala Thr Ala Thr Gly Arg Leu Ser Ser
                565                    570                    575

Ser Asp Pro Asn Leu Gln Asn Ile Pro Val Arg Thr Pro Leu Gly Gln
            580                    585                    590

Arg Ile Arg Arg Ala Phe Ile Ala Glu Glu Gly Trp Leu Leu Val Ala
        595                    600                    605

Leu Asp Tyr Ser Gln Ile Glu Leu Arg Val Leu Ala His Leu Ser Gly
    610                    615                    620
```

| | | | | | | | | | | | | | | |
|---|---|---|---|---|---|---|---|---|---|---|---|---|---|---|
| Asp 625 | Glu | Asn | Leu | Ile | Arg 630 | Val | Phe | Gln | Glu 635 | Gly | Arg | Asp | Ile | His | Thr 640 |
| Glu | Thr | Ala | Ser | Trp 645 | Met | Phe | Gly | Val | Pro 650 | Arg | Glu | Ala | Val | Asp 655 | Pro |
| Leu | Met | Arg | Arg 660 | Ala | Ala | Lys | Thr | Ile 665 | Asn | Phe | Gly | Val | Leu 670 | Tyr | Gly |
| Met | Ser | Ala 675 | His | Arg | Leu | Ser | Gln 680 | Glu | Leu | Ala | Ile | Pro 685 | Tyr | Glu | Glu |
| Ala | Gln 690 | Ala | Phe | Ile | Glu | Arg 695 | Tyr | Phe | Gln | Ser | Phe 700 | Pro | Lys | Val | Arg |
| Ala 705 | Trp | Ile | Glu | Lys | Thr 710 | Leu | Glu | Glu | Gly | Arg 715 | Arg | Arg | Gly | Tyr | Val 720 |
| Glu | Thr | Leu | Phe | Gly 725 | Arg | Arg | Arg | Tyr | Val 730 | Pro | Asp | Leu | Glu | Ala 735 | Arg |
| Val | Lys | Ser | Val 740 | Arg | Glu | Ala | Ala | Glu 745 | Arg | Met | Ala | Phe | Asn 750 | Met | Pro |
| Val | Gln | Gly 755 | Thr | Ala | Ala | Asp | Leu 760 | Met | Lys | Leu | Ala | Met 765 | Val | Lys | Leu |
| Phe | Pro 770 | Arg | Leu | Glu | Glu | Met 775 | Gly | Ala | Arg | Met | Leu 780 | Leu | Gln | Val | His |
| Asp 785 | Glu | Leu | Val | Leu | Glu 790 | Ala | Pro | Lys | Glu | Arg 795 | Ala | Glu | Ala | Val | Ala 800 |
| Arg | Leu | Ala | Lys | Glu 805 | Val | Met | Glu | Gly | Val 810 | Tyr | Pro | Leu | Ala | Val 815 | Pro |
| Leu | Glu | Val | Glu 820 | Val | Gly | Ile | Gly | Glu 825 | Asp | Trp | Leu | Ser | Ala 830 | Lys | Glu |

( 2 ) INFORMATION FOR SEQ ID NO:7:

( i ) SEQUENCE CHARACTERISTICS:
        ( A ) LENGTH: 2626 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Thermus aquaticus ( i x ) FEATURE:
        ( A ) NAME/KEY: mutation
        ( B ) LOCATION: replace(89, "g")
        ( D ) OTHER INFORMATION: /note="This mutation results in a
            nucleotide alteration at postion 89 of the native Taq
            DNA polymerase nucleotide sequence of C to G."

( i x ) FEATURE:
        ( A ) NAME/KEY: mutation
        ( B ) LOCATION: replace(934, "a")
        ( D ) OTHER INFORMATION: /note="This mutation results in a
            nucleotide alteration at position 934 of the native Taq
            DNA polymerase nucleotide sequence of T to A. This
            results in an amino acid change of Phe to Ile."

( i x ) FEATURE:
        ( A ) NAME/KEY: mutation
        ( B ) LOCATION: replace(962, "c")
        ( D ) OTHER INFORMATION: /note="This mutation results in a
            nucleotide alteration at position 962 of the native Taq
            DNA polymerase nucleotide sequence of T to C. This results in an amino acid change of Leu to Pro."

( i x ) FEATURE:
    ( A ) NAME/KEY: mutation
    ( B ) LOCATION: replace(2535, "a")
    ( D ) OTHER INFORMATION: /note="This mutation results in a
        nucleotide alteration at position 2535 of the native
        Taq DNA polymerase nucleotide sequence of G to A. This
        mutation is conservative."

( i x ) FEATURE:
    ( A ) NAME/KEY: mutation
    ( B ) LOCATION: replace(341, "a")
    ( D ) OTHER INFORMATION: /note="This mutation results in a
        nucleotide alteration at position 341 of the native Taq
        DNA polymerase nucleotide sequence of G to A. This
        mutation results in an amino acid change of Arg to His."

( i x ) FEATURE:
    ( A ) NAME/KEY: CDS
    ( B ) LOCATION: 121..2619

( i x ) FEATURE:
    ( A ) NAME/KEY: mat_peptide
    ( B ) LOCATION: 121..2616

( i x ) FEATURE:
    ( A ) NAME/KEY: -
    ( B ) LOCATION: 1..2619
    ( D ) OTHER INFORMATION: /note="pTarf5"

( x i ) SEQUENCE DESCRIPTION: SEQ ID NO:7:

```
AAGCTCAGAT  CTACCTGCCT  GAGGGCGTCC  GGTTCCAGCT  GGCCCTTCCC  GAGGGGAGA        60

GGGAGGCGTT  TCTAAAAGCC  CTTCAGGAGG  CTACCCGGGG  GCGGGTGGTG  GAAGGGTAAC      120

ATG  AGG  GGG  ATG  CTG  CCC  CTC  TTT  GAG  CCC  AAG  GGC  CGG  GTC  CTG  CTG    168
Met  Arg  Gly  Met  Leu  Pro  Leu  Phe  Glu  Pro  Lys  Gly  Arg  Val  Leu  Leu
 1              5                       10                      15

GTG  GAC  GGC  CAC  CAC  CTG  GCC  TAC  CGC  ACC  TTC  CAC  GCC  CTG  AAG  GGC    216
Val  Asp  Gly  His  His  Leu  Ala  Tyr  Arg  Thr  Phe  His  Ala  Leu  Lys  Gly
             20                      25                      30

CTC  ACC  ACC  AGC  CGG  GGG  GAG  CCG  GTG  CAG  GCG  GTC  TAC  GGC  TTC  GCC    264
Leu  Thr  Thr  Ser  Arg  Gly  Glu  Pro  Val  Gln  Ala  Val  Tyr  Gly  Phe  Ala
         35                      40                      45

AAG  AGC  CTC  CTC  AAG  GCC  CTC  AAG  GAG  GAC  GGG  GAC  GCG  GTG  ATC  GTG    312
Lys  Ser  Leu  Leu  Lys  Ala  Leu  Lys  Glu  Asp  Gly  Asp  Ala  Val  Ile  Val
     50                      55                      60

GTC  TTT  GAC  GCC  AAG  GCC  CCC  TCC  TTC  CAC  CAC  GAG  GCC  TAC  GGG  GGG    360
Val  Phe  Asp  Ala  Lys  Ala  Pro  Ser  Phe  His  His  Glu  Ala  Tyr  Gly  Gly
 65                      70                      75                      80

TAC  AAG  GCG  GGC  CGG  GCC  CCC  ACG  CCG  GAG  GAC  TTT  CCC  CGG  CAA  CTC    408
Tyr  Lys  Ala  Gly  Arg  Ala  Pro  Thr  Pro  Glu  Asp  Phe  Pro  Arg  Gln  Leu
                 85                      90                      95

GCC  CTC  ATC  AAG  GAG  CTG  GTG  GAC  CTC  CTG  GGG  CTG  GCG  CGC  CTC  GAG    456
Ala  Leu  Ile  Lys  Glu  Leu  Val  Asp  Leu  Leu  Gly  Leu  Ala  Arg  Leu  Glu
             100                     105                     110

GTC  CCG  GGC  TAC  GAG  GCG  GAC  GAC  GTC  CTG  GCC  AGC  CTG  GCC  AAG  AAG    504
Val  Pro  Gly  Tyr  Glu  Ala  Asp  Asp  Val  Leu  Ala  Ser  Leu  Ala  Lys  Lys
         115                     120                     125

GCG  GAA  AAG  GAG  GGC  TAC  GAG  GTC  CGC  ATC  CTC  ACC  GCC  GAC  AAA  GAC    552
Ala  Glu  Lys  Glu  Gly  Tyr  Glu  Val  Arg  Ile  Leu  Thr  Ala  Asp  Lys  Asp
     130                     135                     140

CTT  TAC  CAG  CTC  CTT  TCC  GAC  CGC  ATC  CAC  GTC  CTC  CAC  CCC  GAG  GGG    600
Leu  Tyr  Gln  Leu  Leu  Ser  Asp  Arg  Ile  His  Val  Leu  His  Pro  Glu  Gly
145                     150                     155                     160

TAC  CTC  ATC  ACC  CCG  GCC  TGG  CTT  TGG  GAA  AAG  TAC  GGC  CTG  AGG  CCC    648
Tyr  Leu  Ile  Thr  Pro  Ala  Trp  Leu  Trp  Glu  Lys  Tyr  Gly  Leu  Arg  Pro
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 165 |     |     |     |     | 170 |     |     |     |     | 175 |     |      |
| GAC | CAG | TGG | GCC | GAC | TAC | CGG | GCC | CTG | ACC | GGG | GAC | GAG | TCC | GAC | AAC | 696  |
| Asp | Gln | Trp | Ala | Asp | Tyr | Arg | Ala | Leu | Thr | Gly | Asp | Glu | Ser | Asp | Asn |      |
|     |     |     | 180 |     |     |     |     | 185 |     |     |     |     | 190 |     |     |      |
| CTT | CCC | GGG | GTC | AAG | GGC | ATC | GGG | GAG | AAG | ACG | GCG | AGG | AAG | CTT | CTG | 744  |
| Leu | Pro | Gly | Val | Lys | Gly | Ile | Gly | Glu | Lys | Thr | Ala | Arg | Lys | Leu | Leu |      |
|     |     | 195 |     |     |     |     | 200 |     |     |     |     | 205 |     |     |     |      |
| GAG | GAG | TGG | GGG | AGC | CTG | GAA | GCC | CTC | CTC | AAG | AAC | CTG | GAC | CGG | CTG | 792  |
| Glu | Glu | Trp | Gly | Ser | Leu | Glu | Ala | Leu | Leu | Lys | Asn | Leu | Asp | Arg | Leu |      |
|     | 210 |     |     |     |     | 215 |     |     |     |     | 220 |     |     |     |     |      |
| AAG | CCC | GCC | ATC | CGG | GAG | AAG | ATC | CTG | GCC | CAC | ATG | GAC | GAT | CTG | AAG | 840  |
| Lys | Pro | Ala | Ile | Arg | Glu | Lys | Ile | Leu | Ala | His | Met | Asp | Asp | Leu | Lys |      |
| 225 |     |     |     |     | 230 |     |     |     |     | 235 |     |     |     |     | 240 |      |
| CTC | TCC | TGG | GAC | CTG | GCC | AAG | GTG | CGC | ACC | GAC | CTG | CCC | CTG | GAG | GTG | 888  |
| Leu | Ser | Trp | Asp | Leu | Ala | Lys | Val | Arg | Thr | Asp | Leu | Pro | Leu | Glu | Val |      |
|     |     |     |     | 245 |     |     |     |     | 250 |     |     |     |     | 255 |     |      |
| GAC | TTC | GCC | AAA | AGG | CGG | GAG | CCC | GAC | CGG | GAG | AGG | CTT | AGG | GCC | ATT | 936  |
| Asp | Phe | Ala | Lys | Arg | Arg | Glu | Pro | Asp | Arg | Glu | Arg | Leu | Arg | Ala | Ile |      |
|     |     |     | 260 |     |     |     |     | 265 |     |     |     |     | 270 |     |     |      |
| CTG | GAG | AGG | CTT | GAG | TTT | GGC | AGC | CCC | CTC | CAC | GAG | TTC | GGC | CTT | CTG | 984  |
| Leu | Glu | Arg | Leu | Glu | Phe | Gly | Ser | Pro | Leu | His | Glu | Phe | Gly | Leu | Leu |      |
|     |     | 275 |     |     |     |     | 280 |     |     |     |     | 285 |     |     |     |      |
| GAA | AGC | CCC | AAG | GCC | CTG | GAG | GAG | GCC | CCC | TGG | CCC | CCG | CCG | GAA | GGG | 1032 |
| Glu | Ser | Pro | Lys | Ala | Leu | Glu | Glu | Ala | Pro | Trp | Pro | Pro | Pro | Glu | Gly |      |
|     | 290 |     |     |     |     | 295 |     |     |     |     | 300 |     |     |     |     |      |
| GCC | TTC | GTG | GGC | TTT | GTG | CTT | TCC | CGC | AAG | GAG | CCC | ATG | TGG | GCC | GAT | 1080 |
| Ala | Phe | Val | Gly | Phe | Val | Leu | Ser | Arg | Lys | Glu | Pro | Met | Trp | Ala | Asp |      |
| 305 |     |     |     |     | 310 |     |     |     |     | 315 |     |     |     |     | 320 |      |
| CTT | CTG | GCC | CTG | GCC | GCC | GCC | AGG | GGG | GGC | CGG | GTC | CAC | CGG | GCC | CCC | 1128 |
| Leu | Leu | Ala | Leu | Ala | Ala | Ala | Arg | Gly | Gly | Arg | Val | His | Arg | Ala | Pro |      |
|     |     |     |     | 325 |     |     |     |     | 330 |     |     |     |     | 335 |     |      |
| GAG | CCT | TAT | AAA | GCC | CTC | AGG | GAC | CTG | AAG | GAG | GCG | CGG | GGG | CTT | CTC | 1176 |
| Glu | Pro | Tyr | Lys | Ala | Leu | Arg | Asp | Leu | Lys | Glu | Ala | Arg | Gly | Leu | Leu |      |
|     |     |     | 340 |     |     |     |     | 345 |     |     |     |     | 350 |     |     |      |
| GCC | AAA | GAC | CTG | AGC | GTT | CTG | GCC | CTG | AGG | GAA | GGC | CTT | GGC | CTC | CCG | 1224 |
| Ala | Lys | Asp | Leu | Ser | Val | Leu | Ala | Leu | Arg | Glu | Gly | Leu | Gly | Leu | Pro |      |
|     |     | 355 |     |     |     |     | 360 |     |     |     |     | 365 |     |     |     |      |
| CCC | GGC | GAC | GAC | CCC | ATG | CTC | CTC | GCC | TAC | CTC | CTG | GAC | CCT | TCC | AAC | 1272 |
| Pro | Gly | Asp | Asp | Pro | Met | Leu | Leu | Ala | Tyr | Leu | Leu | Asp | Pro | Ser | Asn |      |
|     | 370 |     |     |     |     | 375 |     |     |     |     | 380 |     |     |     |     |      |
| ACC | ACC | CCC | GAG | GGG | GTG | GCC | CGG | CGC | TAC | GGC | GGG | GAG | TGG | ACG | GAG | 1320 |
| Thr | Thr | Pro | Glu | Gly | Val | Ala | Arg | Arg | Tyr | Gly | Gly | Glu | Trp | Thr | Glu |      |
| 385 |     |     |     |     | 390 |     |     |     |     | 395 |     |     |     |     | 400 |      |
| GAG | GCG | GGG | GAG | CGG | GCC | GCC | CTT | TCC | GAG | AGG | CTC | TTC | GCC | AAC | CTG | 1368 |
| Glu | Ala | Gly | Glu | Arg | Ala | Ala | Leu | Ser | Glu | Arg | Leu | Phe | Ala | Asn | Leu |      |
|     |     |     |     | 405 |     |     |     |     | 410 |     |     |     |     | 415 |     |      |
| TGG | GGG | AGG | CTT | GAG | GGG | GAG | GAG | AGG | CTC | CTT | TGG | CTT | TAC | CGG | GAG | 1416 |
| Trp | Gly | Arg | Leu | Glu | Gly | Glu | Glu | Arg | Leu | Leu | Trp | Leu | Tyr | Arg | Glu |      |
|     |     |     | 420 |     |     |     |     | 425 |     |     |     |     | 430 |     |     |      |
| GTG | GAG | AGG | CCC | CTT | TCC | GCT | GTC | CTG | GCC | CAC | ATG | GAG | GCC | ACG | GGG | 1464 |
| Val | Glu | Arg | Pro | Leu | Ser | Ala | Val | Leu | Ala | His | Met | Glu | Ala | Thr | Gly |      |
|     |     | 435 |     |     |     |     | 440 |     |     |     |     | 445 |     |     |     |      |
| GTG | CGC | CTG | GAC | GTG | GCC | TAT | CTC | AGG | GCC | TTG | TCC | CTG | GAG | GTG | GCC | 1512 |
| Val | Arg | Leu | Asp | Val | Ala | Tyr | Leu | Arg | Ala | Leu | Ser | Leu | Glu | Val | Ala |      |
|     | 450 |     |     |     |     | 455 |     |     |     |     | 460 |     |     |     |     |      |
| GAG | GAG | ATC | GCC | CGC | CTC | GAG | GCC | GAG | GTC | TTC | CGC | CTG | GCC | GGC | CAC | 1560 |
| Glu | Glu | Ile | Ala | Arg | Leu | Glu | Ala | Glu | Val | Phe | Arg | Leu | Ala | Gly | His |      |
| 465 |     |     |     |     | 470 |     |     |     |     | 475 |     |     |     |     | 480 |      |
| CCC | TTC | AAC | CTC | AAC | TCC | CGG | GAC | CAG | CTG | GAA | AGG | GTC | CTC | TTT | GAC | 1608 |

| | | | | | | | | | | | | | | | | |
|---|---|---|---|---|---|---|---|---|---|---|---|---|---|---|---|---|
| Pro | Phe | Asn | Leu | Asn<br>485 | Ser | Arg | Asp | Gln | Leu<br>490 | Glu | Arg | Val | Leu | Phe<br>495 | Asp | |
| GAG<br>Glu | CTA<br>Leu | GGG<br>Gly | CTT<br>Leu<br>500 | CCC<br>Pro | GCC<br>Ala | ATC<br>Ile | GGC<br>Gly | AAG<br>Lys<br>505 | ACG<br>Thr | GAG<br>Glu | AAG<br>Lys | ACC<br>Thr | GGC<br>Gly<br>510 | AAG<br>Lys | CGC<br>Arg | 1656 |
| TCC<br>Ser | ACC<br>Thr | AGC<br>Ser<br>515 | GCC<br>Ala | GCC<br>Ala | GTC<br>Val | CTG<br>Leu | GAG<br>Glu<br>520 | GCC<br>Ala | CTC<br>Leu | CGC<br>Arg | GAG<br>Glu | GCC<br>Ala<br>525 | CAC<br>His | CCC<br>Pro | ATC<br>Ile | 1704 |
| GTG<br>Val | GAG<br>Glu<br>530 | AAG<br>Lys | ATC<br>Ile | CTG<br>Leu | CAG<br>Gln | TAC<br>Tyr<br>535 | CGG<br>Arg | GAG<br>Glu | CTC<br>Leu | ACC<br>Thr | AAG<br>Lys<br>540 | CTG<br>Leu | AAG<br>Lys | AGC<br>Ser | ACC<br>Thr | 1752 |
| TAC<br>Tyr<br>545 | ATT<br>Ile | GAC<br>Asp | CCC<br>Pro | TTG<br>Leu<br>550 | CCG<br>Pro | GAC<br>Asp | CTC<br>Leu | ATC<br>Ile | CAC<br>His<br>555 | CCC<br>Pro | AGG<br>Arg | ACG<br>Thr | GGC<br>Gly | CGC<br>Arg<br>560 | CTC<br>Leu | 1800 |
| CAC<br>His | ACC<br>Thr | CGC<br>Arg | TTC<br>Phe | AAC<br>Asn<br>565 | CAG<br>Gln | ACG<br>Thr | GCC<br>Ala | ACG<br>Thr | GCC<br>Ala<br>570 | ACG<br>Thr | GGC<br>Gly | AGG<br>Arg | CTA<br>Leu | AGT<br>Ser<br>575 | AGC<br>Ser | 1848 |
| TCC<br>Ser | GAT<br>Asp | CCC<br>Pro | AAC<br>Asn<br>580 | CTC<br>Leu | CAG<br>Gln | AAC<br>Asn | ATC<br>Ile | CCC<br>Pro<br>585 | GTC<br>Val | CGC<br>Arg | ACC<br>Thr | CCG<br>Pro | CTT<br>Leu<br>590 | GGG<br>Gly | CAG<br>Gln | 1896 |
| AGG<br>Arg | ATC<br>Ile | CGC<br>Arg<br>595 | CGG<br>Arg | GCC<br>Ala | TTC<br>Phe | ATC<br>Ile | GCC<br>Ala<br>600 | GAG<br>Glu | GAG<br>Glu | GGG<br>Gly | TGG<br>Trp | CTA<br>Leu<br>605 | TTG<br>Leu | GTG<br>Val | GCC<br>Ala | 1944 |
| CTG<br>Leu | GAC<br>Asp<br>610 | TAT<br>Tyr | AGC<br>Ser | CAG<br>Gln | ATA<br>Ile<br>615 | GAG<br>Glu | CTC<br>Leu | AGG<br>Arg | GTG<br>Val | CTG<br>Leu<br>620 | GCC<br>Ala | CAC<br>His | CTC<br>Leu | TCC<br>Ser | GGC<br>Gly | 1992 |
| GAC<br>Asp<br>625 | GAG<br>Glu | AAC<br>Asn | CTG<br>Leu | ATC<br>Ile | CGG<br>Arg<br>630 | GTC<br>Val | TTC<br>Phe | CAG<br>Gln | GAG<br>Glu | GGG<br>Gly<br>635 | CGG<br>Arg | GAC<br>Asp | ATC<br>Ile | CAC<br>His | ACG<br>Thr<br>640 | 2040 |
| GAG<br>Glu | ACC<br>Thr | GCC<br>Ala | AGC<br>Ser | TGG<br>Trp<br>645 | ATG<br>Met | TTC<br>Phe | GGC<br>Gly | GTC<br>Val | CCC<br>Pro<br>650 | CGG<br>Arg | GAG<br>Glu | GCC<br>Ala | GTG<br>Val | GAC<br>Asp<br>655 | CCC<br>Pro | 2088 |
| CTG<br>Leu | ATG<br>Met | CGC<br>Arg | CGG<br>Arg<br>660 | GCG<br>Ala | GCC<br>Ala | AAG<br>Lys | ACC<br>Thr | ATC<br>Ile<br>665 | AAC<br>Asn | TTC<br>Phe | GGG<br>Gly | GTC<br>Val | CTC<br>Leu<br>670 | TAC<br>Tyr | GGC<br>Gly | 2136 |
| ATG<br>Met | TCG<br>Ser | GCC<br>Ala<br>675 | CAC<br>His | CGC<br>Arg | CTC<br>Leu | TCC<br>Ser | CAG<br>Gln<br>680 | GAG<br>Glu | CTA<br>Leu | GCC<br>Ala | ATC<br>Ile | CCT<br>Pro<br>685 | TAC<br>Tyr | GAG<br>Glu | GAG<br>Glu | 2184 |
| GCC<br>Ala | CAG<br>Gln<br>690 | GCC<br>Ala | TTC<br>Phe | ATT<br>Ile | GAG<br>Glu<br>695 | CGC<br>Arg | TAC<br>Tyr | TTT<br>Phe | CAG<br>Gln | AGC<br>Ser<br>700 | TTC<br>Phe | CCC<br>Pro | AAG<br>Lys | GTG<br>Val | CGG<br>Arg | 2232 |
| GCC<br>Ala<br>705 | TGG<br>Trp | ATT<br>Ile | GAG<br>Glu | AAG<br>Lys | ACC<br>Thr<br>710 | CTG<br>Leu | GAG<br>Glu | GAG<br>Glu | GGC<br>Gly | AGG<br>Arg<br>715 | AGG<br>Arg | CGG<br>Arg | GGG<br>Gly | TAC<br>Tyr | GTG<br>Val<br>720 | 2280 |
| GAG<br>Glu | ACC<br>Thr | CTC<br>Leu | TTC<br>Phe | GGC<br>Gly<br>725 | CGC<br>Arg | CGC<br>Arg | CGC<br>Arg | TAC<br>Tyr | GTG<br>Val<br>730 | CCA<br>Pro | GAC<br>Asp | CTA<br>Leu | GAG<br>Glu | GCC<br>Ala<br>735 | CGG<br>Arg | 2328 |
| GTG<br>Val | AAG<br>Lys | AGC<br>Ser | GTG<br>Val<br>740 | CGG<br>Arg | GAG<br>Glu | GCG<br>Ala | GCC<br>Ala | GAG<br>Glu<br>745 | CGC<br>Arg | ATG<br>Met | GCC<br>Ala | TTC<br>Phe | AAC<br>Asn<br>750 | ATG<br>Met | CCC<br>Pro | 2376 |
| GTC<br>Val | CAG<br>Gln | GGC<br>Gly<br>755 | ACC<br>Thr | GCC<br>Ala | GCC<br>Ala | GAC<br>Asp | CTC<br>Leu<br>760 | ATG<br>Met | AAG<br>Lys | CTG<br>Leu | GCT<br>Ala | ATG<br>Met<br>765 | GTG<br>Val | AAG<br>Lys | CTC<br>Leu | 2424 |
| TTC<br>Phe | CCC<br>Pro<br>770 | AGG<br>Arg | CTG<br>Leu | GAG<br>Glu | GAA<br>Glu<br>775 | ATG<br>Met | GGG<br>Gly | GCC<br>Ala | AGG<br>Arg | ATG<br>Met<br>780 | CTC<br>Leu | CTT<br>Leu | CAG<br>Gln | GTC<br>Val | CAC<br>His | 2472 |
| GAC<br>Asp<br>785 | GAG<br>Glu | CTG<br>Leu | GTC<br>Val | CTC<br>Leu | GAG<br>Glu<br>790 | GCC<br>Ala | CCA<br>Pro | AAA<br>Lys | GAG<br>Glu | AGG<br>Arg<br>795 | GCG<br>Ala | GAG<br>Glu | GCC<br>Ala | GTG<br>Val | GCC<br>Ala<br>800 | 2520 |

| | | | | | | | | | | | | | | | | |
|---|---|---|---|---|---|---|---|---|---|---|---|---|---|---|---|---|
| CGG | CTG | GCC | AAG | GAA | GTC | ATG | GAG | GGG | GTG | TAT | CCC | CTG | GCC | GTG | CCC | 2568 |
| Arg | Leu | Ala | Lys | Glu<br>805 | Val | Met | Glu | Gly | Val<br>810 | Tyr | Pro | Leu | Ala | Val<br>815 | Pro | |
| CTG | GAG | GTG | GAG | GTG | GGG | ATA | GGG | GAG | GAC | TGG | CTC | TCC | GCC | AAG | GAG | 2616 |
| Leu | Glu | Val | Glu<br>820 | Val | Gly | Ile | Gly | Glu<br>825 | Asp | Trp | Leu | Ser | Ala<br>830 | Lys | Glu | |

TGATACCACC　　　　　　　　　　　　　　　　　　　　　　　　　　　　　　2626

( 2 ) INFORMATION FOR SEQ ID NO:8:

( i ) SEQUENCE CHARACTERISTICS:
        ( A ) LENGTH: 832 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| | | | | | | | | | | | | | | |
|---|---|---|---|---|---|---|---|---|---|---|---|---|---|---|
| Met<br>1 | Arg | Gly | Met | Leu<br>5 | Pro | Leu | Phe | Glu | Pro<br>10 | Lys | Gly | Arg | Val | Leu<br>15 | Leu |
| Val | Asp | Gly | His<br>20 | His | Leu | Ala | Tyr | Arg<br>25 | Thr | Phe | His | Ala | Leu<br>30 | Lys | Gly |
| Leu | Thr | Thr<br>35 | Ser | Arg | Gly | Glu | Pro<br>40 | Val | Gln | Ala | Val | Tyr<br>45 | Gly | Phe | Ala |
| Lys | Ser<br>50 | Leu | Leu | Lys | Ala | Leu<br>55 | Lys | Glu | Asp | Gly | Asp<br>60 | Ala | Val | Ile | Val |
| Val<br>65 | Phe | Asp | Ala | Lys | Ala<br>70 | Pro | Ser | Phe | His | His<br>75 | Glu | Ala | Tyr | Gly | Gly<br>80 |
| Tyr | Lys | Ala | Gly | Arg<br>85 | Ala | Pro | Thr | Pro | Glu<br>90 | Asp | Phe | Pro | Arg | Gln<br>95 | Leu |
| Ala | Leu | Ile | Lys<br>100 | Glu | Leu | Val | Asp | Leu<br>105 | Leu | Gly | Leu | Ala | Arg<br>110 | Leu | Glu |
| Val | Pro | Gly<br>115 | Tyr | Glu | Ala | Asp | Asp<br>120 | Val | Leu | Ala | Ser | Leu<br>125 | Ala | Lys | Lys |
| Ala | Glu<br>130 | Lys | Glu | Gly | Tyr | Glu<br>135 | Val | Arg | Ile | Leu | Thr<br>140 | Ala | Asp | Lys | Asp |
| Leu<br>145 | Tyr | Gln | Leu | Leu | Ser<br>150 | Asp | Arg | Ile | His | Val<br>155 | Leu | His | Pro | Glu | Gly<br>160 |
| Tyr | Leu | Ile | Thr | Pro<br>165 | Ala | Trp | Leu | Trp | Glu<br>170 | Lys | Tyr | Gly | Leu | Arg<br>175 | Pro |
| Asp | Gln | Trp | Ala<br>180 | Asp | Tyr | Arg | Ala | Leu<br>185 | Thr | Gly | Asp | Glu | Ser<br>190 | Asp | Asn |
| Leu | Pro | Gly<br>195 | Val | Lys | Gly | Ile | Gly<br>200 | Glu | Lys | Thr | Ala | Arg<br>205 | Lys | Leu | Leu |
| Glu | Glu<br>210 | Trp | Gly | Ser | Leu | Glu<br>215 | Ala | Leu | Leu | Lys | Asn<br>220 | Leu | Asp | Arg | Leu |
| Lys<br>225 | Pro | Ala | Ile | Arg | Glu<br>230 | Lys | Ile | Leu | Ala | His<br>235 | Met | Asp | Asp | Leu | Lys<br>240 |
| Leu | Ser | Trp | Asp | Leu<br>245 | Ala | Lys | Val | Arg | Thr<br>250 | Asp | Leu | Pro | Leu | Glu<br>255 | Val |
| Asp | Phe | Ala | Lys<br>260 | Arg | Arg | Glu | Pro | Asp<br>265 | Arg | Glu | Arg | Leu | Arg<br>270 | Ala | Ile |
| Leu | Glu | Arg<br>275 | Leu | Glu | Phe | Gly | Ser<br>280 | Pro | Leu | His | Glu | Phe<br>285 | Gly | Leu | Leu |
| Glu | Ser<br>290 | Pro | Lys | Ala | Leu | Glu<br>295 | Glu | Ala | Pro | Trp | Pro<br>300 | Pro | Pro | Glu | Gly |

-continued

| | | | | | | | | | | | | | | | |
|---|---|---|---|---|---|---|---|---|---|---|---|---|---|---|---|
| Ala | Phe | Val | Gly | Phe | Val | Leu | Ser | Arg | Lys | Glu | Pro | Met | Trp | Ala | Asp |
| 305 | | | | 310 | | | | | 315 | | | | | | 320 |
| Leu | Leu | Ala | Leu | Ala | Ala | Arg | Gly | Gly | Arg | Val | His | Arg | Ala | Pro | |
| | | | | 325 | | | | 330 | | | | | 335 | | |
| Glu | Pro | Tyr | Lys | Ala | Leu | Arg | Asp | Leu | Lys | Glu | Ala | Arg | Gly | Leu | Leu |
| | | | 340 | | | | | 345 | | | | | 350 | | |
| Ala | Lys | Asp | Leu | Ser | Val | Leu | Ala | Leu | Arg | Glu | Gly | Leu | Gly | Leu | Pro |
| | | 355 | | | | | 360 | | | | | 365 | | | |
| Pro | Gly | Asp | Asp | Pro | Met | Leu | Leu | Ala | Tyr | Leu | Leu | Asp | Pro | Ser | Asn |
| | | 370 | | | | 375 | | | | | 380 | | | | |
| Thr | Thr | Pro | Glu | Gly | Val | Ala | Arg | Arg | Tyr | Gly | Gly | Glu | Trp | Thr | Glu |
| 385 | | | | | 390 | | | | | 395 | | | | | 400 |
| Glu | Ala | Gly | Glu | Arg | Ala | Ala | Leu | Ser | Glu | Arg | Leu | Phe | Ala | Asn | Leu |
| | | | | 405 | | | | | 410 | | | | | 415 | |
| Trp | Gly | Arg | Leu | Glu | Gly | Glu | Glu | Arg | Leu | Leu | Trp | Leu | Tyr | Arg | Glu |
| | | | 420 | | | | | 425 | | | | | 430 | | |
| Val | Glu | Arg | Pro | Leu | Ser | Ala | Val | Leu | Ala | His | Met | Glu | Ala | Thr | Gly |
| | | 435 | | | | | 440 | | | | | 445 | | | |
| Val | Arg | Leu | Asp | Val | Ala | Tyr | Leu | Arg | Ala | Leu | Ser | Leu | Glu | Val | Ala |
| | 450 | | | | | 455 | | | | | 460 | | | | |
| Glu | Glu | Ile | Ala | Arg | Leu | Glu | Ala | Glu | Val | Phe | Arg | Leu | Ala | Gly | His |
| 465 | | | | | 470 | | | | | 475 | | | | | 480 |
| Pro | Phe | Asn | Leu | Asn | Ser | Arg | Asp | Gln | Leu | Glu | Arg | Val | Leu | Phe | Asp |
| | | | | 485 | | | | | 490 | | | | | 495 | |
| Glu | Leu | Gly | Leu | Pro | Ala | Ile | Gly | Lys | Thr | Glu | Lys | Thr | Gly | Lys | Arg |
| | | | 500 | | | | | 505 | | | | | 510 | | |
| Ser | Thr | Ser | Ala | Ala | Val | Leu | Glu | Ala | Leu | Arg | Glu | Ala | His | Pro | Ile |
| | | 515 | | | | | 520 | | | | | 525 | | | |
| Val | Glu | Lys | Ile | Leu | Gln | Tyr | Arg | Glu | Leu | Thr | Lys | Leu | Lys | Ser | Thr |
| | 530 | | | | | 535 | | | | | 540 | | | | |
| Tyr | Ile | Asp | Pro | Leu | Pro | Asp | Leu | Ile | His | Pro | Arg | Thr | Gly | Arg | Leu |
| 545 | | | | | 550 | | | | | 555 | | | | | 560 |
| His | Thr | Arg | Phe | Asn | Gln | Thr | Ala | Thr | Ala | Thr | Gly | Arg | Leu | Ser | Ser |
| | | | | 565 | | | | | 570 | | | | | 575 | |
| Ser | Asp | Pro | Asn | Leu | Gln | Asn | Ile | Pro | Val | Arg | Thr | Pro | Leu | Gly | Gln |
| | | | 580 | | | | | 585 | | | | | 590 | | |
| Arg | Ile | Arg | Arg | Ala | Phe | Ile | Ala | Glu | Glu | Gly | Trp | Leu | Leu | Val | Ala |
| | | 595 | | | | | 600 | | | | | 605 | | | |
| Leu | Asp | Tyr | Ser | Gln | Ile | Glu | Leu | Arg | Val | Leu | Ala | His | Leu | Ser | Gly |
| | 610 | | | | | 615 | | | | | 620 | | | | |
| Asp | Glu | Asn | Leu | Ile | Arg | Val | Phe | Gln | Glu | Gly | Arg | Asp | Ile | His | Thr |
| 625 | | | | | 630 | | | | | 635 | | | | | 640 |
| Glu | Thr | Ala | Ser | Trp | Met | Phe | Gly | Val | Pro | Arg | Glu | Ala | Val | Asp | Pro |
| | | | | 645 | | | | | 650 | | | | | 655 | |
| Leu | Met | Arg | Arg | Ala | Ala | Lys | Thr | Ile | Asn | Phe | Gly | Val | Leu | Tyr | Gly |
| | | | 660 | | | | | 665 | | | | | 670 | | |
| Met | Ser | Ala | His | Arg | Leu | Ser | Gln | Glu | Leu | Ala | Ile | Pro | Tyr | Glu | Glu |
| | | 675 | | | | | 680 | | | | | 685 | | | |
| Ala | Gln | Ala | Phe | Ile | Glu | Arg | Tyr | Phe | Gln | Ser | Phe | Pro | Lys | Val | Arg |
| | 690 | | | | | 695 | | | | | 700 | | | | |
| Ala | Trp | Ile | Glu | Lys | Thr | Leu | Glu | Glu | Gly | Arg | Arg | Arg | Gly | Tyr | Val |
| 705 | | | | | 710 | | | | | 715 | | | | | 720 |
| Glu | Thr | Leu | Phe | Gly | Arg | Arg | Arg | Tyr | Val | Pro | Asp | Leu | Glu | Ala | Arg |

|     |     |     |     | 725 |     |     |     | 730 |     |     |     |     | 735 |     |     |
| --- | --- | --- | --- | --- | --- | --- | --- | --- | --- | --- | --- | --- | --- | --- | --- |
| Val | Lys | Ser | Val<br>740 | Arg | Glu | Ala | Ala | Glu<br>745 | Arg | Met | Ala | Phe | Asn<br>750 | Met | Pro |
| Val | Gln | Gly<br>755 | Thr | Ala | Ala | Asp | Leu<br>760 | Met | Lys | Leu | Ala | Met<br>765 | Val | Lys | Leu |
| Phe | Pro<br>770 | Arg | Leu | Glu | Glu | Met<br>775 | Gly | Ala | Arg | Met | Leu<br>780 | Leu | Gln | Val | His |
| Asp<br>785 | Glu | Leu | Val | Leu | Glu<br>790 | Ala | Pro | Lys | Glu | Arg<br>795 | Ala | Glu | Ala | Val | Ala<br>800 |
| Arg | Leu | Ala | Lys | Glu<br>805 | Val | Met | Glu | Gly | Val<br>810 | Tyr | Pro | Leu | Ala | Val<br>815 | Pro |
| Leu | Glu | Val | Glu<br>820 | Val | Gly | Ile | Gly | Glu<br>825 | Asp | Trp | Leu | Ser | Ala<br>830 | Lys | Glu |

( 2 ) INFORMATION FOR SEQ ID NO:9:

( i ) SEQUENCE CHARACTERISTICS:
        ( A ) LENGTH: 2626 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: mutation
        ( B ) LOCATION: replace(89, "g")
        ( D ) OTHER INFORMATION: /note="This mutation results in a
            nucleotide alteration at postion 89 of the native Taq DNA
            polymerase nucleotide sequence of C to G."

( i x ) FEATURE:
        ( A ) NAME/KEY: mutation
        ( B ) LOCATION: replace(934, "a")
        ( D ) OTHER INFORMATION: /note="This mutation results in a
            nucleotide alteration at position 934 of the native Taq
            DNA polymerase nucleotide sequence of T to A. This
            results in an amino acid change of Phe to Ile."

( i x ) FEATURE:
        ( A ) NAME/KEY: mutation
        ( B ) LOCATION: replace(962, "c")
        ( D ) OTHER INFORMATION: /note="This mutation results in a
            nucleotide alteration at position 962 of the native Taq
            DNA polymerase nucleotide sequence of T to C. This
            results in an amino acid change of Leu to Pro."

( i x ) FEATURE:
        ( A ) NAME/KEY: mutation
        ( B ) LOCATION: replace(2535, "a")
        ( D ) OTHER INFORMATION: /note="This mutation results in a
            nucleotide alteration at position 2535 of the native Taq
            DNA polymerase nucleotide sequence of G to A. This
            mutation is conservative."

( i x ) FEATURE:
        ( A ) NAME/KEY: mutation
        ( B ) LOCATION: replace(337, "a")
        ( D ) OTHER INFORMATION: /note="This mutation results in a
            nucleotide alteration at position 337 of the native Taq
            DNA polymerase nucleotide sequence of T to C. This
            change results in an amino acid change of Phe to Leu."

( i x ) FEATURE:
        ( A ) NAME/KEY: CDS
        ( B ) LOCATION: 121..2619

( i x ) FEATURE:
        ( A ) NAME/KEY: mat_peptide
        ( B ) LOCATION: 121..2616

( i x ) FEATURE:
    ( A ) NAME/KEY: -
    ( B ) LOCATION: 1..2619
    ( D ) OTHER INFORMATION: /note="pTarf2"

( x i ) SEQUENCE DESCRIPTION: SEQ ID NO:9:

```
AAGCTCAGAT CTACCTGCCT GAGGGCGTCC GGTTCCAGCT GGCCCTTCCC GAGGGGAGA       60

GGGAGGCGTT TCTAAAAGCC CTTCAGGAGG CTACCCGGGG GCGGGTGGTG GAAGGGTAAC    120

ATG AGG GGG ATG CTG CCC CTC TTT GAG CCC AAG GGC CGG GTC CTC CTG     168
Met Arg Gly Met Leu Pro Leu Phe Glu Pro Lys Gly Arg Val Leu Leu
 1               5                  10                  15

GTG GAC GGC CAC CAC CTG GCC TAC CGC ACC TTC CAC GCC CTG AAG GGC     216
Val Asp Gly His His Leu Ala Tyr Arg Thr Phe His Ala Leu Lys Gly
                20                  25                  30

CTC ACC ACC AGC CGG GGG GAG CCG GTG CAG GCG GTC TAC GGC TTC GCC     264
Leu Thr Thr Ser Arg Gly Glu Pro Val Gln Ala Val Tyr Gly Phe Ala
            35                  40                  45

AAG AGC CTC CTC AAG GCC CTC AAG GAG GAC GGG GAC GCG GTG ATC GTG     312
Lys Ser Leu Leu Lys Ala Leu Lys Glu Asp Gly Asp Ala Val Ile Val
    50                  55                  60

GTC TTT GAC GCC AAG GCC CCC TCC CTC CGC CAC GAG GCC TAC GGG GGG     360
Val Phe Asp Ala Lys Ala Pro Ser Leu Arg His Glu Ala Tyr Gly Gly
65                  70                  75                  80

TAC AAG GCG GGC CGG GCC CCC ACG CCG GAG GAC TTT CCC CGG CAA CTC     408
Tyr Lys Ala Gly Arg Ala Pro Thr Pro Glu Asp Phe Pro Arg Gln Leu
                85                  90                  95

GCC CTC ATC AAG GAG CTG GTG GAC CTC CTG GGG CTG GCG CGC CTC GAG     456
Ala Leu Ile Lys Glu Leu Val Asp Leu Leu Gly Leu Ala Arg Leu Glu
            100                 105                 110

GTC CCG GGC TAC GAG GCG GAC GAC GTC CTG GCC AGC CTG GCC AAG AAG     504
Val Pro Gly Tyr Glu Ala Asp Asp Val Leu Ala Ser Leu Ala Lys Lys
        115                 120                 125

GCG GAA AAG GAG GGC TAC GAG GTC CGC ATC CTC ACC GCC GAC AAA GAC     552
Ala Glu Lys Glu Gly Tyr Glu Val Arg Ile Leu Thr Ala Asp Lys Asp
    130                 135                 140

CTT TAC CAG CTC CTT TCC GAC CGC ATC CAC GTC CTC CAC CCC GAG GGG     600
Leu Tyr Gln Leu Leu Ser Asp Arg Ile His Val Leu His Pro Glu Gly
145                 150                 155                 160

TAC CTC ATC ACC CCG GCC TGG CTT TGG GAA AAG TAC GGC CTG AGG CCC     648
Tyr Leu Ile Thr Pro Ala Trp Leu Trp Glu Lys Tyr Gly Leu Arg Pro
                165                 170                 175

GAC CAG TGG GCC GAC TAC CGG GCC CTG ACC GGG GAC GAG TCC GAC AAC     696
Asp Gln Trp Ala Asp Tyr Arg Ala Leu Thr Gly Asp Glu Ser Asp Asn
            180                 185                 190

CTT CCC GGG GTC AAG GGC ATC GGG GAG AAG ACG GCG AGG AAG CTT CTG     744
Leu Pro Gly Val Lys Gly Ile Gly Glu Lys Thr Ala Arg Lys Leu Leu
        195                 200                 205

GAG GAG TGG GGG AGC CTG GAA GCC CTC CTC AAG AAC CTG GAC CGG CTG     792
Glu Glu Trp Gly Ser Leu Glu Ala Leu Leu Lys Asn Leu Asp Arg Leu
    210                 215                 220

AAG CCC GCC ATC CGG GAG AAG ATC CTG GCC CAC ATG GAC GAT CTG AAG     840
Lys Pro Ala Ile Arg Glu Lys Ile Leu Ala His Met Asp Asp Leu Lys
225                 230                 235                 240

CTC TCC TGG GAC CTG GCC AAG GTG CGC ACC GAC CTG CCC CTG GAG GTG     888
Leu Ser Trp Asp Leu Ala Lys Val Arg Thr Asp Leu Pro Leu Glu Val
                245                 250                 255

GAC TTC GCC AAA AGG CGG GAG CCC GAC CGG GAG AGG CTT AGG GCC ATT     936
Asp Phe Ala Lys Arg Arg Glu Pro Asp Arg Glu Arg Leu Arg Ala Ile
            260                 265                 270
```

| | | | | | | | | | | | | | | | | |
|---|---|---|---|---|---|---|---|---|---|---|---|---|---|---|---|---|
| CTG | GAG | AGG | CTT | GAG | TTT | GGC | AGC | CCC | CTC | CAC | GAG | TTC | GGC | CTT | CTG | 984 |
| Leu | Glu | Arg 275 | Leu | Glu | Phe | Gly | Ser 280 | Pro | Leu | His | Glu | Phe 285 | Gly | Leu | Leu | |
| GAA | AGC | CCC | AAG | GCC | CTG | GAG | GAG | GCC | CCC | TGG | CCC | CCG | CCG | GAA | GGG | 1032 |
| Glu | Ser 290 | Pro | Lys | Ala | Leu | Glu 295 | Glu | Ala | Pro | Trp | Pro 300 | Pro | Pro | Glu | Gly | |
| GCC | TTC | GTG | GGC | TTT | GTG | CTT | TCC | CGC | AAG | GAG | CCC | ATG | TGG | GCC | GAT | 1080 |
| Ala 305 | Phe | Val | Gly | Phe | Val 310 | Leu | Ser | Arg | Lys | Glu 315 | Pro | Met | Trp | Ala | Asp 320 | |
| CTT | CTG | GCC | CTG | GCC | GCC | GCC | AGG | GGG | GGC | CGG | GTC | CAC | CGG | GCC | CCC | 1128 |
| Leu | Leu | Ala | Leu | Ala | Ala 325 | Ala | Arg | Gly | Gly | Arg 330 | Val | His | Arg | Ala | Pro 335 | |
| GAG | CCT | TAT | AAA | GCC | CTC | AGG | GAC | CTG | AAG | GAG | GCG | CGG | GGG | CTT | CTC | 1176 |
| Glu | Pro | Tyr | Lys 340 | Ala | Leu | Arg | Asp | Leu 345 | Lys | Glu | Ala | Arg | Gly 350 | Leu | Leu | |
| GCC | AAA | GAC | CTG | AGC | GTT | CTG | GCC | CTG | AGG | GAA | GGC | CTT | GGC | CTC | CCG | 1224 |
| Ala | Lys | Asp 355 | Leu | Ser | Val | Leu | Ala 360 | Leu | Arg | Glu | Gly | Leu 365 | Gly | Leu | Pro | |
| CCC | GGC | GAC | GAC | CCC | ATG | CTC | CTC | GCC | TAC | CTC | CTG | GAC | CCT | TCC | AAC | 1272 |
| Pro | Gly | Asp 370 | Asp | Pro | Met | Leu | Leu 375 | Ala | Tyr | Leu | Leu | Asp 380 | Pro | Ser | Asn | |
| ACC | ACC | CCC | GAG | GGG | GTG | GCC | CGG | CGC | TAC | GGC | GGG | GAG | TGG | ACG | GAG | 1320 |
| Thr 385 | Thr | Pro | Glu | Gly | Val 390 | Ala | Arg | Arg | Tyr | Gly 395 | Gly | Glu | Trp | Thr | Glu 400 | |
| GAG | GCG | GGG | GAG | CGG | GCC | GCC | CTT | TCC | GAG | AGG | CTC | TTC | GCC | AAC | CTG | 1368 |
| Glu | Ala | Gly | Glu | Arg 405 | Ala | Ala | Leu | Ser | Glu 410 | Arg | Leu | Phe | Ala | Asn 415 | Leu | |
| TGG | GGG | AGG | CTT | GAG | GGG | GAG | GAG | AGG | CTC | CTT | TGG | CTT | TAC | CGG | GAG | 1416 |
| Trp | Gly | Arg | Leu 420 | Glu | Gly | Glu | Glu | Arg 425 | Leu | Leu | Trp | Leu | Tyr 430 | Arg | Glu | |
| GTG | GAG | AGG | CCC | CTT | TCC | GCT | GTC | CTG | GCC | CAC | ATG | GAG | GCC | ACG | GGG | 1464 |
| Val | Glu | Arg 435 | Pro | Leu | Ser | Ala | Val 440 | Leu | Ala | His | Met | Glu 445 | Ala | Thr | Gly | |
| GTG | CGC | CTG | GAC | GTG | GCC | TAT | CTC | AGG | GCC | TTG | TCC | CTG | GAG | GTG | GCC | 1512 |
| Val | Arg | Leu 450 | Asp | Val | Ala | Tyr | Leu 455 | Arg | Ala | Leu | Ser | Leu 460 | Glu | Val | Ala | |
| GAG | GAG | ATC | GCC | CGC | CTC | GAG | GCC | GAG | GTC | TTC | CGC | CTG | GCC | GGC | CAC | 1560 |
| Glu 465 | Glu | Ile | Ala | Arg | Leu 470 | Glu | Ala | Glu | Val | Phe 475 | Arg | Leu | Ala | Gly | His 480 | |
| CCC | TTC | AAC | CTC | AAC | TCC | CGG | GAC | CAG | CTG | GAA | AGG | GTC | CTC | TTT | GAC | 1608 |
| Pro | Phe | Asn | Leu | Asn 485 | Ser | Arg | Asp | Gln | Leu 490 | Glu | Arg | Val | Leu | Phe 495 | Asp | |
| GAG | CTA | GGG | CTT | CCC | GCC | ATC | GGC | AAG | ACG | GAG | AAG | ACC | GGC | AAG | CGC | 1656 |
| Glu | Leu | Gly | Leu 500 | Pro | Ala | Ile | Gly | Lys 505 | Thr | Glu | Lys | Thr | Gly 510 | Lys | Arg | |
| TCC | ACC | AGC | GCC | GCC | GTC | CTG | GAG | GCC | CTC | CGC | GAG | GCC | CAC | CCC | ATC | 1704 |
| Ser | Thr | Ser 515 | Ala | Ala | Val | Leu | Glu 520 | Ala | Leu | Arg | Glu | Ala 525 | His | Pro | Ile | |
| GTG | GAG | AAG | ATC | CTG | CAG | TAC | CGG | GAG | CTC | ACC | AAG | CTG | AAG | AGC | ACC | 1752 |
| Val | Glu | Lys 530 | Ile | Leu | Gln | Tyr | Arg 535 | Glu | Leu | Thr | Lys | Leu 540 | Lys | Ser | Thr | |
| TAC | ATT | GAC | CCC | TTG | CCG | GAC | CTC | ATC | CAC | CCC | AGG | ACG | GGC | CGC | CTC | 1800 |
| Tyr | Ile | Asp | Pro 545 | Leu | Pro | Asp | Leu | Ile 550 | His | Pro | Arg | Thr | Gly 555 | Arg | Leu 560 | |
| CAC | ACC | CGC | TTC | AAC | CAG | ACG | GCC | ACG | GCC | ACG | GGC | AGG | CTA | AGT | AGC | 1848 |
| His | Thr | Arg | Phe | Asn 565 | Gln | Thr | Ala | Thr | Ala 570 | Thr | Gly | Arg | Leu | Ser 575 | Ser | |
| TCC | GAT | CCC | AAC | CTC | CAG | AAC | ATC | CCC | GTC | CGC | ACC | CCG | CTT | GGG | CAG | 1896 |
| Ser | Asp | Pro | Asn | Leu | Gln | Asn | Ile | Pro | Val | Arg | Thr | Pro | Leu | Gly | Gln | |

-continued

|  |  |  | 580 |  |  |  | 585 |  |  |  | 590 |  |  |  |  |
|---|---|---|---|---|---|---|---|---|---|---|---|---|---|---|---|
| AGG | ATC | CGC | CGG | GCC | TTC | ATC | GCC | GAG | GAG | GGG | TGG | CTA | TTG | GTG | GCC | 1944 |
| Arg | Ile | Arg<br>595 | Arg | Ala | Phe | Ile | Ala<br>600 | Glu | Glu | Gly | Trp | Leu<br>605 | Leu | Val | Ala |  |
| CTG | GAC | TAT | AGC | CAG | ATA | GAG | CTC | AGG | GTG | CTG | GCC | CAC | CTC | TCC | GGC | 1992 |
| Leu | Asp<br>610 | Tyr | Ser | Gln | Ile | Glu<br>615 | Leu | Arg | Val | Leu | Ala<br>620 | His | Leu | Ser | Gly |  |
| GAC | GAG | AAC | CTG | ATC | CGG | GTC | TTC | CAG | GAG | GGG | CGG | GAC | ATC | CAC | ACG | 2040 |
| Asp | Glu<br>625 | Asn | Leu | Ile | Arg<br>630 | Val | Phe | Gln | Glu | Gly<br>635 | Arg | Asp | Ile | His | Thr<br>640 |  |
| GAG | ACC | GCC | AGC | TGG | ATG | TTC | GGC | GTC | CCC | CGG | GAG | GCC | GTG | GAC | CCC | 2088 |
| Glu | Thr | Ala | Ser | Trp<br>645 | Met | Phe | Gly | Val | Pro<br>650 | Arg | Glu | Ala | Val | Asp<br>655 | Pro |  |
| CTG | ATG | CGC | CGG | GCG | GCC | AAG | ACC | ATC | AAC | TTC | GGG | GTC | CTC | TAC | GGC | 2136 |
| Leu | Met | Arg | Arg<br>660 | Ala | Ala | Lys | Thr | Ile<br>665 | Asn | Phe | Gly | Val | Leu<br>670 | Tyr | Gly |  |
| ATG | TCG | GCC | CAC | CGC | CTC | TCC | CAG | GAG | CTA | GCC | ATC | CCT | TAC | GAG | GAG | 2184 |
| Met | Ser | Ala | His<br>675 | Arg | Leu | Ser | Gln | Glu<br>680 | Leu | Ala | Ile | Pro | Tyr<br>685 | Glu | Glu |  |
| GCC | CAG | GCC | TTC | ATT | GAG | CGC | TAC | TTT | CAG | AGC | TTC | CCC | AAG | GTG | CGG | 2232 |
| Ala | Gln<br>690 | Ala | Phe | Ile | Glu | Arg<br>695 | Tyr | Phe | Gln | Ser | Phe<br>700 | Pro | Lys | Val | Arg |  |
| GCC | TGG | ATT | GAG | AAG | ACC | CTG | GAG | GAG | GGC | AGG | AGG | CGG | GGG | TAC | GTG | 2280 |
| Ala | Trp<br>705 | Ile | Glu | Lys | Thr | Leu<br>710 | Glu | Glu | Gly | Arg | Arg<br>715 | Arg | Gly | Tyr | Val<br>720 |  |
| GAG | ACC | CTC | TTC | GGC | CGC | CGC | CGC | TAC | GTG | CCA | GAC | CTA | GAG | GCC | CGG | 2328 |
| Glu | Thr | Leu | Phe | Gly<br>725 | Arg | Arg | Arg | Tyr | Val<br>730 | Pro | Asp | Leu | Glu | Ala<br>735 | Arg |  |
| GTG | AAG | AGC | GTG | CGG | GAG | GCG | GCC | GAG | CGC | ATG | GCC | TTC | AAC | ATG | CCC | 2376 |
| Val | Lys | Ser | Val<br>740 | Arg | Glu | Ala | Ala | Glu<br>745 | Arg | Met | Ala | Phe | Asn<br>750 | Met | Pro |  |
| GTC | CAG | GGC | ACC | GCC | GCC | GAC | CTC | ATG | AAG | CTG | GCT | ATG | GTG | AAG | CTC | 2424 |
| Val | Gln | Gly<br>755 | Thr | Ala | Ala | Asp | Leu<br>760 | Met | Lys | Leu | Ala | Met<br>765 | Val | Lys | Leu |  |
| TTC | CCC | AGG | CTG | GAG | GAA | ATG | GGG | GCC | AGG | ATG | CTC | CTT | CAG | GTC | CAC | 2472 |
| Phe | Pro<br>770 | Arg | Leu | Glu | Glu | Met<br>775 | Gly | Ala | Arg | Met | Leu<br>780 | Leu | Gln | Val | His |  |
| GAC | GAG | CTG | GTC | CTC | GAG | GCC | CCA | AAA | GAG | AGG | GCG | GAG | GCC | GTG | GCC | 2520 |
| Asp | Glu<br>785 | Leu | Val | Leu | Glu<br>790 | Ala | Pro | Lys | Glu | Arg<br>795 | Ala | Glu | Ala | Val | Ala<br>800 |  |
| CGG | CTG | GCC | AAG | GAA | GTC | ATG | GAG | GGG | GTG | TAT | CCC | CTG | GCC | GTG | CCC | 2568 |
| Arg | Leu | Ala | Lys | Glu<br>805 | Val | Met | Glu | Gly | Val<br>810 | Tyr | Pro | Leu | Ala | Val<br>815 | Pro |  |
| CTG | GAG | GTG | GAG | GTG | GGG | ATA | GGG | GAG | GAC | TGG | CTC | TCC | GCC | AAG | GAG | 2616 |
| Leu | Glu | Val | Glu<br>820 | Val | Gly | Ile | Gly | Glu<br>825 | Asp | Trp | Leu | Ser | Ala<br>830 | Lys | Glu |  |

TGATACCACC   2626

( 2 ) INFORMATION FOR SEQ ID NO:10:

( i ) SEQUENCE CHARACTERISTICS:
        ( A ) LENGTH: 832 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| Met | Arg | Gly | Met | Leu | Pro | Leu | Phe | Glu | Pro | Lys | Gly | Arg | Val | Leu | Leu |
|---|---|---|---|---|---|---|---|---|---|---|---|---|---|---|---|
| 1 |  |  |  | 5 |  |  |  |  | 10 |  |  |  |  | 15 |  |

| | | | | | | | | | | | | | | |
|---|---|---|---|---|---|---|---|---|---|---|---|---|---|---|
| Val | Asp | Gly | His | His | Leu | Ala | Tyr | Arg | Thr | Phe | His | Ala | Leu | Lys | Gly |
| | | | 20 | | | | 25 | | | | | 30 | | | |
| Leu | Thr | Thr | Ser | Arg | Gly | Glu | Pro | Val | Gln | Ala | Val | Tyr | Gly | Phe | Ala |
| | | 35 | | | | 40 | | | | | 45 | | | | |
| Lys | Ser | Leu | Leu | Lys | Ala | Leu | Lys | Glu | Asp | Gly | Asp | Ala | Val | Ile | Val |
| | 50 | | | | | 55 | | | | | 60 | | | | |
| Val | Phe | Asp | Ala | Lys | Ala | Pro | Ser | Leu | Arg | His | Glu | Ala | Tyr | Gly | Gly |
| 65 | | | | | 70 | | | | | 75 | | | | | 80 |
| Tyr | Lys | Ala | Gly | Arg | Ala | Pro | Thr | Pro | Glu | Asp | Phe | Pro | Arg | Gln | Leu |
| | | | | 85 | | | | | 90 | | | | | 95 | |
| Ala | Leu | Ile | Lys | Glu | Leu | Val | Asp | Leu | Leu | Gly | Leu | Ala | Arg | Leu | Glu |
| | | | 100 | | | | | 105 | | | | | 110 | | |
| Val | Pro | Gly | Tyr | Glu | Ala | Asp | Asp | Val | Leu | Ala | Ser | Leu | Ala | Lys | Lys |
| | | 115 | | | | | 120 | | | | | 125 | | | |
| Ala | Glu | Lys | Glu | Gly | Tyr | Glu | Val | Arg | Ile | Leu | Thr | Ala | Asp | Lys | Asp |
| | 130 | | | | | 135 | | | | | 140 | | | | |
| Leu | Tyr | Gln | Leu | Leu | Ser | Asp | Arg | Ile | His | Val | Leu | His | Pro | Glu | Gly |
| 145 | | | | | 150 | | | | | 155 | | | | | 160 |
| Tyr | Leu | Ile | Thr | Pro | Ala | Trp | Leu | Trp | Glu | Lys | Tyr | Gly | Leu | Arg | Pro |
| | | | | 165 | | | | | 170 | | | | | 175 | |
| Asp | Gln | Trp | Ala | Asp | Tyr | Arg | Ala | Leu | Thr | Gly | Asp | Glu | Ser | Asp | Asn |
| | | | 180 | | | | | 185 | | | | | 190 | | |
| Leu | Pro | Gly | Val | Lys | Gly | Ile | Gly | Glu | Lys | Thr | Ala | Arg | Lys | Leu | Leu |
| | | 195 | | | | | 200 | | | | | 205 | | | |
| Glu | Glu | Trp | Gly | Ser | Leu | Glu | Ala | Leu | Leu | Lys | Asn | Leu | Asp | Arg | Leu |
| | 210 | | | | | 215 | | | | | 220 | | | | |
| Lys | Pro | Ala | Ile | Arg | Glu | Lys | Ile | Leu | Ala | His | Met | Asp | Asp | Leu | Lys |
| 225 | | | | | 230 | | | | | 235 | | | | | 240 |
| Leu | Ser | Trp | Asp | Leu | Ala | Lys | Val | Arg | Thr | Asp | Leu | Pro | Leu | Glu | Val |
| | | | | 245 | | | | | 250 | | | | | 255 | |
| Asp | Phe | Ala | Lys | Arg | Arg | Glu | Pro | Asp | Arg | Glu | Arg | Leu | Arg | Ala | Ile |
| | | | 260 | | | | | 265 | | | | | 270 | | |
| Leu | Glu | Arg | Leu | Glu | Phe | Gly | Ser | Pro | Leu | His | Glu | Phe | Gly | Leu | Leu |
| | | 275 | | | | | 280 | | | | | 285 | | | |
| Glu | Ser | Pro | Lys | Ala | Leu | Glu | Glu | Ala | Pro | Trp | Pro | Pro | Pro | Glu | Gly |
| | 290 | | | | | 295 | | | | | 300 | | | | |
| Ala | Phe | Val | Gly | Phe | Val | Leu | Ser | Arg | Lys | Glu | Pro | Met | Trp | Ala | Asp |
| 305 | | | | | 310 | | | | | 315 | | | | | 320 |
| Leu | Leu | Ala | Leu | Ala | Ala | Ala | Arg | Gly | Gly | Arg | Val | His | Arg | Ala | Pro |
| | | | | 325 | | | | | 330 | | | | | 335 | |
| Glu | Pro | Tyr | Lys | Ala | Leu | Arg | Asp | Leu | Lys | Glu | Ala | Arg | Gly | Leu | Leu |
| | | | 340 | | | | | 345 | | | | | 350 | | |
| Ala | Lys | Asp | Leu | Ser | Val | Leu | Ala | Leu | Arg | Glu | Gly | Leu | Gly | Leu | Pro |
| | | 355 | | | | | 360 | | | | | 365 | | | |
| Pro | Gly | Asp | Asp | Pro | Met | Leu | Leu | Ala | Tyr | Leu | Leu | Asp | Pro | Ser | Asn |
| | 370 | | | | | 375 | | | | | 380 | | | | |
| Thr | Thr | Pro | Glu | Gly | Val | Ala | Arg | Arg | Tyr | Gly | Gly | Glu | Trp | Thr | Glu |
| 385 | | | | | 390 | | | | | 395 | | | | | 400 |
| Glu | Ala | Gly | Glu | Arg | Ala | Ala | Leu | Ser | Glu | Arg | Leu | Phe | Ala | Asn | Leu |
| | | | | 405 | | | | | 410 | | | | | 415 | |
| Trp | Gly | Arg | Leu | Glu | Gly | Glu | Glu | Arg | Leu | Leu | Trp | Leu | Tyr | Arg | Glu |
| | | | 420 | | | | | 425 | | | | | 430 | | |
| Val | Glu | Arg | Pro | Leu | Ser | Ala | Val | Leu | Ala | His | Met | Glu | Ala | Thr | Gly |

```
                    435                     440                     445
Val  Arg  Leu  Asp  Val  Ala  Tyr  Leu  Arg  Ala  Leu  Ser  Leu  Glu  Val  Ala
     450                      455                     460
Glu  Glu  Ile  Ala  Arg  Leu  Glu  Ala  Glu  Val  Phe  Arg  Leu  Ala  Gly  His
465                 470                      475                          480
Pro  Phe  Asn  Leu  Asn  Ser  Arg  Asp  Gln  Leu  Glu  Arg  Val  Leu  Phe  Asp
               485                      490                          495
Glu  Leu  Gly  Leu  Pro  Ala  Ile  Gly  Lys  Thr  Glu  Lys  Thr  Gly  Lys  Arg
               500                      505                     510
Ser  Thr  Ser  Ala  Ala  Val  Leu  Glu  Ala  Leu  Arg  Glu  Ala  His  Pro  Ile
          515                      520                     525
Val  Glu  Lys  Ile  Leu  Gln  Tyr  Arg  Glu  Leu  Thr  Lys  Leu  Lys  Ser  Thr
     530                      535                     540
Tyr  Ile  Asp  Pro  Leu  Pro  Asp  Leu  Ile  His  Pro  Arg  Thr  Gly  Arg  Leu
545                      550                      555                         560
His  Thr  Arg  Phe  Asn  Gln  Thr  Ala  Thr  Ala  Thr  Gly  Arg  Leu  Ser  Ser
               565                      570                          575
Ser  Asp  Pro  Asn  Leu  Gln  Asn  Ile  Pro  Val  Arg  Thr  Pro  Leu  Gly  Gln
               580                      585                     590
Arg  Ile  Arg  Arg  Ala  Phe  Ile  Ala  Glu  Glu  Gly  Trp  Leu  Leu  Val  Ala
          595                      600                     605
Leu  Asp  Tyr  Ser  Gln  Ile  Glu  Leu  Arg  Val  Leu  Ala  His  Leu  Ser  Gly
     610                      615                     620
Asp  Glu  Asn  Leu  Ile  Arg  Val  Phe  Gln  Glu  Gly  Arg  Asp  Ile  His  Thr
625                      630                      635                         640
Glu  Thr  Ala  Ser  Trp  Met  Phe  Gly  Val  Pro  Arg  Glu  Ala  Val  Asp  Pro
               645                      650                          655
Leu  Met  Arg  Arg  Ala  Ala  Lys  Thr  Ile  Asn  Phe  Gly  Val  Leu  Tyr  Gly
               660                      665                     670
Met  Ser  Ala  His  Arg  Leu  Ser  Gln  Glu  Leu  Ala  Ile  Pro  Tyr  Glu  Glu
          675                      680                     685
Ala  Gln  Ala  Phe  Ile  Glu  Arg  Tyr  Phe  Gln  Ser  Phe  Pro  Lys  Val  Arg
     690                      695                     700
Ala  Trp  Ile  Glu  Lys  Thr  Leu  Glu  Glu  Gly  Arg  Arg  Arg  Gly  Tyr  Val
705                      710                      715                         720
Glu  Thr  Leu  Phe  Gly  Arg  Arg  Arg  Tyr  Val  Pro  Asp  Leu  Glu  Ala  Arg
               725                      730                          735
Val  Lys  Ser  Val  Arg  Glu  Ala  Ala  Glu  Arg  Met  Ala  Phe  Asn  Met  Pro
               740                      745                     750
Val  Gln  Gly  Thr  Ala  Ala  Asp  Leu  Met  Lys  Leu  Ala  Met  Val  Lys  Leu
          755                      760                     765
Phe  Pro  Arg  Leu  Glu  Glu  Met  Gly  Ala  Arg  Met  Leu  Leu  Gln  Val  His
     770                      775                     780
Asp  Glu  Leu  Val  Leu  Glu  Ala  Pro  Lys  Glu  Arg  Ala  Glu  Ala  Val  Ala
785                      790                      795                         800
Arg  Leu  Ala  Lys  Glu  Val  Met  Glu  Gly  Val  Tyr  Pro  Leu  Ala  Val  Pro
               805                      810                          815
Leu  Glu  Val  Glu  Val  Gly  Ile  Gly  Glu  Asp  Trp  Leu  Ser  Ala  Lys  Glu
               820                      825                     830
```

( 2 ) INFORMATION FOR SEQ ID NO:11:

( i ) SEQUENCE CHARACTERISTICS:
    ( A ) LENGTH: 18 base pairs (B) TYPE: nucleic acid
(C) STRANDEDNESS: single
(D) TOPOLOGY: linear (i i) MOLECULE TYPE: cDNA (i i i) HYPOTHETICAL: NO (i x) FEATURE:
(A) NAME/KEY: -
(B) LOCATION: 1..18
(D) OTHER INFORMATION: /note="PCR reverse primer used for PUC18"

(x i) SEQUENCE DESCRIPTION: SEQ ID NO:11:

CAGGAAACAG CTATGACC 18

(2) INFORMATION FOR SEQ ID NO:12:

(i) SEQUENCE CHARACTERISTICS:
(A) LENGTH: 15 base pairs
(B) TYPE: nucleic acid
(C) STRANDEDNESS: single
(D) TOPOLOGY: linear (i i) MOLECULE TYPE: cDNA (i i i) HYPOTHETICAL: NO (i x) FEATURE:
(A) NAME/KEY: -
(B) LOCATION: 11..15
(D) OTHER INFORMATION: /note="PCR sequencing primer 628A used for pUC18"

(x i) SEQUENCE DESCRIPTION: SEQ ID NO:12:

CCCAAAGCCA GGCCG 15

(2) INFORMATION FOR SEQ ID NO:13:

(i) SEQUENCE CHARACTERISTICS:
(A) LENGTH: 15 base pairs
(B) TYPE: nucleic acid
(C) STRANDEDNESS: double
(D) TOPOLOGY: linear (i i) MOLECULE TYPE: cDNA (i i i) HYPOTHETICAL: NO (i x) FEATURE:
(A) NAME/KEY: -
(B) LOCATION: 1..15
(D) OTHER INFORMATION: /note="Sequencing primer 1155A"

(x i) SEQUENCE DESCRIPTION: SEQ ID NO:13:

CAGGTCCCTG AGGGC 15

(2) INFORMATION FOR SEQ ID NO:14:

(i) SEQUENCE CHARACTERISTICS:
(A) LENGTH: 46 base pairs
(B) TYPE: nucleic acid
(C) STRANDEDNESS: single
(D) TOPOLOGY: linear (i i) MOLECULE TYPE: cDNA (i i i) HYPOTHETICAL: NO (i x) FEATURE:
(A) NAME/KEY: -
(B) LOCATION: 1..46

(D) OTHER INFORMATION: /note="pUC18 - pLSM5 5'junction"

(xi) SEQUENCE DESCRIPTION: SEQ ID NO:14:

AATTTCACAC AGGAAACAGC TATGACCATG ATTACGAATT CTAAAA    46

(2) INFORMATION FOR SEQ ID NO:15:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (ix) FEATURE:
        (A) NAME/KEY: -
        (B) LOCATION: 1..63
        (D) OTHER INFORMATION: /note="pUC18 - pLSM5 3'sequence junction"

(xi) SEQUENCE DESCRIPTION: SEQ ID NO:15:

CAAGGAGTGA GATTCTCTAG AGTCGACCTG CAGGCATGCA AGCTTGGCAC TGGCCGTCGT    60

TTT    63

1. A modified Taq polymerase gene comprising the native Taq DNA polymerase gene wherein the nucleotide at position 193 is T and the nucleotide at position 504 is A.

2. A modified Taq DNA polymerase gene comprising the native Taq DNA polymerase gene wherein the nucleotide at position 89 is G, the nucleotide at position 193 is T, the nucleotide at position 504 is A, the nucleotide at position 934 is A, the nucleotide at position 962 is C, and the nucleotide at position 2535 is A.

3. A modified Taq polymerase comprising the native Taq DNA polymerase wherein the amino acid at position 25 is Cys.

4. A modified Taq polymerase comprising the native Taq DNA polymerase wherein the amino acid at position 25 is Cys, the amino acid at position 272 is Ile, and the amino acid at position 281 is Pro.

5. A modified Taq DNA polymerase gene comprising the native Taq DNA polymerase gene wherein the nucleotide at position 341 is A.

6. A modified Taq DNA polymerase gene comprising the native Taq DNA polymerase gene wherein the nucleotide at position 89 is G, the nucleotide at position 341 is A, the nucleotide at position 934 is A, the nucleotide at position 962 is C, and the nucleotide at position 2535 is A.

7. A modified Taq DNA polymerase comprising the native Taq DNA polymerase wherein the amino acid at position 74 is His.

8. A modified Taq DNA polymerase comprising the native Taq DNA polymerase wherein the amino acid at position 74 is His, the amino acid at position 272 is Ile, and the amino acid at position 281 is Pro.

9. Host cells that are transfected with the modified Taq DNA polymerase gene of claim 1 and that express the gene.

10. Host cells that are transfected with the modified Taq DNA polymerase gene of claim 2 and that express the gene.

11. Host cells that are transfected with the modified Taq DNA polymerase gene of claim 5 and that express the gene.

12. Host cells that are transfected with the modified Taq DNA polymerase gene of claim 6 and that express the gene.

\* \* \* \* \*